(12) United States Patent
Kim

(10) Patent No.: US 10,366,487 B2
(45) Date of Patent: Jul. 30, 2019

(54) ELECTRONIC APPARATUS FOR PROVIDING HEALTH STATUS INFORMATION, METHOD OF CONTROLLING THE SAME, AND COMPUTER-READABLE STORAGE MEDIUM

(71) Applicant: SAMSUNG ELECTRONICS CO., LTD., Suwon-si (KR)

(72) Inventor: Seon-ae Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/658,666

(22) Filed: Mar. 16, 2015

(65) Prior Publication Data

US 2015/0261996 A1 Sep. 17, 2015

(30) Foreign Application Priority Data

Mar. 14, 2014 (KR) .................. 10-2014-0030457
Jul. 31, 2014 (KR) .................. 10-2014-0098639

(51) Int. Cl.
*H04N 5/232* (2006.01)
*G16H 50/00* (2018.01)
(Continued)

(52) U.S. Cl.
CPC ............ *G06T 7/0012* (2013.01); *G06F 19/00* (2013.01); *G06K 9/00255* (2013.01);
(Continued)

(58) Field of Classification Search
CPC .... H04N 5/23229; G16H 50/20; G16H 50/30; G06T 7/0012; G06T 7/0014; G06T 7/136; G06K 9/00255; G06K 9/00261
See application file for complete search history.

(56) References Cited

U.S. PATENT DOCUMENTS 8,576,071 B2 * 11/2013 Lo ..................... G06F 21/35
340/5.2
8,942,510 B2 1/2015 Nashida et al.
(Continued)

FOREIGN PATENT DOCUMENTS

CN 102096810 A 6/2011
CN 102985007 A 3/2013
(Continued)

OTHER PUBLICATIONS

Written Opinion dated May 29, 2015 issued by International Searching Authority in counterpart International Patent Application No. PCT/KR2015/002535.
(Continued)

*Primary Examiner* — Daniel I Walsh
(74) *Attorney, Agent, or Firm* — Sughrue Mion, PLLC

(57) ABSTRACT

Provided is a device and method of providing health status information. The device includes: a device including: a storage configured to store a first image including a face of a user and first health status information extracted from the first image; an imager configured to capture an image; a controller configured to control the imager to capture a second image including the face of the user and to extract second health status information from the captured second image; and a display configured to output the second image and information other than the stored first health status information from among the extracted second health status information.

23 Claims, 93 Drawing Sheets

(51) Int. Cl.
  *G16H 50/30* (2018.01)
  *G06T 7/00* (2017.01)
  *G06K 9/00* (2006.01)
  *H04N 7/14* (2006.01)
  *G06K 9/62* (2006.01)
  *H04N 5/262* (2006.01)
  *H04N 7/18* (2006.01)
  *G16H 50/20* (2018.01)
  *G06F 19/00* (2018.01)

(52) U.S. Cl.
  CPC ....... *G06K 9/00261* (2013.01); *G06K 9/6215* (2013.01); *G16H 50/20* (2018.01); *G16H 50/30* (2018.01); *H04N 5/23216* (2013.01); *H04N 5/23222* (2013.01); *H04N 5/23229* (2013.01); *H04N 5/23293* (2013.01); *H04N 5/2628* (2013.01); *H04N 7/141* (2013.01); *H04N 7/18* (2013.01)

(56) References Cited

U.S. PATENT DOCUMENTS

| | | | | |
|---|---|---|---|---|
| 9,195,881 B2* | 11/2015 | Kim | | G06T 3/0006 |
| 9,652,664 B1* | 5/2017 | Bogdan | | G06K 9/00288 |
| 9,723,997 B1* | 8/2017 | Lamego | | A61B 5/0205 |
| 10,217,286 B1* | 2/2019 | Angel | | G06T 19/006 |
| 2002/0103574 A1* | 8/2002 | Funada | | G06K 9/00288 |
| | | | | 700/245 |
| 2003/0169906 A1* | 9/2003 | Gokturk | | G06K 9/00201 |
| | | | | 382/115 |
| 2003/0190060 A1* | 10/2003 | Pengwu | | G06K 9/00268 |
| | | | | 382/118 |
| 2004/0091137 A1* | 5/2004 | Yoon | | G06K 9/00268 |
| | | | | 382/118 |
| 2005/0100208 A1* | 5/2005 | Suzuki | | G06T 5/007 |
| | | | | 382/157 |
| 2005/0196021 A1* | 9/2005 | Seto | | G06K 9/00221 |
| | | | | 382/118 |
| 2006/0008150 A1* | 1/2006 | Zhao | | G06K 9/00288 |
| | | | | 382/190 |
| 2006/0072798 A1* | 4/2006 | Allen | | A61B 5/0013 |
| | | | | 382/128 |
| 2006/0110014 A1* | 5/2006 | Philomin | | G06K 9/00288 |
| | | | | 382/118 |
| 2007/0040907 A1* | 2/2007 | Kern et al. | | 348/77 |
| 2007/0133844 A1* | 6/2007 | Waehner | | G06K 9/00221 |
| | | | | 382/118 |
| 2007/0183635 A1* | 8/2007 | Weidhaas | | B60R 25/25 |
| | | | | 382/118 |
| 2007/0265813 A1* | 11/2007 | Unal | | G06T 7/0012 |
| | | | | 703/2 |
| 2008/0080781 A1* | 4/2008 | Pote | | A61B 5/0071 |
| | | | | 382/255 |
| 2008/0292151 A1* | 11/2008 | Kurtz | | A61B 3/10 |
| | | | | 382/128 |
| 2008/0294013 A1* | 11/2008 | Gobeyn | | A61B 5/0059 |
| | | | | 600/300 |
| 2008/0294017 A1* | 11/2008 | Gobeyn et al. | | 600/301 |
| 2009/0024050 A1* | 1/2009 | Jung et al. | | 600/544 |
| 2009/0034806 A1* | 2/2009 | Hayase | | G06F 3/0482 |
| | | | | 382/118 |
| 2009/0060287 A1* | 3/2009 | Hyde et al. | | 382/118 |
| 2009/0062686 A1* | 3/2009 | Hyde et al. | | 600/558 |
| 2009/0160229 A1* | 6/2009 | Mabuchi et al. | | 297/217.3 |
| 2009/0160609 A1* | 6/2009 | Lin et al. | | 340/5.83 |
| 2010/0104217 A1* | 4/2010 | Tsurumi | | G06K 9/00335 |
| | | | | 382/284 |
| 2010/0146235 A1* | 6/2010 | Weber et al. | | 711/165 |
| 2010/0317420 A1* | 12/2010 | Hoffberg | | G06Q 30/0207 |
| | | | | 463/1 |
| 2011/0082391 A1* | 4/2011 | Kane | | A61B 5/1075 |
| | | | | 600/587 |
| 2011/0106557 A1* | 5/2011 | Gazula | | 705/3 |
| 2011/0128289 A1* | 6/2011 | Zingaretti | | G06T 7/0014 |
| | | | | 345/428 |
| 2011/0188738 A1* | 8/2011 | Roussel | | G06T 17/20 |
| | | | | 382/154 |
| 2011/0276507 A1* | 11/2011 | O'Malley | | G06Q 10/00 |
| | | | | 705/321 |
| 2011/0288379 A1 | 11/2011 | Wu | | |
| 2012/0009896 A1* | 1/2012 | Bandyopadhyay et al. | | |
| | | | | 455/411 |
| 2012/0069131 A1* | 3/2012 | Abelow | | 348/14.01 |
| 2012/0140068 A1* | 6/2012 | Monroe et al. | | 348/143 |
| 2012/0235790 A1* | 9/2012 | Zhao et al. | | 340/5.83 |
| 2012/0262481 A1* | 10/2012 | Allen | | A45D 44/005 |
| | | | | 345/629 |
| 2012/0264446 A1 | 10/2012 | Xie et al. | | |
| 2012/0299731 A1* | 11/2012 | Triener | | 340/573.1 |
| 2012/0321143 A1 | 12/2012 | Krupka et al. | | |
| 2013/0063611 A1* | 3/2013 | Papakipos et al. | | 348/207.11 |
| 2013/0097695 A1* | 4/2013 | Sipe et al. | | 726/17 |
| 2013/0141605 A1* | 6/2013 | Kim | | G06T 11/60 |
| | | | | 348/222.1 |
| 2013/0184537 A1* | 7/2013 | Konuma | | A61B 5/0033 |
| | | | | 600/300 |
| 2013/0232082 A1* | 9/2013 | Krawczewicz | | G06F 19/323 |
| | | | | 705/55 |
| 2013/0251244 A1* | 9/2013 | Wei | | G06K 9/00281 |
| | | | | 382/159 |
| 2013/0301925 A1* | 11/2013 | Nashida | | G06T 11/60 |
| | | | | 382/195 |
| 2013/0314401 A1* | 11/2013 | Engle | | G06T 19/006 |
| | | | | 345/419 |
| 2014/0028823 A1 | 1/2014 | Tahk et al. | | |
| 2014/0121540 A1* | 5/2014 | Raskin | | A61B 5/6898 |
| | | | | 600/479 |
| 2014/0185939 A1* | 7/2014 | Kim | | G06T 3/0006 |
| | | | | 382/201 |
| 2014/0201126 A1* | 7/2014 | Zadeh | | G06K 9/627 |
| | | | | 706/52 |
| 2014/0267413 A1* | 9/2014 | Du | | G06T 13/40 |
| | | | | 345/633 |
| 2014/0275948 A1* | 9/2014 | Kamisoyama | | A61B 5/6898 |
| | | | | 600/407 |
| 2015/0043790 A1* | 2/2015 | Ono | | G06K 9/00288 |
| | | | | 382/118 |
| 2015/0157243 A1* | 6/2015 | Do | | A61B 5/1032 |
| | | | | 600/408 |
| 2015/0213303 A1* | 7/2015 | Jain | | G06K 9/00255 |
| | | | | 382/118 |
| 2015/0243056 A1* | 8/2015 | Lee | | G06T 11/005 |
| | | | | 382/131 |
| 2015/0261996 A1* | 9/2015 | Kim | | G06K 9/00255 |
| | | | | 348/14.03 |
| 2016/0148384 A1* | 5/2016 | Bud | | G06K 9/00255 |
| | | | | 348/207.11 |
| 2016/0261794 A1* | 9/2016 | Knodt | | H04N 5/23293 |
| 2016/0284354 A1* | 9/2016 | Chen | | H04N 7/147 |
| 2016/0379042 A1* | 12/2016 | Bourlai | | G06K 9/00288 |
| | | | | 382/118 |
| 2017/0185825 A1* | 6/2017 | Davis | | G06F 21/316 |
| 2018/0096212 A1* | 4/2018 | Lin | | H04N 5/23219 |
| 2018/0220952 A1* | 8/2018 | Lee | | A61B 5/6898 |

FOREIGN PATENT DOCUMENTS

| | | |
|---|---|---|
| CN | 103197825 A | 7/2013 |
| CN | 103546627 A | 1/2014 |
| EP | 2685704 A1 | 1/2014 |
| JP | 2005-27225 A | 1/2005 |
| JP | 2009-53328 A | 3/2009 |
| JP | 2009-172181 A | 8/2009 |
| JP | 2013-50927 A | 3/2013 |
| KR | 10-2005-0098543 A | 10/2005 |
| KR | 10-2006-0133607 A | 12/2006 |
| KR | 10-2007-0063195 A | 6/2007 |

(56) References Cited

FOREIGN PATENT DOCUMENTS

| | | |
|---|---|---|
| KR | 10-2009-0089535 A | 8/2009 |
| KR | 10-2011-0074264 A | 6/2011 |
| WO | 2008054162 A1 | 5/2008 |

OTHER PUBLICATIONS

International Search Report dated May 29, 2015 issued by International Searching Authority in counterpart International Patent Application No. PCT/KR2015/002535.
Communication dated Jun. 30, 2015 issued by European Patent Office in counterpart European Application No. 15159294.6.
Communication dated May 18, 2017, issued by the State Intellectual Property Office of P.R. China in counterpart Chinese application No. 201580001465.1.
Communication dated Aug. 8, 2018 issued by the State Intellectual Property Office of the People's Republic of China in Counterpart Chinese Application No. 201580001465.1.
Communication dated Nov. 2, 2018, from the State Intellectual Property Office of People's Republic of China in counterpart Application No. 201580001465.1.
Communication dated Feb. 7, 2018, issued by the State Intellectual Property Office of the People's Republic of China in counterpart Chinese Patent Application No. 201580001465.1.
Communication dated May 24, 2019, issued by the Chinese Patent Office in Counterpart Chinese Application No. 201580001465.1.

* cited by examiner

FIG. 20

| ID | FILE NAME | USER | IMAGE SIZE | ILLUMINATION | PLACE | TIME | HEART RATE | ACTIVITY AMOUNT | SLEEPING HOURS |
|---|---|---|---|---|---|---|---|---|---|
| 000a | DSC010.jpg | KIM | 100*100 | 1000 lx | HOME | 10:30 PM | 70/min | 10m/min | 7h/1day |

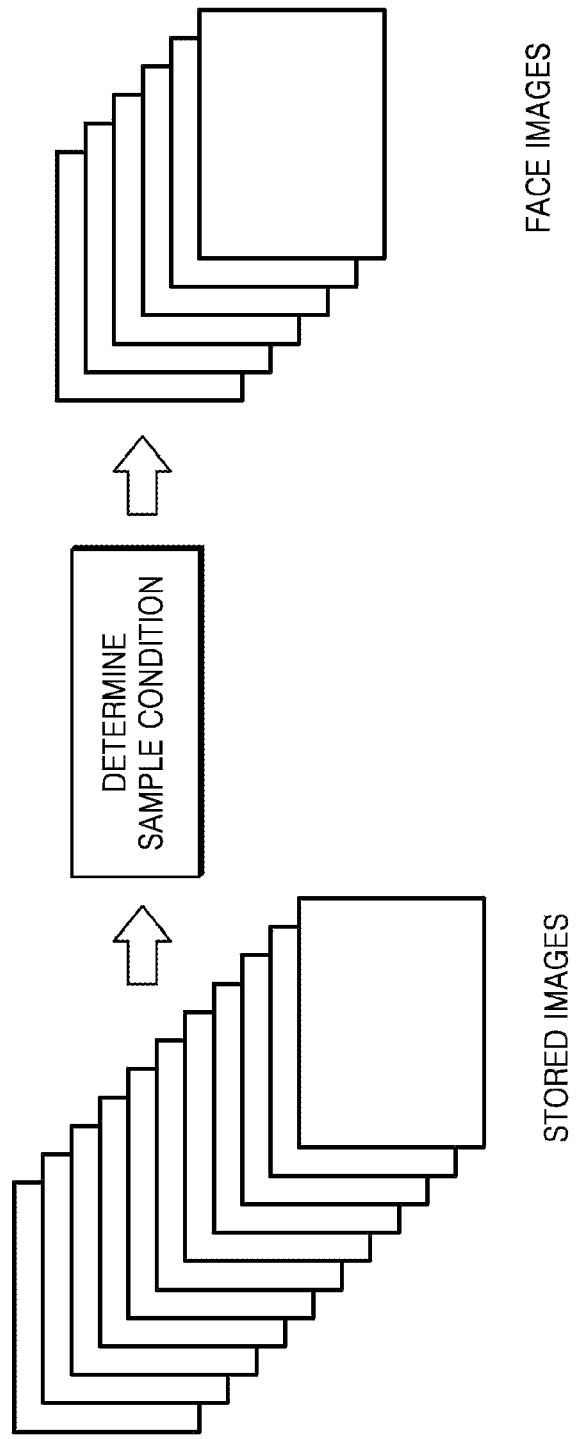

MOVING IMAGE FRAME　　　　　　FACE IMAGE

FIG. 29

| NO | NO | FILE NAME | IDENTIFIER |
|---|---|---|---|
| 1 | C:\PICTURES\GALLERY | DSC010.jpg | 000a |
| 2 | C:\PICTURES\GALLERY | DSC014.jpg | 000b |
| 3 | C:\PICTURES\GALLERY | DSC24.jpg | 000c |
| 4 | C:\PICTURES\GALLERY | DSC037.jpg | 000a |
| 5 | C:\PICTURES\GALLERY | DSC041.jpg | 000a |
| ⋮ | ⋮ | ⋮ | ⋮ |

FIG. 32B

| LIGHT SOURCE | COLOR TEMPERATURE | LIGHT SOURCE | COLOR TEMPERATURE |
|---|---|---|---|
| CANDLE LIGHT | 1900K | FLASH LIGHT | 5100~6000K |
| INCANDESCENT LIGHT | 2300K | DAYLIGHT OF DAYTIME | 5000~5500K |
| SUNRISE / SUNSET | 2000~3000K | BRIGHT MIDDAY | 6400K |
| TUNGSTEN LIGHT | 2500~3500K | CLOUDY DAY | 6500~6700K |
| FLUORESCENT LIGHT | 3500~4500K | CLOUDY DAY WITH CLOUDS | 6800~7000K |
| MORNING, EVENING OUTDOOR | 4000~4500K | CLOUDY DAY WITH FOG | 7500~8400K |

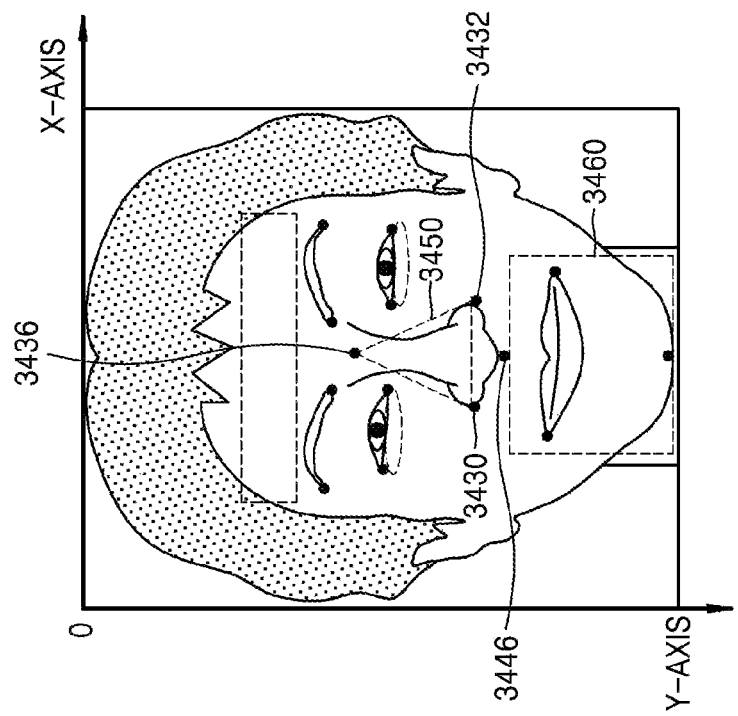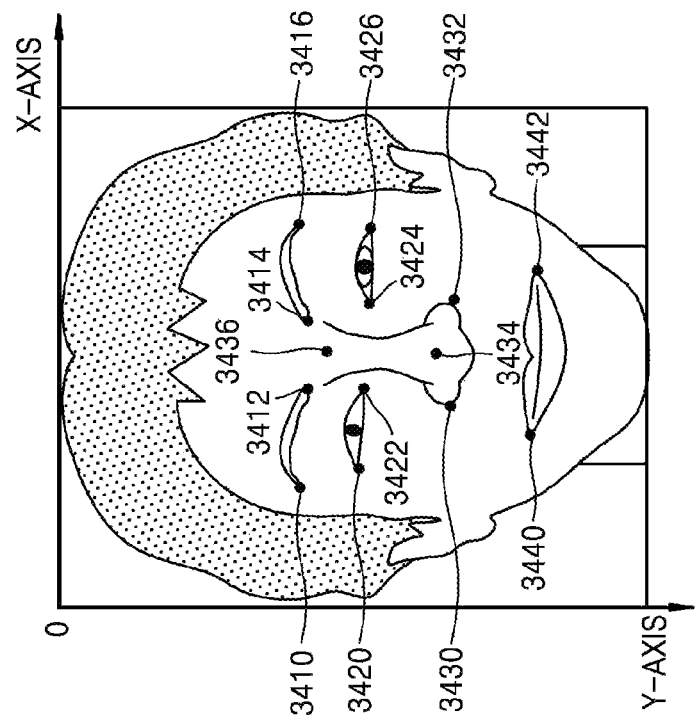

FIG. 38A

| FACE COLOR | DARK BLUE | BLACK | WHITE | RED | YELLOW |
|---|---|---|---|---|---|
| MALFUNCTIONING ORGAN | LIVER | LIVER | LUNG, RESPIRATORY ORGAN | HEART | ANEMIA, DIGESTIVE ORGAN |

FIG. 38B

| REGION | SYMPTOM | CAUSE | ACCOMPANYING SYMPTOM | TEMPORARY CAUSE |
|---|---|---|---|---|
| EYE | INFLAMED EYE | PROBLEM IN LIVER AND HEART | BENT WAIST, STIFF BACK OF NECK, BLEAR EYES, INDIGESTION | VERWORK |
|  | YELLOW EYE | LIVER, GALLBLADDER | – | – |
| BELOW EYE | YELLOW EYE | LIVER, GALLBLADDER LIVER, GALLBLADDER | – | – |
|  | YELLOW EYE | ALLERGIC RHINITIS | – | LACK OF SLEEP |
| NOSE | TWISTED NOSE | COLD BODY | BENT WAIST, STIFF BACK OF NECK, BLEAR EYES, INDIGESTION | – |
|  | RED NOSE | PROBLEM IN FEMALE HORMONE SECRETION | – | – |
| LIP | RED NOSE | LACK OF BLOOD | – | – |
|  | BLUE LIP | COLD BODY | DIGESTIVE PROBLEM, DIARRHEA | – |
|  | RED LIP | TOO MUCH HEAT IN STOMACH | STOMACH DISORDER | – |
| AROUND MOUTH | PIMPLE AROUND MOUTH | INFECTION IN MUCOUS MEMBRANE OF STOMACH | – | – |
| CHIN | PIMPLE AROUND CHIN | KIDNEY, BLADDER | – | – |

FIG. 44B

| USER ID | FEATURE INFORMATION OF FACE | REFERENCE IMAGE | FACIAL CONDITION INFORMATION | HEALTH STATUS INFORMATION |
|---|---|---|---|---|
| ID OF FIRST USER | FEATURE INFORMATION OF FACE OF FIRST USER | aaa.jpg | EXOPHTHALMOS SWOLLEN EYES | HYPERTHYREOSIS |
| ID OF SECOND USER | FEATURE INFORMATION OF FACE OF SECOND USER | bbb.jpg | DARK FACE COLOR | HEPATOCIRRHOSIS |

FIG. 56

| PHOTOGRAPHING ELEMENT | | |
|---|---|---|
| ELEMENT OTHER THAN USER | LIGHTING | BRIGHTNESS |
| | | BRIGHTNESS |
| | | COLOR TEMPERATURE |
| | PLACE | LOCATION |
| | | INDOOR / OUTDOOR |
| | BACKGROUND | COLOR |
| | | ADJACENT OBJECT |
| | BACKGROUND | SLEEPING HOURS / ACTIVITY HOURS |
| | | DAWN / MORNING / AFTERNOON / EVENING / NIGHT |
| USER | ANGLE | LEFT OR RIGHT |
| | | TOP OR BOTTOM |
| | FACIAL EXPRESSION | TOP OR BOTTOM |

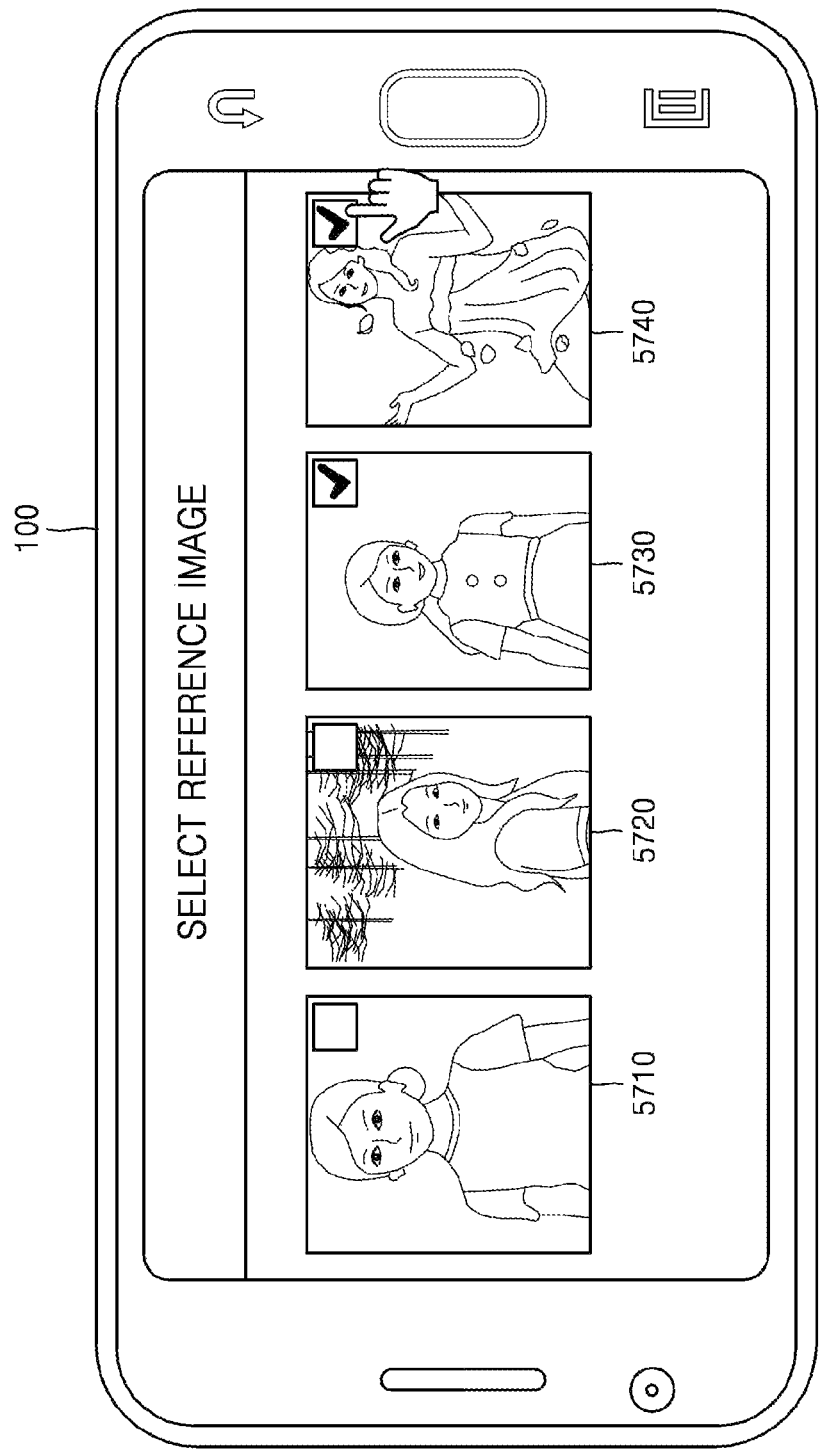

FIG. 58A
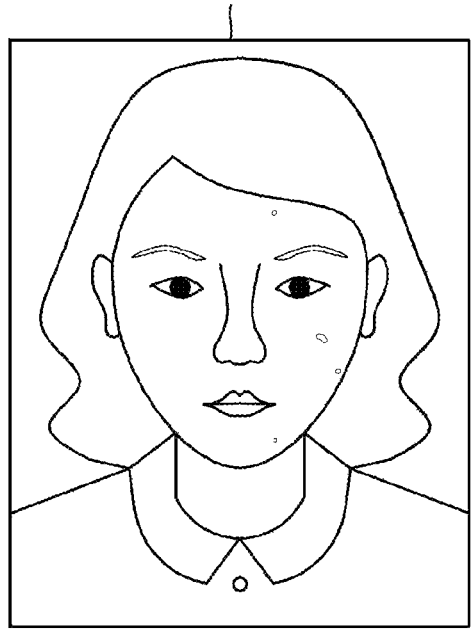 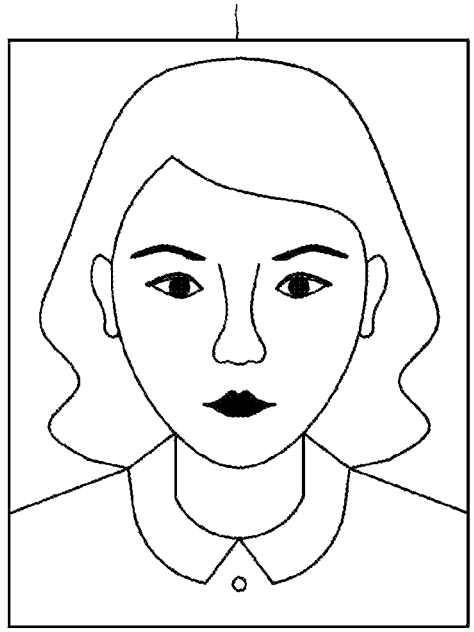
PLACE : HOME          PLACE : OFFICE

FIG. 58C
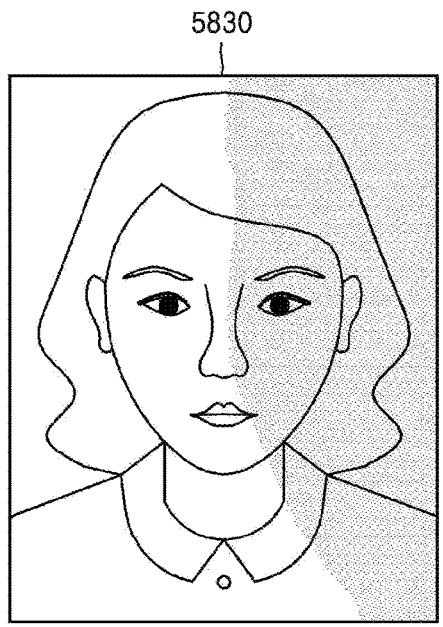
LOCATION OF LIGHTING : LEFT
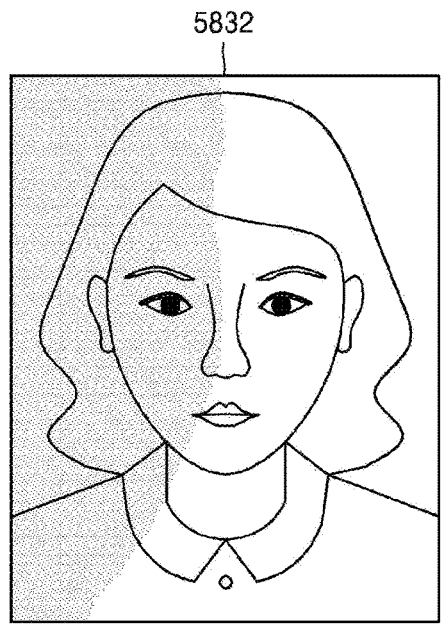
LOCATION OF LIGHTING : RIGHT
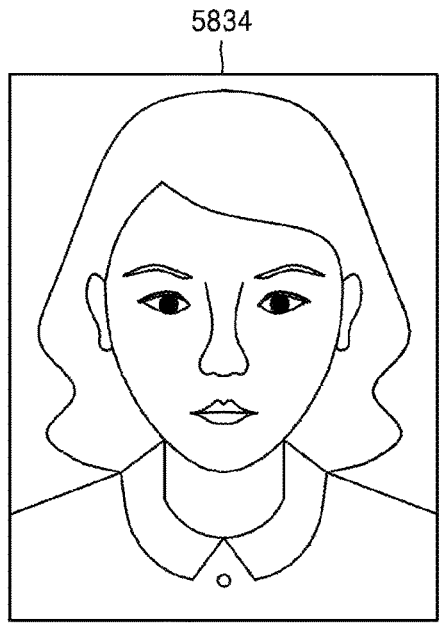
LOCATION OF LIGHTING : ABOVE LENS
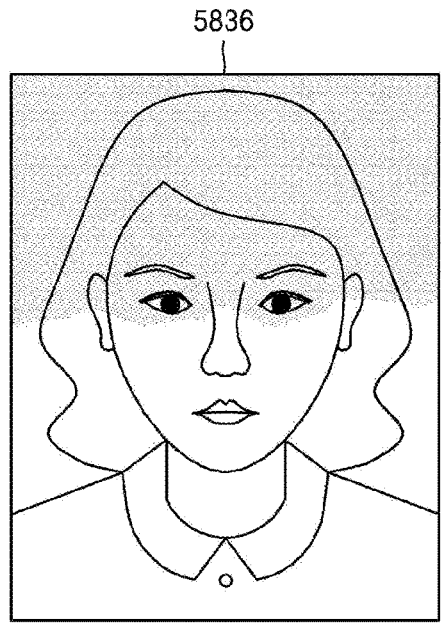
LOCATION OF LIGHTING : BELOW PERSON

6010  FACE IMAGE

6020  REFERENCE IMAGE

1) ANGLE : : YAW 25°
2) BRIGHTNESS OF LIGHTING : 200 lux
3) ANGLE OF LIGHTING : FRONT FACE
4) COLOR TEMPERATURE : 4000 K
5) INSIDE / OUTSIDE : INDOORS
6) PLACE : HOME
7) TIME : 17:33
8) FACIAL EXPRESSION : EXPRESSIONLESS 1) ANGLE : YAW 15 TO 30°
2) BRIGHTNESS OF LIGHTING : 150-200 lux

FIG. 62

| REGION | SYMPTOM (6220) | SYMPTOM (6230) | ACCOMPANYING SYMPTOM | PRESCRIPTION |
|---|---|---|---|---|
| EYE | INFLAMED EYE | PIMPLE AROUND CHIN | DIZZINESS, HEADACHE, COLD SORE IN MOUTH TINNITUS, DANDRUFF | STOMACH DISORDER EXERCISE REGULARLY |
| | YELLOW EYE | LIVER, GALLBLADDER | – | REFRAIN FROM INSTANT FOOD, CHOLECYSTOTOMY |
| BELOW EYE | BLACK LINE | PROBLEM IN SPLEEN, STOMACH, AND KIDNEY | – | EAT CHESTNUT AND SEAWEEDS |
| | DARK CIRCLE | STOMACH, AND KIDNEY | – | REFRAIN FROM SMOKING, REFRAIN FROM INSTANT FOOD |
| NOSE | TWISTED NOSE | COLD BODY | BENT WAIST, STIFF BACK OF NECK, BLEAR EYES, INDIGESTION | EXERCISE REGULARLY |
| | RED NOSE | PROBLEM IN FEMALE HORMONE SECRETION | – | REFRAIN FROM STRONG-TASTING FOOD |
| LIP | RED NOSE | LACK OF BLOOD | – | REDUCE STRESS, GET ENOUGH REST |
| | RED NOSE | COLD BODY | DIGESTIVE PROBLEM, DIARRHEA | EXERCISE REGULARLY, EAT REGULARLY |
| | RED NOSE | TOO MUCH HEAT IN STOMACH | STOMACH DISORDER | EAT REGULARLY, EAT YAM AND CABBAGE |
| AROUND MOUTH | PIMPLE AROUND MOUTH | INFECTION IN MUCOUS MEMBRANE OF STOMACH | – | EAT YAM AND CABBAGE |
| CHIN | PIMPLE AROUND CHIN | KIDNEY, BLADDER | – | DRINK WATER AND EAT CRANBERRY |

ELECTRONIC APPARATUS FOR PROVIDING HEALTH STATUS INFORMATION, METHOD OF CONTROLLING THE SAME, AND COMPUTER-READABLE STORAGE MEDIUM

CROSS-REFERENCE TO RELATED APPLICATIONS

This application claims priority from Korean Patent Application No. 10-2014-0030457, filed on Mar. 14, 2014 in the Korean Intellectual Property Office (KIPO), and Korean Patent Application No. 10-2014-0098639, filed on Jul. 31, 2014, in the KIPO, the disclosures of which are incorporated herein in their entireties by reference.

BACKGROUND

1. Field

Apparatuses and methods consistent with exemplary embodiments relate to an electronic apparatus for providing health status information, a method of controlling the same, and a computer-readable recording medium having recorded thereon computer program codes for performing the method.

2. Description of the Related Art

Recently, various electronic apparatuses provide health-related functions to users. For these apparatuses, various equipment is used to measure health-related information. In particular, special apparatuses are used to measure health-related information, for example, to photograph a subject by using ultrasonic waves, computer tomography (CT), or magnetic resonance imaging (MRI), to measure blood pressure by using a blood pressure gauge, or to measure a weight by using a scale. However, since it is difficult for ordinary users to easily use such special apparatuses, the ordinary users may have difficulty in obtaining heath status information.

A technology of detecting a face region from an image obtained by capturing a face of a user, and identifying the detected face region is being developed.

Accordingly, health status information may be provided to the user without having to use a special apparatus if a health status of the user can be determined based on the image.

SUMMARY

Aspects of one or more exemplary embodiments provide health status information to a user by using a face image, and enable the user to easily obtain the health status information.

Aspects of one or more exemplary embodiments provide health status information obtainable by easily collecting face images.

Aspects of one or more exemplary embodiments provide a change of health status information over time to a user.

Additional aspects will be set forth in part in the description which follows and, in part, will be apparent from the description, or may be learned by practice of exemplary embodiments.

According to an aspect of an exemplary embodiment, there is provided a device including: a storage configured to store a first image including a face of a user and first health status information extracted from the first image; an imager configured to capture an image; a controller configured to control the imager to capture a second image including the face of the user and to extract second health status information from the captured second image; and a display configured to output the second image and information other than the stored first health status information from among the extracted second health status information.

From among a plurality of applications in the device, when a first application which captures an image by using the imager is executed, the controller may be configured to control the imager to capture the second image, and when a second application that is different from the first application is executed, the controller may be configured to control the display to output the second image and the information other than the first health status information from among the extracted second health status information.

The device may further include: a user interface unit configured to receive a user input for unlocking the device when in a locked state, wherein the controller may be configured, when the user input for unlocking the device in the locked state is received, to control the imager to capture the second image and to extract the second health status information from the captured second image.

The device may further include: a user interface unit configured to receive a user input for executing a video call application in the device, wherein the controller may be configured to, when the video call application is executed according to the received user input, control the imager to capture the second image, and to extract the second health status information from the captured second image.

The first image may be a photograph that is received from a server in which the user is registered.

The controller may be configured to normalize a resolution of the face of the user in the captured second image by expanding or reducing a size of the second image to a pre-set size, and to extract the second health status information from the normalized second image.

The controller may be configured to obtain a color temperature of illumination on the face of the user at a point of time when the second image is captured, to normalize a hue value of the face of the user by adjusting a hue value of the second image based on the obtained color temperature, and to extract the second health status information from the normalized second image.

The display may be configured to output the second image by displaying an indicator on a face region of the user in the second image, from which the information other than the first health status information is extracted, to indicate that the information other than the first health status information is extracted.

The display may be configured to output, in chronological order, a plurality of second images that are captured during a predetermined time period and health status information extracted from the plurality of second images.

The display may be configured to output photographing guide information for guiding capturing of the face of the user based on a pre-set face image obtaining condition; and the controller may be configured to determine whether the imager captured the face of the user according to the pre-set face image obtaining condition, and to determine, when it is determined that the face of the user is captured according to the pre-set face image obtaining condition, an image of the face of the user as the second image.

The device may further include: a sensor configured to obtain bio-information of the user at a point of time when the second image is captured, wherein the controller may be configured to determine a biological condition of the user at the point of time when the second image is captured based on the obtained bio-information, and to exclude some of the second facial condition information, which is shown on the face of the user due to the biological condition.

According to an aspect of another exemplary embodiment, there is provided a method of providing health status information, by a device, the method including: obtaining first health status information extracted from a first image including a face of the user; capturing a second image including the face of the user; extracting second health status information from the captured second image; and outputting the second image and information other than the first health status information from among the extracted second health status information.

The capturing the second image may include, from among a plurality of applications in the device, when a first application which captures an image by using an imager is executed, capturing the second image; and the outputting the second image and the information may include, from among the plurality of applications in the device, when a second application that is different from the first application is executed, outputting the second image and the information other than the first health status information from among the second health status information.

The method may further include: receiving a user input for unlocking the device when in a locked state, wherein the capturing the second image may include, when the user input is received, capturing the second image.

The method may further include: receiving a user input for executing a video call application in the device, wherein the capturing the second image may include, when the user input is received, capturing the second image.

The first image may be a photograph that is received from a server in which the user is registered.

The extracting the second health status information may include: normalizing a resolution of the face of the user in the second image by expanding or reducing a size of the second image to a pre-set size; and extracting the second health status information from the normalized second image.

The extracting the second health status information may include: obtaining a color temperature of illumination on the face of the user at a point of time when the second image is captured; normalizing a hue value of the face of the user by adjusting a hue value of the second image based on the obtained color temperature; and extracting the second health status information from the normalized second image.

The outputting the second image and the information may include outputting the second image by displaying an indicator on a face region of the user in the second image, from which the information other than the first health status information is extracted, to indicate that the information other than the first health status information is extracted.

The outputting the second image and the information may include outputting, in chronological order, a plurality of the second images that are captured during a predetermined time period and health status information extracted from the plurality of second images.

The capturing the second image may include: outputting photographing guide information for guiding capturing of the face of the user based on a pre-set face image obtaining condition; determining whether an imager captured the face of the user according to the pre-set face image obtaining condition; and when it is determined that the face of the user is captured according to the pre-set face image obtaining condition, determining an image of the face of the user as the second image.

The method may further include: detecting bio-information of the user at a point of time when the second image is captured, wherein the extracting the second health status information may include: determining a biological condition of the user at the point of time when the second image is captured based on the detected bio-information; and excluding some of the second facial condition information, which is shown on the face of the user due to the biological condition.

According to an aspect of another exemplary embodiment, there is provided a non-transitory computer-readable recording medium having recorded thereon a program executable by a computer for performing the method.

According to an aspect of another exemplary embodiment, there is provided a device including: a controller configured to obtain a second image including the face of the user and to extract second health status information from the obtained second image; and an output device configured to output the second image and information other than first health status information, obtained from a first image including the face of the user, from among the extracted second health status information.

The device may further include: an imager configured to capture an image, wherein the controller is configured to control the imager to capture the second image including the face of the user and to extract second health status information from the captured second image.

From among a plurality of applications in the device, when a first application which captures an image by using the imager is executed, the controller may be configured to control the imager to capture the second image, and when a second application that is different from the first application is executed, the controller may be configured to control the output device to output the second image and the information other than the first health status information from among the extracted second health status information.

The device may further include: a user interface unit configured to receive a user input for unlocking the device when in a locked state, wherein the controller may be configured, when the user input for unlocking the device in the locked state is received, to control the imager to capture the second image and to extract the second health status information from the captured second image.

The device may further include a user interface unit configured to receive a user input for executing a video call application in the device, wherein the controller may be configured to, when the video call application is executed according to the received user input, control the imager to capture the second image, and to extract the second health status information from the captured second image.

The first image may be a photograph that is received from a server in which the user is registered.

The controller may be configured to normalize a resolution of the face of the user in the obtained second image by expanding or reducing a size of the second image to a pre-set size, and to extract the second health status information from the normalized second image.

The controller may be configured to obtain a color temperature of illumination on the face of the user at a point of time when the second image is captured, to normalize a hue value of the face of the user by adjusting a hue value of the second image based on the obtained color temperature, and to extract the second health status information from the normalized second image.

The output device may be configured to output the second image by displaying an indicator on a face region of the user in the second image, from which the information other than the first health status information is extracted, to indicate that the information other than the first health status information is extracted.

The output device may be configured to output, in chronological order, a plurality of second images that are captured or obtained during a predetermined time period and health status information extracted from the plurality of second images.

The output device may be configured to output photographing guide information for guiding capturing of the face of the user based on a pre-set face image obtaining condition; and the controller may be configured to determine whether the imager captured the face of the user according to the pre-set face image obtaining condition, and to determine, when it is determined that the face of the user is captured according to the pre-set face image obtaining condition, an image of the face of the user as the second image.

The device may further include a sensor configured to obtain bio-information of the user at a point of time when the second image is captured, wherein the controller may be configured to determine a biological condition of the user at the point of time when the second image is captured based on the obtained bio-information, and to exclude some of the second facial condition information, which is shown on the face of the user due to the biological condition.

BRIEF DESCRIPTION OF THE DRAWINGS

These and/or other aspects will become apparent and more readily appreciated from the following description of exemplary embodiments, taken in conjunction with the accompanying drawings in which:

FIG. 20 is a table for describing photographing circumstance information obtained while obtaining a face image by a device by using an imaging unit, according to an exemplary embodiment;

FIG. 24 is a diagram for describing a process of obtaining, by a device, a face image from images stored in the device, according to an exemplary embodiment;

FIG. 29 is a table for describing a method of storing, by a device, a face image, according to an exemplary embodiment;

FIGS. 32A through 32C are diagrams for describing a method of adjusting, by a device, an effect of a color temperature of illumination on a face image, according to an exemplary embodiment;

FIGS. 35A and 35B are diagrams for describing a method of determining, by a device, a location of a diagnosis region, according to an exemplary embodiment;

FIGS. 38A and 38B are tables for describing a method of extracting, by a device, health status information of a user based on facial condition information extracted from a face image, according to an exemplary embodiment;

FIG. 44B illustrates a database about users, which is stored in a service server, according to an exemplary embodiment;

FIG. 56 is a table of photographing elements according to an exemplary embodiment;

FIG. 57 is a diagram for describing a method of determining, by a device, a reference image, according to an exemplary embodiment;

FIGS. 58A through 58C are diagrams for describing a method of determining, by a device, a reference image, according to one or more exemplary embodiments;

FIG. 62 is a database of health status information extractable from facial condition information and prescription information according to the health status information, according to an exemplary embodiment;

DETAILED DESCRIPTION

Figure 1:
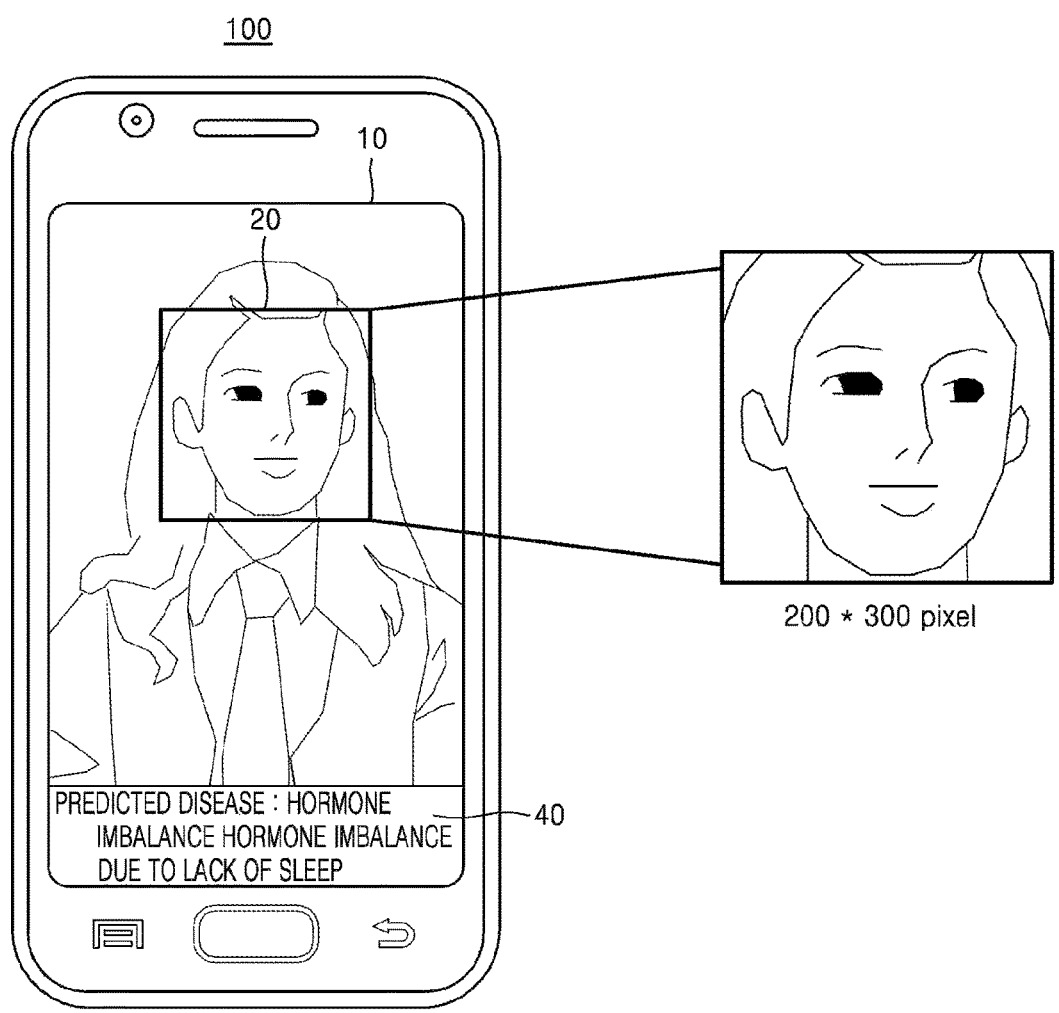
FIG. 1 is a diagram for describing a method of extracting health status information of a user from a face image including a face of the user, according to an exemplary embodiment.

Advantages and features of one or more exemplary embodiments and methods of accomplishing the same may be understood more readily by reference to the following detailed description of exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present embodiments to one of ordinary skill in the art, and the present invention will only be defined by the appended claims. Like reference numerals refer to like elements throughout the specification.

Hereinafter, the terms used in the specification will be briefly defined, and the embodiments will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of exemplary embodiments. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

As used herein, the term "and/or" includes any and all combinations of one or more of the associated listed items. Expressions such as "at least one of," when preceding a list of elements, modify the entire list of elements and do not modify the individual elements of the list.

Throughout the specification, facial condition information may denote a state of a reference face for determining health information. The facial condition information may include a facial color, numbers and sizes of blemishes and pimples, inflamed eyes, an eye color, sizes of pupils, movements of pupils, a face size, a shape of a face contour, a lip color, a cracked lip, locations of facial organs, such as eyes, a nose, a lip, ears, and eyebrows, a hair color, a hair condition, and movements of facial muscles. Throughout the specification, a "face image obtaining condition" may mean a condition satisfied by a face region in an input image for a device to extract facial condition information from the face region in the input image.

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the embodiments with unnecessary detail.

FIG. 1 is a diagram for describing a method of extracting health status information 40 of a user from a face image 20 including a face of the user, according to an exemplary embodiment.

Referring to FIG. 1, a device 100 may obtain the face image 20 from an input image 10. The input image 10 may be an image obtained via general photographing of a user. Alternatively, the input image 10 may be an image received from an external device, may be an image obtained by capturing a template (for example, unlocking face recognition) to capture a face, etc.

The device 100 may obtain the face image 20 from the input image 10 that satisfies a pre-set (e.g., predetermined) face image obtaining condition. The pre-set face image obtaining condition may include at least one of a condition about whether a face is detected, a condition about a face direction, a condition about illumination during photographing, a condition about shaking during photographing, a condition about whether eyes are opened, a condition about a facial expression, a condition about whether ears are viewable, a condition about whether a face is at the center, and a condition about a face size.

The face image 20 may mean an image including only (or including substantially) a face region from an entire region of the input image 10. For example, the face image 20 may be a rectangular region having a region from a forehead to a chin as a vertical region and a region between two ears as a horizontal region from among a face of a subject in the input image 10. According to another exemplary embodiment, the face image 20 may be a rectangular region having a region from a predetermined distance from a forehead to a predetermined distance from a chin as a vertical region and a region from a predetermined distance from one ear to a predetermined distance from another ear as a horizontal region from among a face of a subject in the input image 10.

The device 100 may detect the face region from the input image 10 and store an image of the face region as the face image 20. One or more exemplary embodiments of the device 100 obtaining the input image 10 and obtaining the face image 20 from the input image 10 will be described in detail below with reference to FIGS. 8 through 29.

Upon obtaining the face image 20, the device 100 may normalize the face image 20 in or according to a pre-set standard. For example, the device 100 may change a size of the face image 20 to a pre-set size. Alternatively, the device 100 may adjust an effect of a color temperature of illumination on the face image 20, may change brightness of the face image 20 to pre-set brightness, etc. One or more exemplary embodiments of the device 100 normalizing the face image 20 based on a pre-set standard will be described in detail below with reference to FIGS. 30 through 32E.

Upon normalizing the face image 20, the device 100 may extract facial condition information from the face image 20. One or more exemplary embodiments of the device 100 extracting the facial condition information from the face image 20 will be described in detail below with reference to FIGS. 33 through 36.

Upon obtaining the facial condition information, the device 100 may obtain the health status information 40 indicating a health status of the user by using the facial condition information. One or more exemplary embodiments of the device 100 obtaining the health status information 40 by using the facial condition information will be described in detail below with reference to FIGS. 37 through 44.

Also, the device 100 may provide the health status information 40 to the user according to any of various methods. One or more exemplary embodiments of the device 100 providing the health status information 40 will be described in detail below with reference to FIGS. 45 through 54.

Figure 2:
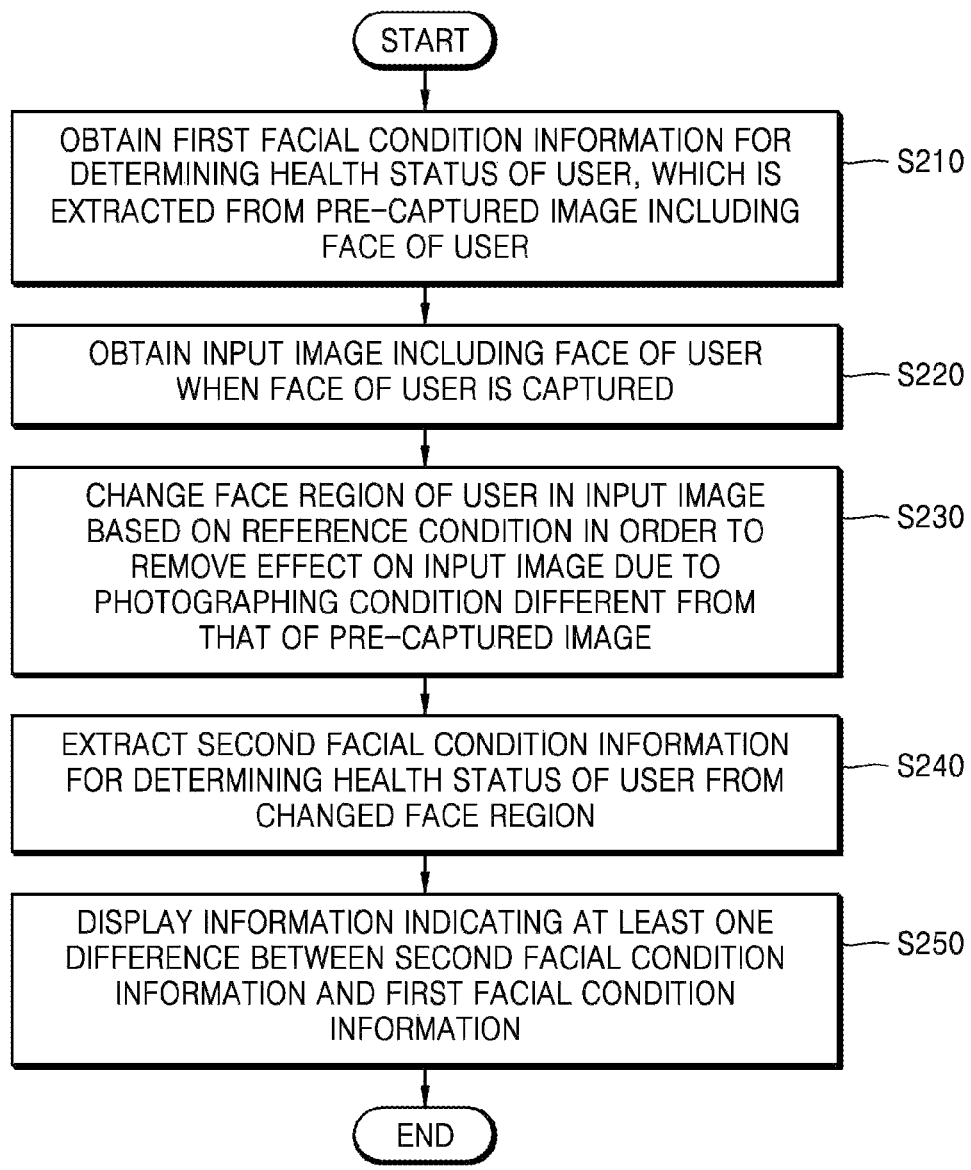
FIG. 2 is a flowchart of a method of obtaining, by a device, health status information of a user, based on a face image of the user, according to an exemplary embodiment.

FIG. 2 is a flowchart of a method of obtaining, by the device 100, health status information of a user, based on a face image of the user, according to an exemplary embodiment.

In operation S210, the device 100 may obtain first facial condition information for determining a health status of a user, which is extracted from a pre-captured and/or pre-stored image including a face of the user.

The pre-captured image may be a plurality of images that are captured before a point of time when an input image is captured. The first facial condition information extracted from the pre-captured image may be stored in the device 100

Facial condition information may be about a status of a reference face for determining health information. Facial condition information may be determined according to one input image.

In operation S220, the device 100 may obtain the input image including the face of the user, when the face of the user is captured.

For example, the device 100 may obtain the input image via general photographing of the user. Alternatively, the device 100 may obtain the input image from an external device.

Alternatively, for example, the device 100 may obtain the input image by capturing a template (for example, unlocking face recognition) to capture a face. While capturing a template, the device 100 may display photographing guide information for guiding capturing of a face of a user, according to a pre-set face image obtaining condition.

Upon obtaining the input image, the device 100 may determine whether the input image satisfies the pre-set face image obtaining condition. For example, the device 100 may determine whether illumination while capturing the input image is within a base range. Alternatively, the device 100 may determine whether a camera was shaken when the input image is captured.

Also, the device 100 may determine whether a face in a face region of the input image satisfies the pre-set face image obtaining condition. For example, the device 100 may determine whether an angle of the face is within a base angle from a front face. Alternatively, the device 100 may determine whether eyes of the face are opened, a facial expression of the face in the input image, whether ears of the face are shown in the input image, whether the face in the input image has at least a base size, etc.

The device 100 may use the input image only when the input image satisfies the pre-set face image obtaining condition. In operation S230, the device 100 may change the face region of the user in the input image based on a reference condition in order to remove an effect on the input image due to a photographing condition different from that of the pre-captured image.

For example, the device 100 may normalize resolution of the face of the user in the input image by expanding or reducing a size of the face region to a pre-set size. Alternatively the device 100 may exclude an effect of a color temperature of illumination from the input image. For example, a color temperature of illumination on the face of the user at a point of time when the input image is captured is obtained. Based on the color temperature, a hue value of the face of the user in the input image may be normalized by adjusting a hue value of the face region of the user in the input image. Alternatively, the device 100 may normalize the hue value of the face of the user by adjusting the hue value of the face region such that a color of a base region of the face region is changed to a base color, or may normalize brightness of the face of the user in the input image by changing brightness of the face region to pre-set brightness.

As such, even when there are a plurality of images captured under different photographing conditions, the device 100 may normalize faces of users in the plurality of images so as to provide an effect whereby the faces appear to have been captured under the same photographing condition.

Accordingly, the device 100 may extract facial condition information for determining a health status of the user from images captured under the same photographing condition.

In operation S240, the device 100 may extract second facial condition information for determining the health status of the user from the changed face region.

By normalizing the face region of the user in the input image, the device 100 may extract the second facial condition information from the normalized face region.

For example, the device 100 may determine whether a region under an eye is swollen. Alternatively, the device 100 may determine whether a color of the region under the eye is darker than before.

In operation S250, the device 100 may display information indicating at least one difference between the second facial condition information and the first facial condition information.

For example, when the first facial condition information is information that the region under the eye is swollen, and the second facial condition information is information that the region under the eye is swollen and is black, the device 100 may display information that the region under the eye is black from the second facial condition information on a screen. As such the device 100 may notify the user about a recent change compared to a previous status of the user.

Alternatively, the first facial condition information extracted from the pre-captured image may be a face shape feature of the user instead of information shown on the face due to a disease, may be information that is always known by the user due to a chronic disease, etc.

The device 100 may display (e.g., display only) the information indicating the at least one difference so as to provide (e.g., provide only) information about a recent disease or a recently deteriorated organ to the user.

Also, the device 100 may display the information indicating the at least one difference on a region where the at least one difference is extracted. For example, when the at least one difference is a lip color, the device 100 may display on a lip of the input image information about a disease or disorder of the lip.

Also, the device 100 may obtain health status information indicating a health status of the user, which is different at a point of time when the input image is captured compared to a point of time when the pre-captured image was captured, based on the information indicating the at least one difference.

The health status information may include information about a disease of the user predicted or determined from facial condition information, an organ having a deteriorated function, or a condition of the user.

For example, when it is determined that the region under the eye is swollen, the device 100 may determine that the user has a hyperthyroidism or an allergic disease. Also, when it is determined that the region under the eye is black, the device 100 may determine that the user has an allergic rhinitis.

The device 100 may obtain health status information of the user based on the second facial condition information.

The device 100 may obtain the health status information while considering bio-information of the user obtained while capturing the input image, in addition to the facial condition information. For example, the device 100 may determine a biological condition of the user at the point of time when the input image is captured based on the bio-information of the user, and obtain the health status information by considering the bio-information while excluding information shown on the face of the user due to the biological condition from the second facial condition information.

At this time, the device 100 may display a user interface for selecting at least one of a plurality of the bio-information. Upon receiving a user input of selecting the bio-information, the device 100 may obtain the health status information while considering the second facial condition information and the bio-information.

The device 100 may display the health status information on a screen in any of various methods.

For example, the device 100 may display the health status information of the user changing over time, based on the first facial condition information and the second facial condition information.

For example, the device 100 may display the face region and the health status information corresponding to the face region together. In this case, the device 100 may display, on a region of the face region from which the facial condition information is extracted, an image indicating that the region is related to the health status information.

Alternatively, when a plurality of face regions are displayed, the device 100 may display the plurality of face regions and the health status information corresponding to the plurality of face regions according to an order of captured dates and times.

Also, the device 100 may display a user interface for selecting at least one disease obtained or determined based on the second facial condition information from the plurality of face regions. Upon receiving a user input of selecting the at least one disease, the device 100 may display images related to the selected disease from among the plurality of face regions according to an order of captured dates and times.

Also, the device 100 may display a calendar showing dates and days of the week of a certain period. Also, the device 100 may display the health status information obtained from the second facial condition information extracted from a face region captured on a certain date from among the plurality of face regions, on a region corresponding to the certain date in the calendar.

Figure 3:
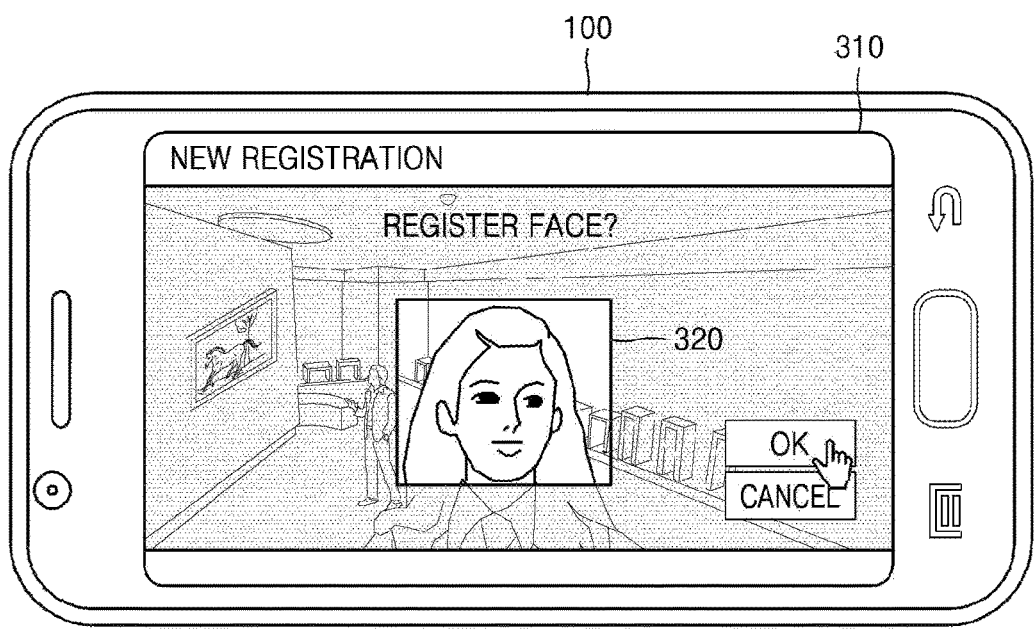
FIG. 3 is a diagram for describing a method of registering a face of a user, according to an exemplary embodiment.

FIG. 3 is a diagram for describing a method of registering a face of a user, according to an exemplary embodiment.

Referring to FIG. 3, the device 100 may provide a user face registration interface 310 for capturing a face image of a user and registering the captured face image as the face of the user.

The user face recognition interface 310 may include an interface for capturing the face image in any one of various directions, for example, a front face and a side face of the user.

Also, the user face registration interface 310 may include a guide image 320 for capturing the face image according to a pre-set size.

Upon receiving a user input for registering the captured face image, the device 100 may store the captured face image according to identification (ID) information of the user. Upon registering the face image, the device 100 may extract features of the face based on the registered face image. The device 100 may store the extracted features according to the ID information of the user. Accordingly, the device 100 may extract features of a face from an arbitrary image, determine similarity between the extracted features and the features stored in the device 100, and determine that the face in the arbitrary image is the face of the user when the similarity is equal to or higher than a threshold value.

According to one or more exemplary embodiments, the device 100 may register the face of the user based on an image selected by the user from among images stored in the device 100.

Figure 4:
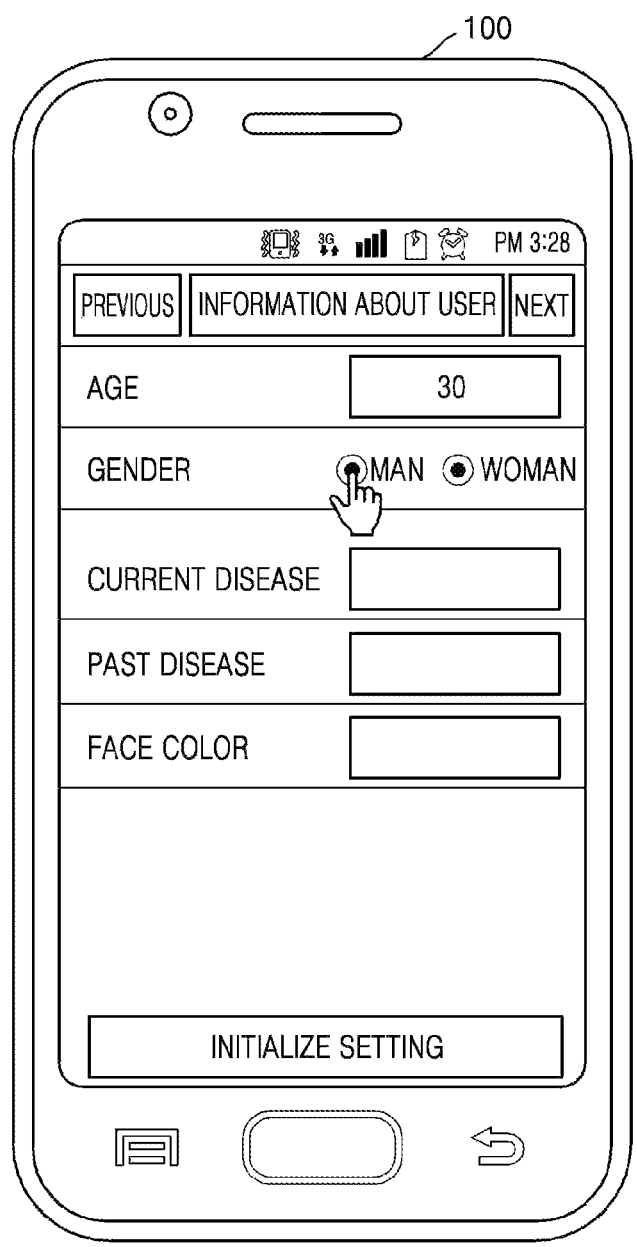
FIG. 4 is a diagram for describing a method of registering information about a user, according to an exemplary embodiment.

FIG. 4 is a diagram for describing a method of registering information about a user, according to an exemplary embodiment.

Referring to FIG. 4, the device 100 may provide an interface for registering information about a user.

The information may include biological information of the user and information about a medical history of the user. For example, the information may include at least one of an age, a weight, a height, a gender, a current disease, a past disease, a face color of the user, etc.

The device 100 may receive the information from the user. Also, the device 100 may store the information according to ID information of the user. The device 100 may accurately obtain a health status of the user from facial condition information of the user by considering the information.

Figure 5:
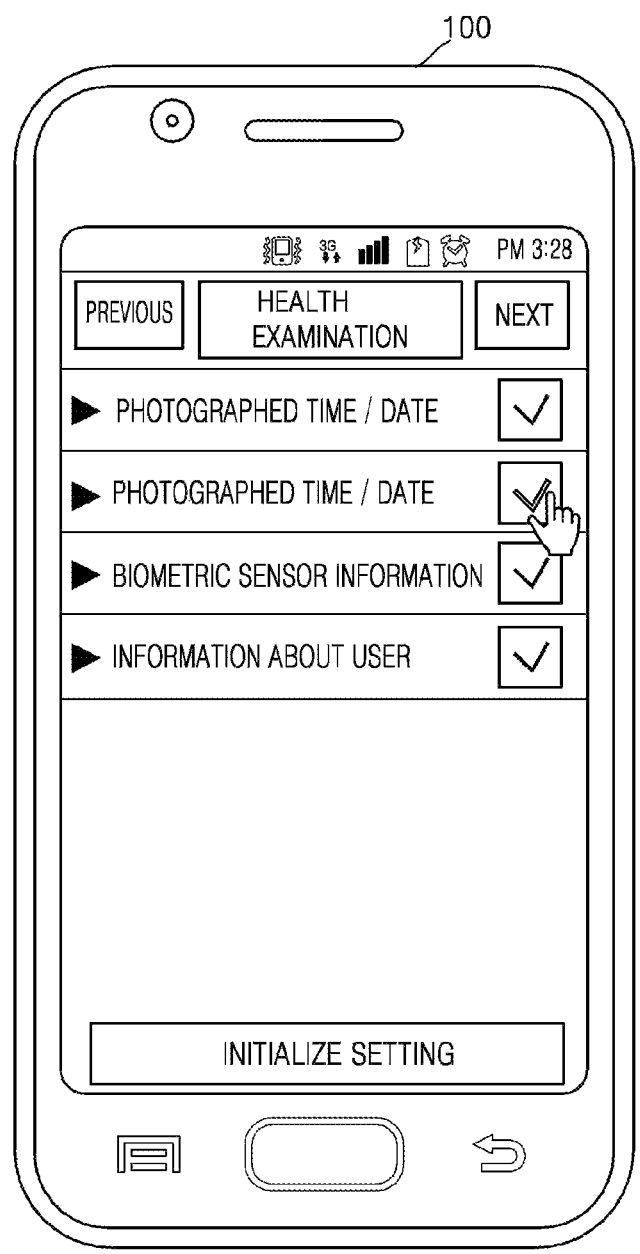
FIG. 5 is a diagram for describing a method of setting, by a device, information to be considered during a health examination, based on selection of a user, according to an exemplary embodiment.

FIG. 5 is a diagram for describing a method of setting, by the device 100, information to be considered during a health examination, based on selection of a user, according to an exemplary embodiment.

Referring to FIG. 5, the device 100 may provide a user interface for selecting information to be considered during a health examination.

The information to be considered during the health examination may include at least one of a photographed time, a photographed date, a photographed place, bio-information, information about the user, etc. The bio-information may include at least one of a heart rate, a blood pressure, sleeping hours, brain waves, etc. The bio-information may be obtained from a sensor included in the device 100. Alternatively, the bio-information may be recorded in an input image in a form of metadata.

By selecting the information to be considered during the health examination, the device 100 may obtain health status information from facial condition information of the user while considering the selected information.

Figure 6:
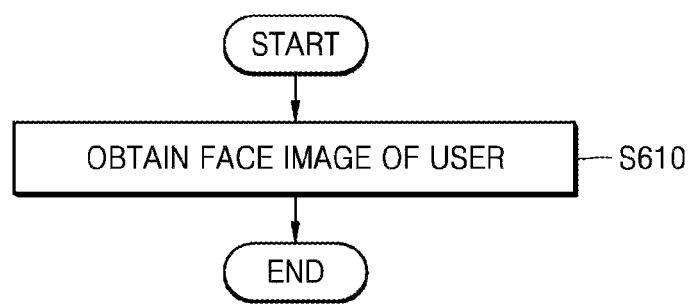
FIG. 6 is a flowchart of a method of obtaining, by a device, a face image, according to an exemplary embodiment.

FIG. 6 is a flowchart of a method of obtaining, by the device 100, a face image, according to an exemplary embodiment.

In operation S610, the device 100 may obtain a face image of a user.

The device 100 may obtain an input image. Upon obtaining the input image, the device 100 may detect a face region in the input image. Upon detecting the face region, the device 100 may determine whether the face region satisfies a face image obtaining condition. When the face region satisfies the face image obtaining condition, the device 100 may store the face region as the face image.

Figure 7:
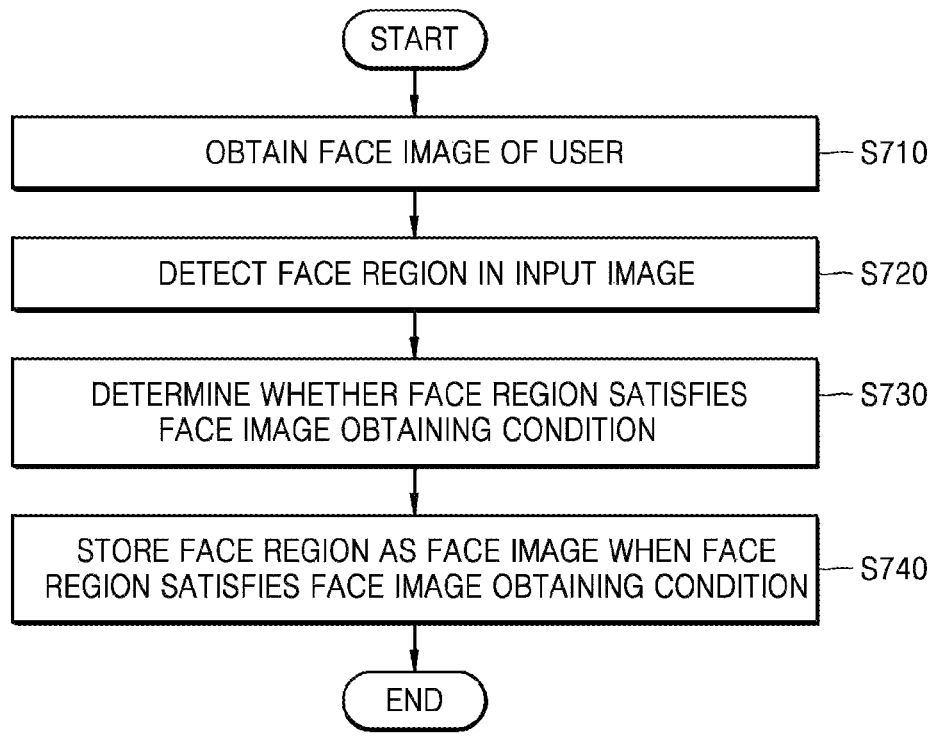
FIG. 7 is a flowchart of a method of obtaining, by a device, a face image from an input image, according to an exemplary embodiment.

FIG. 7 is a flowchart of a method of obtaining, by the device 100, a face image from an input image, according to an exemplary embodiment.

In operation S710, the device 100 may obtain an input image.

The device 100 may obtain the input image in any of various methods.

For example, the device 100 may receive the input image including a face of a user from an imaging unit (e.g., imager, camera, etc.) included in the device 100. In this case, the device 100 may provide a template capturing interface for obtaining the input image satisfying a pre-set face image obtaining condition. One or more exemplary embodiments for capturing of a template will be described in detail below with reference to FIGS. 8 through 14.

Also, when the device 100 satisfies a condition of capturing the face of the user, the device 100 may capture the face without a user input. One or more exemplary embodiments for the capturing of the face will be described in detail below with reference to FIGS. 15 through 19.

Alternatively, the device 100 may obtain, as the input image, an image selected by a user from among a plurality of images stored in the device 100. One or more exemplary embodiments for the selecting of the image will be described in detail below with reference to FIGS. 21 through 25. Alternatively, the device 100 may obtain an image downloaded from an external device as the input image. One or more exemplary embodiments for the obtaining of the downloaded image will be described in detail below with reference to FIG. 22.

In operation S720, the device 100 may detect a face region in the input image.

The device 100 may detect the face region in the input image according to any of various algorithms. For example, the device 100 may determine a location of the face region in the input image based on a knowledge-based method, a feature-based method, a template-matching method, or an appearance-based method.

In operation S730, the device 100 may determine whether the face region satisfies a face image obtaining condition.

The face image obtaining condition may be a condition that is satisfied by the face region in the input image for the device 100 to extract facial condition information from the face region. The face image obtaining condition may be a combination of various standards, such as a condition of whether a face is detected, a condition about a face direction, a condition about illumination during photographing, a condition about shaking during photographing, a condition of whether eyes are opened, a condition about a facial expression, a condition about whether ears are shown, a condition about whether a face is at the center, a condition about a face size, and a condition about a focus range.

The condition about whether a face is detected is a condition in which when a face is detected from the input image, the input image is selected as the face image, and when a face is not detected, the input image is not used as the face image. In order to detect the face image from the input image, the device 100 may use any of various face detecting algorithms, such as an adaboost algorithm.

The condition about a face direction is a condition in which when a face in a certain direction is detected from the input image, the input image is selected as the face image. For example, when an image of a front of a face is used, the device 100 selects the input image as the face image when a front of the face is detected from the input image. Alternatively, when an image of a side of a face is used, the device 100 selects the input image as the face image when a side of the face is detected from the input image.

The condition about illumination during photographing may be a condition in which illumination during photographing is between first illumination and second illumination. When the input image does not satisfy the condition about illumination, the device 100 may not select the input image as the face image. The illumination during photographing may be measured by using an illumination sensor included in the device 100. When the input image is stored in the device 100, the device 100 may use an illumination condition stored in an image file of the input image.

The condition about shaking during photographing is a condition in which the input image is not selected as the face image when the input image is shaken at least a certain (e.g., predetermined or threshold) level. According to an exemplary embodiment, the shaking during photographing may be measured by using a shaking sensor. According to another exemplary embodiment, the shaking during photographing may be determined based on a shaking level of the input image.

The condition whether eyes are opened is a condition in which the input image is not selected as the face image when a face is detected from the input image but eyes are closed. For example, eyes may be detected from the input image, black and white regions of the eyes may be detected, and when areas of the black and white regions are lower than or equal to certain values, the device 100 may determine that the eyes are closed.

The condition about a facial expression is a condition in which the input image is selected as the face image when a certain facial expression is detected according to health status information to be measured. The device 100 may detect the face from the input image and perform expression recognition on the face to determine whether the certain facial expression is detected from the input image. The certain facial expression may be a smiling face, a lack of expression, or a face with closed eyes.

The condition about whether ears are shown is a condition in which the input image is selected as the face image when the face is detected from the input image and ears are shown in the input image.

In operation S740, when the face region satisfies the face image obtaining condition, the device 100 may store the face region as the face image.

When the face region satisfies the face image obtaining condition, the device 100 may extract data of the face region from the input image, and store the extracted data as the face image.

Figure 8:
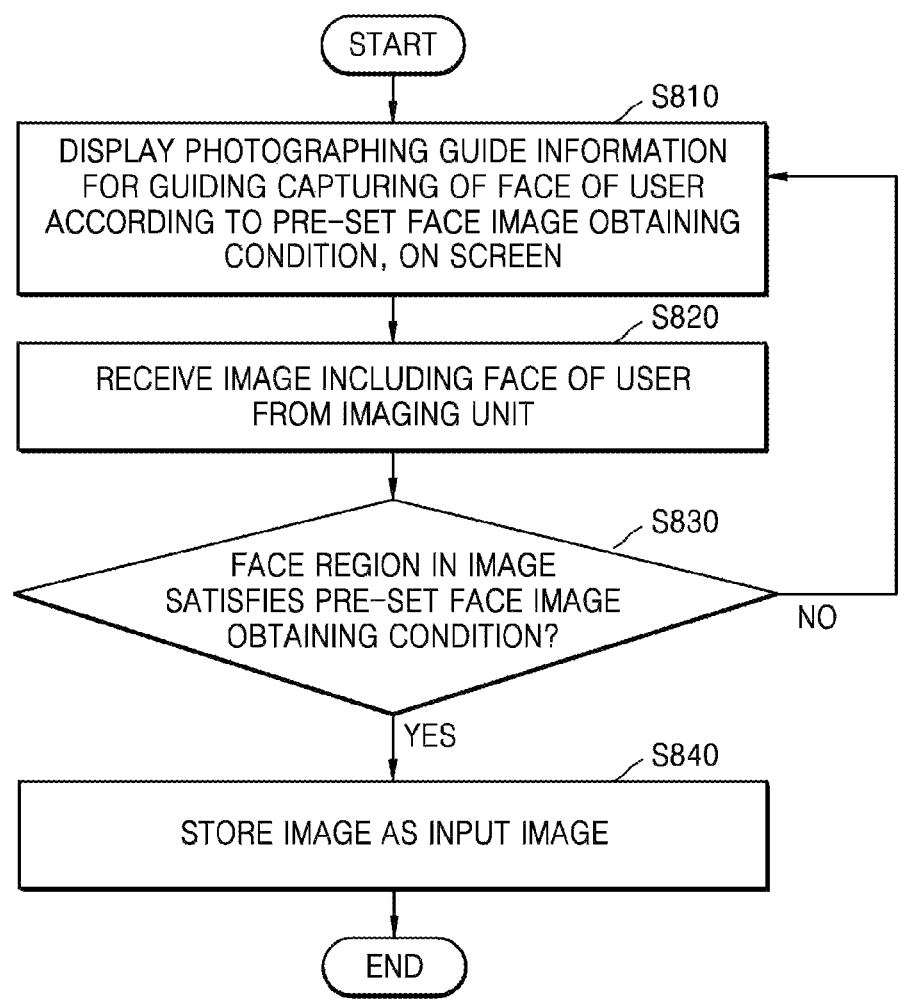
FIG. 8 is a flowchart of a method of obtaining, by a device, a face image by capturing a template, according to an exemplary embodiment.

FIG. 8 is a flowchart of a method of obtaining, by the device 100, a face image by capturing a template (i.e., capturing a template image), according to an exemplary embodiment.

In operation S810, the device 100 may display or output photographing guide information for guiding capturing of a face of a user according to a pre-set face image obtaining condition, on a screen.

For example, the device 100 may provide an application for diagnosing health of the user by capturing a template. Upon receiving a user input of selecting an application for capturing a template, the device 100 may enter a health examination mode. In the health examination mode, the device 100 may display the photographing guide information for guiding capturing of the face according to the pre-set face image obtaining condition.

According to an exemplary embodiment, when the device 100 enters the health examination mode as the user manipulates a menu while executing a photo album function of reproducing stored images, the device 100 may perform an operation of capturing a face image. Alternatively, the device 100 may perform the operation of capturing a face image when the user executes a health examination application provided in the device 100.

According to an exemplary embodiment, the device 100 may provide a photographing guide to capture a face image in the health examination mode. The photographing guide may be provided on a screen, in a sound, or by turning a light-emitting diode (LED) on and off.

According to an exemplary embodiment, the photographing guide may be provided while a preview image is displayed in the health examination mode. The device 100 may update the photographing guide by continuously determining whether the preview image satisfies the pre-set face image obtaining condition.

According to another exemplary embodiment, the photographing guide may be provided when a control signal that requests the photographing guide is received from the user. For example, the user may request the device 100 to provide the photographing guide by selecting a certain menu or button in the health examination mode.

According to another exemplary embodiment, when the device 100 includes a shutter button for receiving a shutter release signal and the shutter button may be half-pressed or fully pressed, the device 100 may calculate and provide the photographing guide when the shutter button is half-pressed. Here, when the shutter button is half-pressed, a first (S1) signal corresponding to auto-focus (AF) may be generated, and when the shutter button is fully pressed, a second (S2) signal corresponding to a shutter release signal may be generated.

The photographing guide information may include a guide image or a guide phrase for capturing a face according to the pre-set face image obtaining condition. The photographing guide information will be described in detail below with reference to FIGS. 9 through 14.

In operation S820, the device 100 may receive an image including the face of the user from an imaging unit included in the device 100.

Upon receiving the image from the imaging unit, the device 100 may display the image.

In operation S830, the device 100 may determine whether a face region in the image satisfies the pre-set face image obtaining condition.

For example, the device 100 may determine whether a face is detected in the image based on a face detection algorithm.

Alternatively, for example, the device 100 may detect a direction of the face in the image, and determine whether the direction satisfies a reference direction. For example, the device 100 may calculate a yaw direction, a tilt direction, and a roll direction of the face from the image. The reference direction may be a direction captured when the face of the image is looking at a camera straight.

After detecting the direction of the face in the image, the device 100 may determine that the detected direction satisfies the reference direction when the detected direction is within a pre-set range from the reference direction.

Alternatively, for example, the device 100 may detect an illumination value during photographing. The device 100 may obtain the illumination value from an illumination sensor included in the device 100. Upon obtaining the illumination value, the device 100 may determine whether the illumination value is within a pre-set range.

Alternatively, for example, the device 100 may determine whether a subject or the camera is shaken during photographing. For example, the device 100 may obtain a value indicating a shaking level from a shaking sensor included in the device 100. The device 100 may determine whether the value indicating the shaking level is within a pre-set range.

Alternatively, for example, the device 100 may determine whether a size of the face in the image is equal to or larger than a pre-set base size.

When it is determined that the face region in the image satisfies the pre-set face image obtaining condition in operation S830, the device 100 may store the image as an input image in operation S840.

The device 100 may store only a face region detected in the input image as a face image. Alternatively, the device 100 may store the input image as a face image.

When it is determined that the face region in the image does not satisfy the pre-set face image obtaining condition in operation S830, the device 100 may display the photographing guide information to indicate the pre-set face image obtaining condition that is not satisfied.

For example, when an angle of the face is not within a pre-set angle range, the device 100 may display a direction and angle of the face for the user on the screen.

Figure 9:
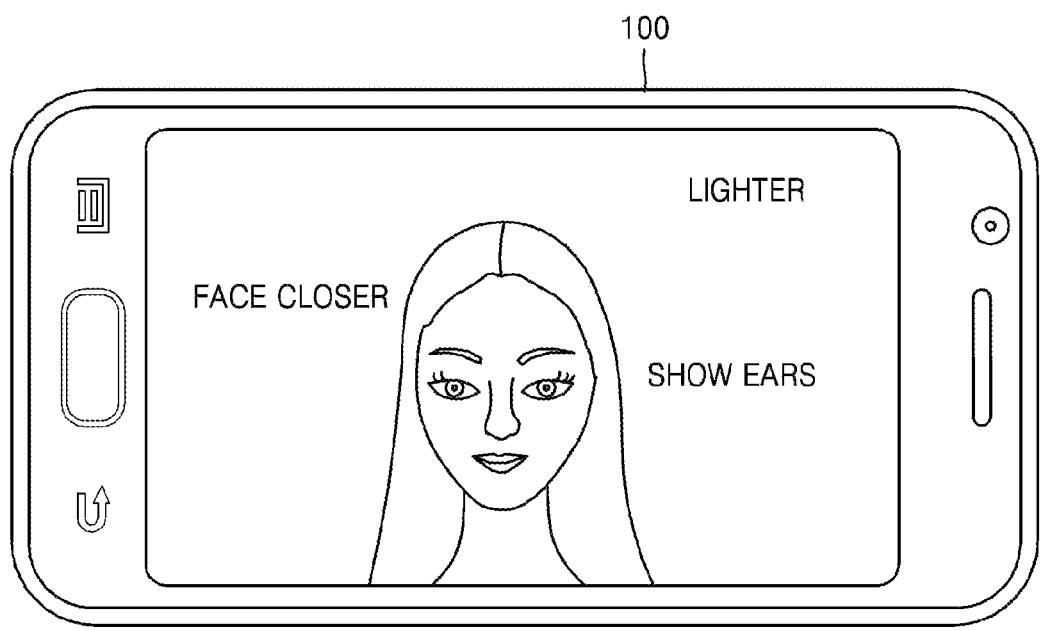
FIG. 9 is a diagram for describing a method of providing, by a device, guide information while capturing a template, according to an exemplary embodiment.

FIG. 9 is a diagram for describing a method of providing, by the device 100, guide information while capturing a template, according to an exemplary embodiment.

When a template is captured for a health examination, a preview image may be displayed as shown in FIG. 9. According to the current exemplary embodiment, the preview image may provide a guide for satisfying a face image obtaining condition.

The device 100 determines whether the face image obtaining condition is satisfied from the preview image, and may provide a photographing guide about whether the face image obtaining condition is satisfied or about how to capture an image in order to satisfy the face image obtaining condition.

The photographing guide may be displayed on a screen as shown in FIG. 9. According to another exemplary embodiment, the photographing guide may be output as audio.

The photographing guide may include, as shown in FIG. 9, an instruction to draw a face closer to adjust a face size or an instruction to place the face farther away. Alternatively, the photographing guide may include a guide to increase or decrease illumination based on measured illumination, an instruction to show ears when ears are not shown, a guide about a facial expression or a face location, etc.

According to an exemplary embodiment, the device 100 may provide a photographing guide about one or more conditions that are not satisfied from among the face image obtaining conditions, and end the providing of the photographing guide of a face image obtaining condition whenever the one or more conditions are satisfied. According to another exemplary embodiment, the device 100 may display all face image obtaining conditions on a display unit (e.g., display), and provide information about whether each face image obtaining condition is satisfied.

Figure 10:
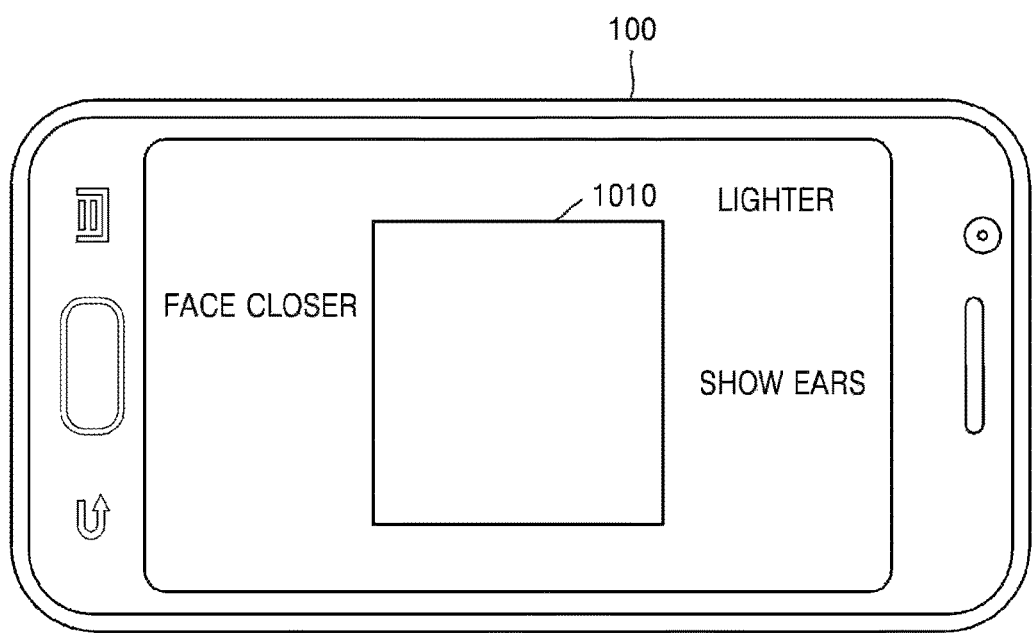
FIG. 10 is a diagram for describing a method of providing, by a device, guide information while capturing a template, according to another exemplary embodiment.

FIG. 10 is a diagram for describing a method of providing, by the device 100, guide information while capturing a template, according to another exemplary embodiment.

According to the current exemplary embodiment, the device 100 may provide a face box 1010 on a preview screen to notify a user about a size and location of a face according to a face image obtaining condition. The user may easily capture a face image by disposing the face in the face box 1010.

According to an exemplary embodiment, the device 100 may detect a location and a size of the face in a preview image, and output, through the face box 1010, information about whether the face image obtaining condition is satisfied by comparing the detected location and size with the face image obtaining condition. For example, the device 100 may provide, to the user, information about whether the face image obtaining condition is satisfied by changing at least one of a color, a type of line, and existence of the face box 1010 based on whether the location and size of the face satisfy the face image obtaining condition.

When the face image is obtained, the device 100 may generate an image file of the face image, and store the image file. The device 100 may add, to the image file, information that content of the image file is the face image used for a health examination.

According to an exemplary embodiment, the information that the content of the image file is the face image may be stored in a header of the image file.

According to another exemplary embodiment, the device 100 may store and manage the information that the content of the image file is the face image as separate data. For example, the device 100 may store a file name and storage path of the image file as separate files.

According to an exemplary embodiment, the device 100 may add information related to the face image obtaining condition to the image file. For example, the device 100 may store, in the image file together with the image file, information about at least one of a face location, a face size, a facial expression, illumination during photographing, a face direction, and shaking during photographing. The information that the content of the image file is the face image and the information related to the face image obtaining condition may be stored in the header of the image file.

Figure 11:
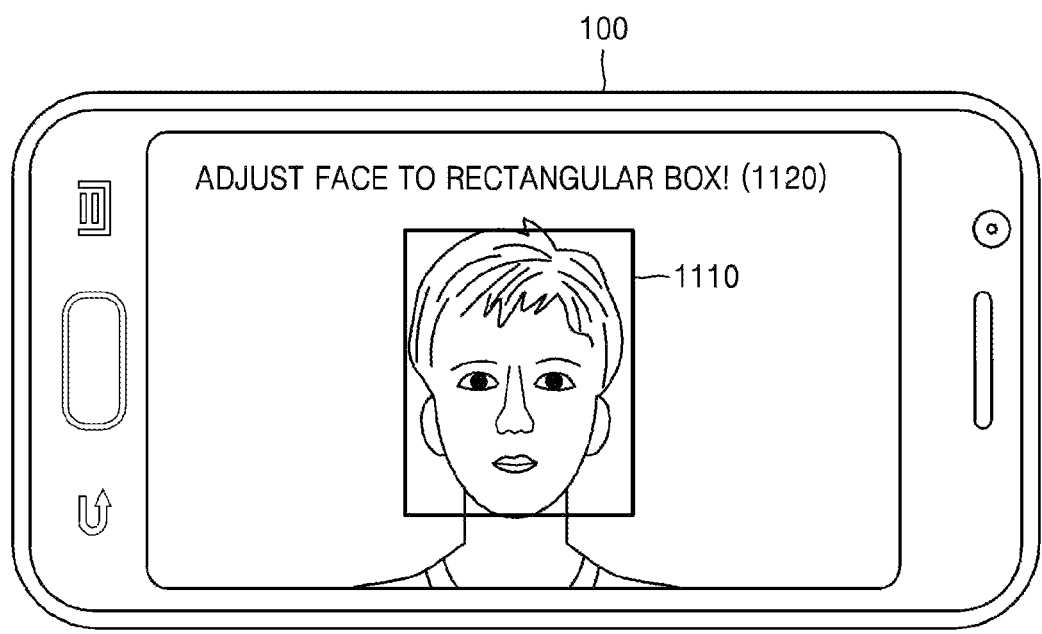
FIG. 11 is a diagram for describing a method of capturing, by a device, a face within a certain distance from a camera while capturing a template, according to an exemplary embodiment.

FIG. 11 is a diagram for describing a method of capturing, by the device 100, a face within a certain distance from a camera while capturing a template, according to an exemplary embodiment.

Referring to FIG. 11, the device 100 may display a user interface for capturing a face within a certain distance from a camera.

For example, the device 100 may display, on a screen, a guide image 1110 for capturing a face at a location away from the camera by a pre-set distance. The guide image 1110 may be rectangular or oval (e.g., like a shape of a face).

Also, for example, the device 100 may display a guide phrase 1120 to adjust the face in the guide image 1110, together with the guide image 1110.

The device 100 may determine that the face of the user is at the location away from the camera by the pre-set distance based on whether the face is within a region of the guide image 1110. For example, the device 100 may detect a contour of the face from an image received from an imaging unit, and determine whether the contour is within the region of the guide image 1110. When the contour of the face is within the region of the guide image 1110, the device 100 may determine that the face is at the location away from the camera by the pre-set distance.

When the face is within the region of the guide image 1110, the device 100 may determine the image as an input image. When the face is not within the region of the guide image 1110, the device 100 may display a guide phrase to move the face in a certain direction based on the location of the face.

Figure 12:
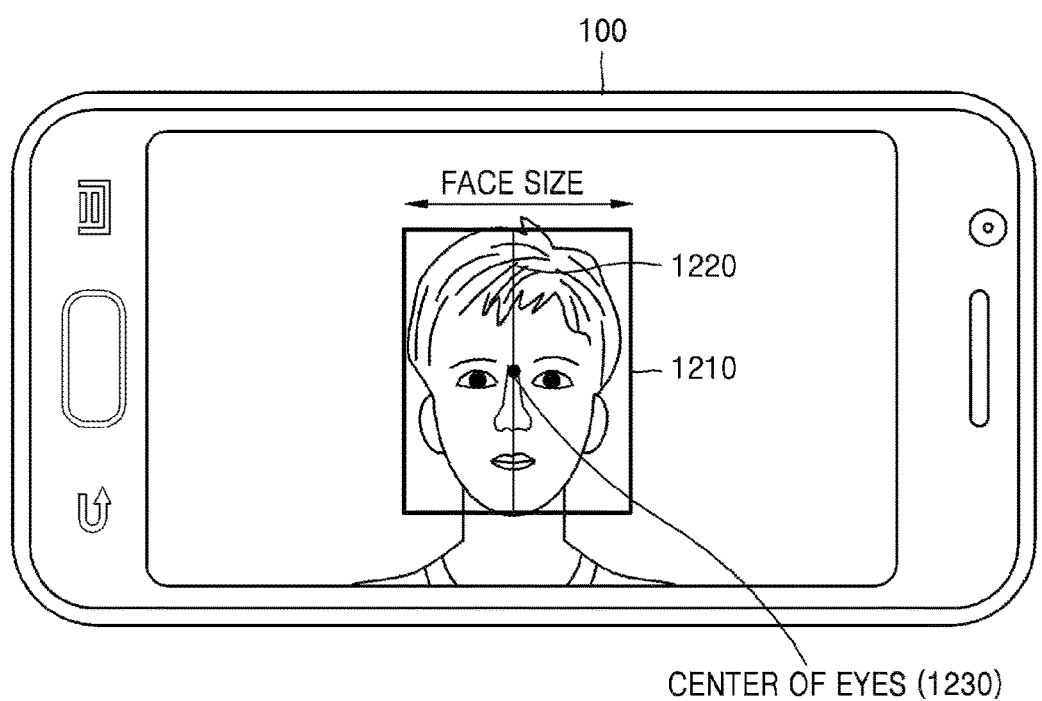
FIG. 12 is a diagram for describing a method of capturing, by a device, a face while capturing a template such that a direction of the face within an input image is a direction facing a camera straight, according to an exemplary embodiment.

FIG. 12 is a diagram for describing a method of capturing, by the device 100, a face while capturing a template such that a direction of the face within an input image is a direction facing a camera straight, according to an exemplary embodiment.

Referring to FIG. 12, the device 100 may determine whether a face is looking at a camera straight, as opposed to looking to the left or the right.

For example, the device 100 may detect a face region from an image received from an imaging unit. Upon detecting the face region, the device 100 may detect locations of eyes, a nose, or a lip in the face region. Upon detecting the locations of the eyes, the device 100 may determine a center point between the eyes. At this time, when the center point is within a pre-set range in a horizontal direction from a vertical center line 1220 that divides a box image 1210 by two, the device 100 may determine that the face is looking at the camera straight.

When the center point is not within the pre-set range from the vertical center line 1220, the device 100 may display a guide phrase guiding the user to turn the face left or right.

Figure 13:
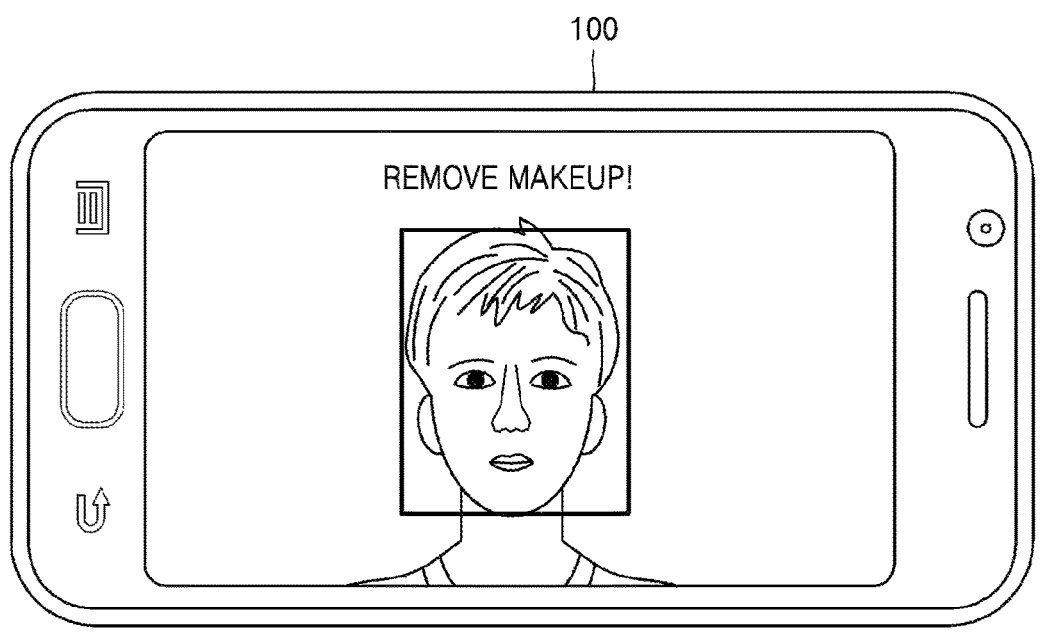
FIG. 13 is a diagram for describing a method of obtaining, by a device, an input image while capturing a template, based on whether a face of a user is wearing makeup, according to an exemplary embodiment.

FIG. 13 is a diagram for describing a method of obtaining, by the device 100, an input image while capturing a template, based on whether a face of a user is wearing makeup, according to an exemplary embodiment.

Referring to FIG. 13, the device 100 may detect a face region in an image received from an imaging unit, and determine whether a face of a user is artificially made up based on color data of the detected face region.

The device 100 may determine whether the face is made up based on at least one of color, brightness, and saturation of the color data.

For example, eyelid regions may be detected from the face region. When color data of the eyelid regions is different from a skin color of other regions of the face by at least a reference value, the device 100 may determine that the eyelid regions are made up.

Alternatively, for example, the device 100 may detect a lip region from the face region. When color data of the lip region has brightness or saturation exceeding a base range, the device 100 may determine that the lip region is not an original lip color of the user.

Alternatively, the device 100 may store a face image of the user without makeup as a base image. For example, the device 100 may store a face image including a most number of blemishes, pimples, or moles from among most recently captured face images of the user, as a base image.

Upon detecting the face region, the device 100 may detect locations of blemishes, pimples, or moles in the face region. Then, the device 100 may determine that the user is wearing makeup when the number of blemishes, pimples, or moles detected from the face region is different from that in the base image by at least a reference number. Here, the device 100 may compare the face region with the base image according to regions. Alternatively, the device 100 may compare only a pre-set certain region of the face region with the base image.

When it is determined that the user is wearing makeup, the device 100 may display a guide phrase guiding to remove makeup.

On the other hand, when it is determined that the user is not wearing makeup, the device 100 may determine the image received from the imaging unit as an input image. Alternatively, when it is determined that only a certain region is made up, the device 100 may determine the image received from the imaging unit as an input image, obtain a face image from the input image, and obtain health status information from a face region excluding a region with makeup.

Figure 14:
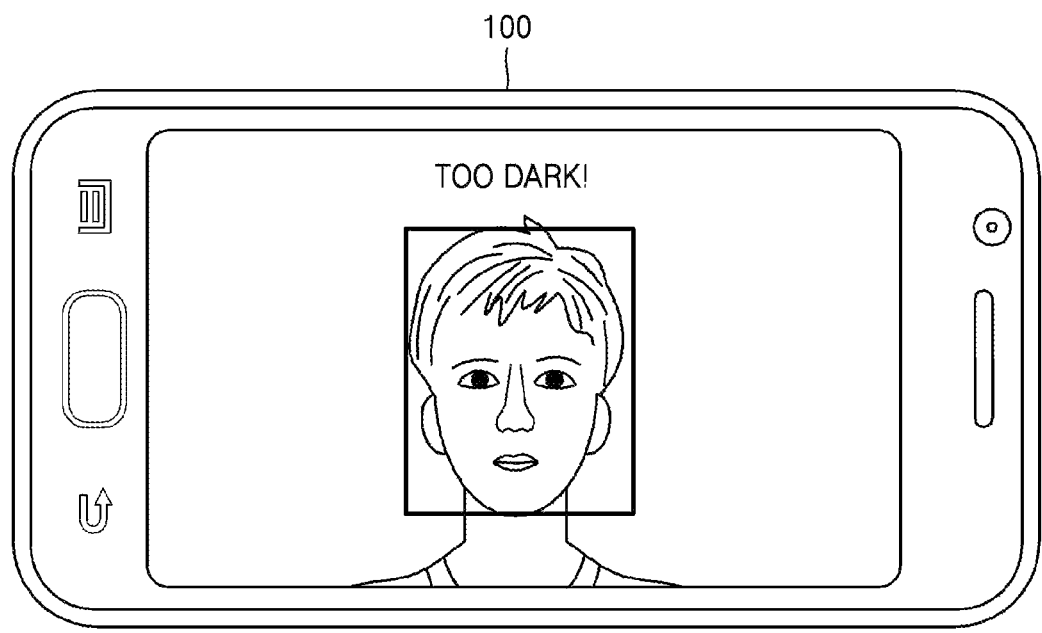
FIG. 14 is a diagram for describing a method of obtaining, by a device, an input image according to a pre-set illumination value while capturing a template, according to an exemplary embodiment.

FIG. 14 is a diagram for describing a method of obtaining, by the device 100, an input image according to a pre-set illumination value while capturing a template, according to an exemplary embodiment.

Referring to FIG. 14, the device 100 may determine whether an illumination value is within a base range while capturing a face of a user.

The device 100 may measure the illumination value by using an illumination sensor included in the device 100. The device 100 may determine whether the measured illumination value is within the base range.

When the measured illumination value is higher or smaller than the base range, the device 100 may display a guide phrase requesting the user to move to a brighter or darker place.

Figure 15A:
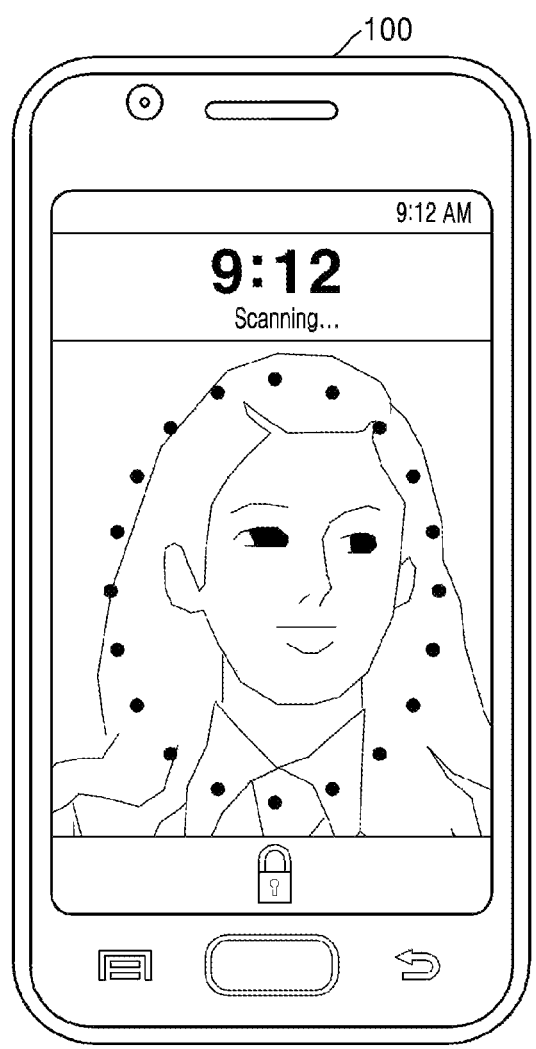
FIGS. 15A and 15B are diagrams for describing a method of obtaining, by a device, a face image in a face authentication mode while capturing a template, according to an exemplary embodiment.
Figure 15B:
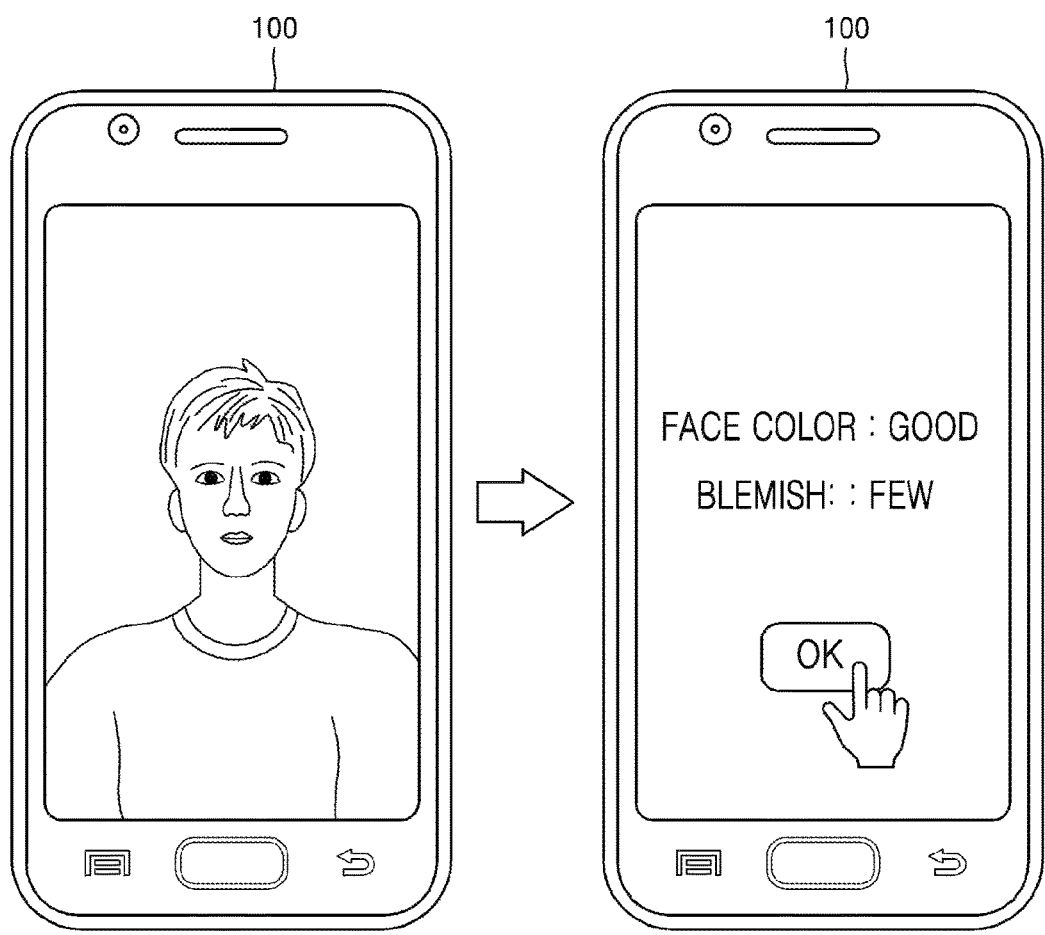

FIGS. 15A and 15B are diagrams for describing a method of obtaining, by the device 100, a face image in a face authentication mode while capturing a template, according to an exemplary embodiment.

Referring to FIG. 15A, when the device 100 is unlocked by using face authentication, an image captured in a mode of capturing a face of a user for face authentication may be used as a face image for a health examination.

For example, when the device 100 receives a user input for unlocking the device 100 by using face authentication in a locked state, the device 100 may enter a face authentication mode. In the face authentication mode, the device 100 may receive an image including the face of the user from an image sensor. The device 100 may detect a face region from the image, and determine whether the face region satisfies a face image obtaining condition. When the face region satisfies the face image obtaining condition, the device 100 may obtain data of the face region as a face image.

According to the current exemplary embodiment, the device 100 may easily obtain a face image without additional manipulation of the user. Also, since a face image captured for face authentication is captured under a condition similar to the face image obtaining condition, a face image satisfying the face image obtaining condition may be easily collected. Moreover, when an image is captured for face authentication, a face authentication process is performed on the captured image, and since ID information of a face in the captured image may be obtained as a result of the face authentication process, a face image and the ID information may be easily obtained without generating an additional load on the device 100.

According to the current exemplary embodiment, as shown in FIG. 15B, when face authentication succeeds in a face authentication mode, health status information extracted from a face image used for the face authentication may be provided on an initial screen after unlocking the device 100.

Figure 16:
FIG. 16 is a diagram for describing a method of obtaining, by a device, a face image of a user while executing a video call, according to an exemplary embodiment.

FIG. 16 is a diagram for describing a method of obtaining, by the device 100, a face image of a user while executing a video call, according to an exemplary embodiment.

Referring to FIG. 16, the device 100 may obtain a face image of a user while executing a video call application.

For example, the device 100 may determine whether a video call function is being performed in the device 100. When the video call function is being performed, the device 100 may receive an image including a face of a user from an image sensor. The device 100 may detect a face region from the image. Upon detecting the face region, the device 100 may determine whether the face region satisfies a face image obtaining condition. When the face region satisfies the face image obtaining condition, the device 100 may obtain data of the face region as a face image.

The device 100 may continuously receive images including the face of the user during a video call. The device 100 may select images received at regular time intervals from among the continuously received images, and determine whether face regions in the selected images satisfy the face image obtaining condition.

Figure 17:
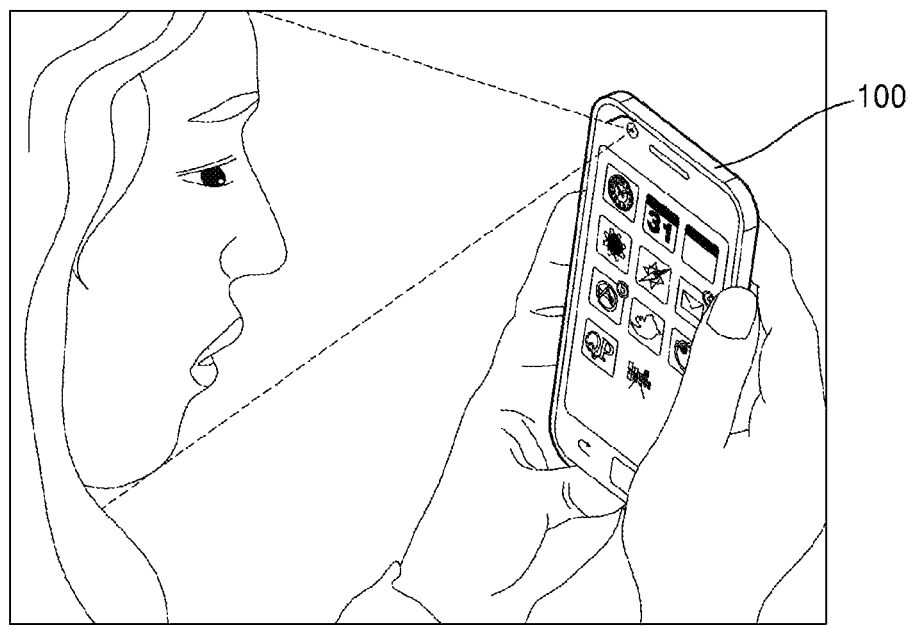
FIG. 17 is a diagram for describing a method of obtaining, by a device, a face image of a user while executing an application, according to an exemplary embodiment.

FIG. 17 is a diagram for describing a method of obtaining, by the device 100, a face image of a user while executing an application, according to an exemplary embodiment.

Referring to FIG. 17, the device 100 may obtain a face image of a user at pre-set time intervals while executing an application.

For example, the device 100 may determine whether a game, a moving image, or a web browser is being executed in the device 100. When the game, the moving image, or the web browser is being executed in the device 100, the device 100 may capture an image by driving an imaging unit included in the device 100. The device 100 may capture an image by driving the imaging unit when the application starts to be executed, or may capture an image by periodically driving the imaging unit.

Then, the device 100 may determine whether a face region exists in the captured image. When the face region is detected, the device 100 may determine whether the face region satisfies a face image obtaining condition. When the face region satisfies the face image obtaining condition, the device 100 may obtain data of the face region as a face image.

Figure 18:
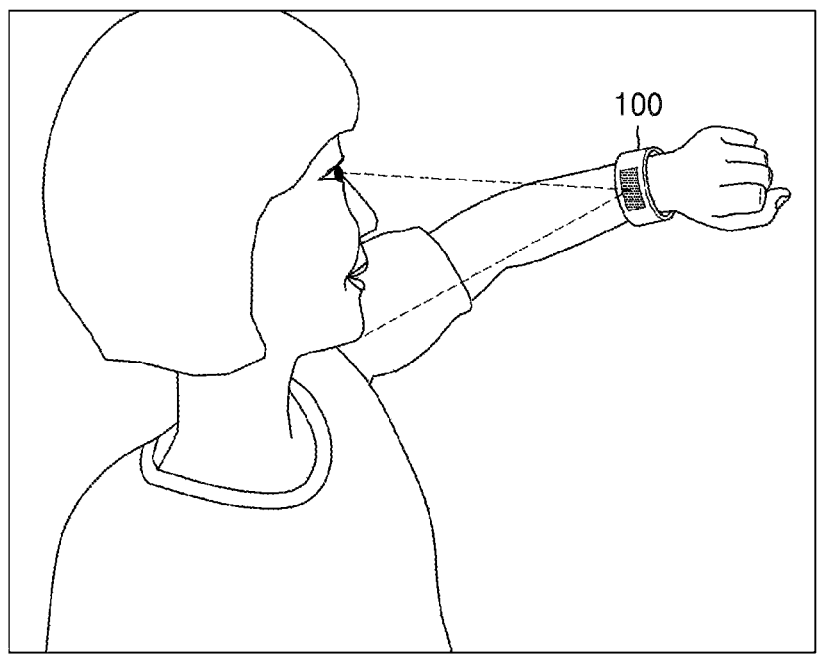
FIG. 18 is a diagram for describing a method of obtaining, by a device, a face image of a user when the device is worn on a wrist, according to an exemplary embodiment.

FIG. 18 is a diagram for describing a method of obtaining, by the device 100, a face image of a user when the device 100 is worn on a wrist, according to an exemplary embodiment.

Referring to FIG. 18, when the user looks at the device 100 by raising the wrist, the device 100 may capture the face image of the user.

The device 100 may determine whether the device 100 is close to a face of the user. For example, the device 100 may measure a moving direction or a moving distance of the device 100 may determined using a motion sensor included in the device 100. The moving direction may include a height from the ground, an upward direction, a downward direction, a leftward direction, a rightward direction, or a rotation direction of the wrist.

The device 100 may determine that the device 100 is within a reference distance from the face of the user based on the moving direction or the moving distance.

When it is determined that the device 100 is within the reference distance from the face, the device 100 may capture an image by driving an imaging unit included in the device 100. Then, the device 100 may determine whether a face region exists in the image. When the face region is detected, the device 100 may determine whether the face region satisfies a face image obtaining condition. When the face region satisfies the face image obtaining condition, the device 100 may obtain data of the face region as a face image.

Alternatively, when it is determined that the device 100 is within the reference distance from the face and the device 100 receives a user input, the device 100 may capture the image by driving the imaging unit.

Figure 19:
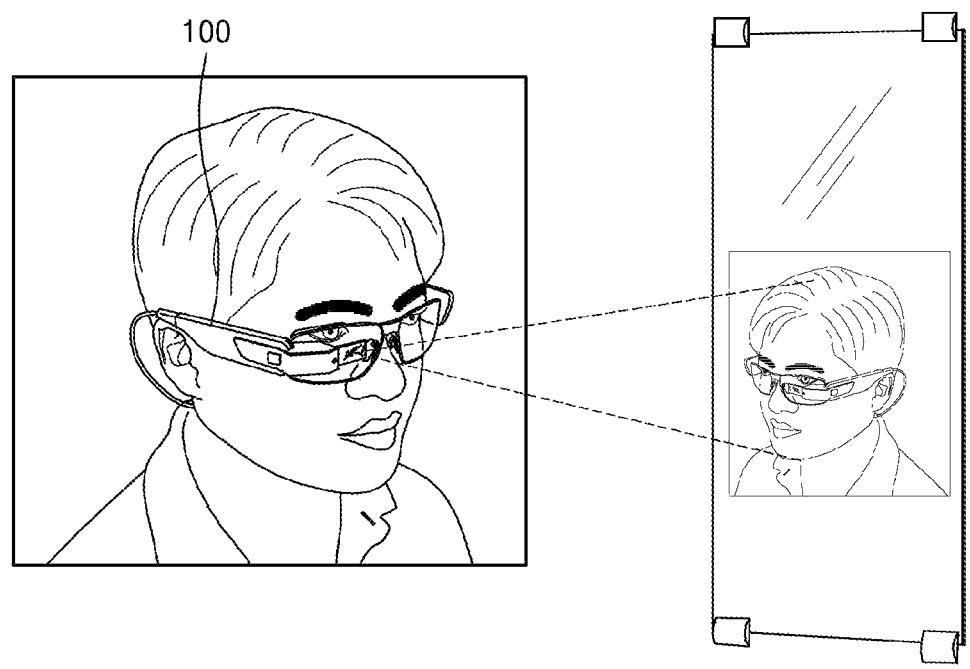
FIG. 19 is a diagram for describing a method of obtaining, by a device, a face image of a user when the device is a glasses type, according to an exemplary embodiment.

FIG. 19 is a diagram for describing a method of obtaining, by the device 100, a face image of a user when the device 100 is a glasses type, according to an exemplary embodiment.

Referring to FIG. 19, the device 100 may obtain the face image of the user as the user looks at a mirror while wearing the device 100 in the glasses type.

The device 100 may capture an environment in a visual field of the user by using an imaging unit included in the device 100. When the user looks at the mirror while wearing the device 100, the device 100 may obtain an image reflected from the mirror.

The device 100 may determine whether a face exists in the image received through the imaging unit. When the face exists, the device 100 may detect a face region from the image, and determine whether the face region is the face of the user. When the face region is the face of the user, the device 100 may determine whether the face region satisfies a face image obtaining condition. When the face region satisfies the face image obtaining condition, the device 100 may obtain data of the face region as a face image. According to another exemplary embodiment, the device 100 may capture one or more input images (e.g., regions of a face) using one or more imaging units that directly capture images of the face (i.e., without reflection from an external mirror).

FIG. 20 is a table for describing photographing circumstance information obtained while obtaining a face image by the device 100 using an imaging unit, according to an exemplary embodiment.

Referring to FIG. 20, the device 100 may obtain and store the photographing circumstance information while obtaining the face image of the user through the imaging unit included in the device 100.

The photographing circumstance information may include at least one of illumination during photographing, a photographed time, a photographed place, bio-information obtained from a biometric sensor, etc.

For example, the device 100 may obtain illumination information by using an illumination sensor attached to the device 100. Also, the device 100 may obtain time information when the face image is captured. Also, the device 100 may obtain photographed place information by using a device, such as a global positioning system (GPS) device or module.

Also, the device 100 may receive information from a biometric sensor attached to a body of the user to obtain bio-information of the user during photographing. For example, the device 100 may obtain information about a moving amount of the user from a pedometer attached to the body of the user. Also, the device 100 may receive information about a temperature of the user from a thermometer attached to the body of the user. Also, the device 100 may receive information about a heart rate of the user from an electrocardiogram device attached to the body of the user.

Also, the device 100 may obtain information about activity at a photographed point of time.

For example, activity information of the user may be estimated or determined based on the photographed place and the photographed time. For example, when the photographed place is a school and the photographed time is 10:00 am, the activity of the user may be estimated to be a school life.

Alternatively, for example, the activity information may be estimated by analyzing an image from which a face image is detected. For example, when food is included in the image, the activity of the user may be estimated to be having a meal.

Alternatively, the activity information of the user may be estimated by considering not only the image from which the face image is detected, but also images captured before and after a point of time the image is captured.

The photographing circumstance information may be stored according to an input image. For example, the photographing circumstance information may be recorded on an image file in a metadata form. Alternatively, the photographing circumstance information may be stored in a separate storage space according to ID information of the input image. The photographing circumstance information may be used when the device 100 obtains health status information of the user from facial condition information.

Figure 21:
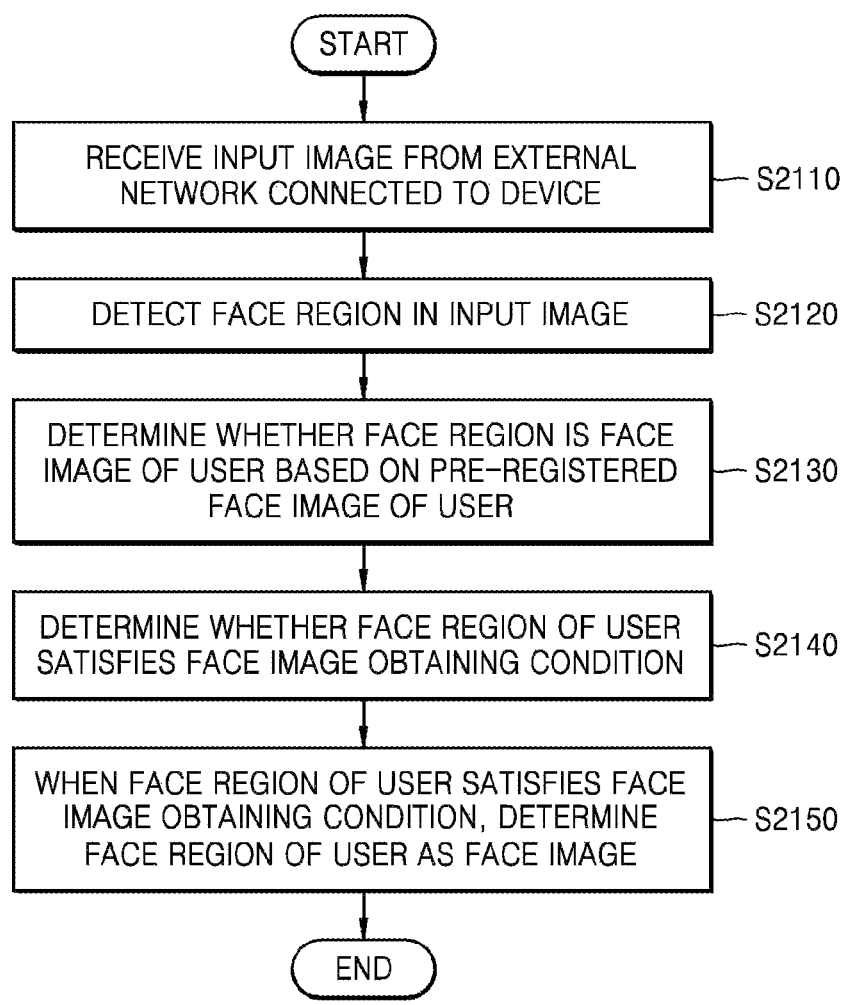
FIG. 21 is a flowchart of a method of obtaining, by a device, a face image from an image received from an external source, according to an exemplary embodiment.

FIG. 21 is a flowchart of a method of obtaining, by the device 100, a face image from an image received from an external source, according to an exemplary embodiment.

In operation S2110, the device 100 may receive an input image from a network (e.g., an external network) connected to the device 100.

Upon receiving a user input of selecting a photograph, the device 100 may download the selected photograph from an external server. The external server may be a social network service (SNS) server, a cloud storage server, or another device connected to the device 100 via wired connection, wireless connection, or local area network (LAN).

In operation S2120, the device 100 may detect face regions in the input image.

Upon receiving the input image from the external network, the device 100 may detect the face regions in the input image. The device 100 may detect the face regions from the input image, and extract locations of the face regions.

In operation S2130, the device 100 may extract a face region indicating a face of the user from among the face regions, based on pre-registered features of the face of the user.

For example, the device 100 may extract features of faces from the face regions. Examples of a method of extracting features of faces from face regions include Gabor filter method and a local binary pattern (LBP) method.

The device 100 may determine similarity between the features of the faces extracted from the face regions and the pre-registered features of the face of the user, and determine a face region having the similarity within a pre-set range as a face region of the user.

In operation S2140, the device 100 determines whether the face region of the user satisfies a face image obtaining condition. In operation S2150, when the face region of the user satisfies the face image obtaining condition, the device 100 may obtain the face region of the user as a face image.

Figure 22:
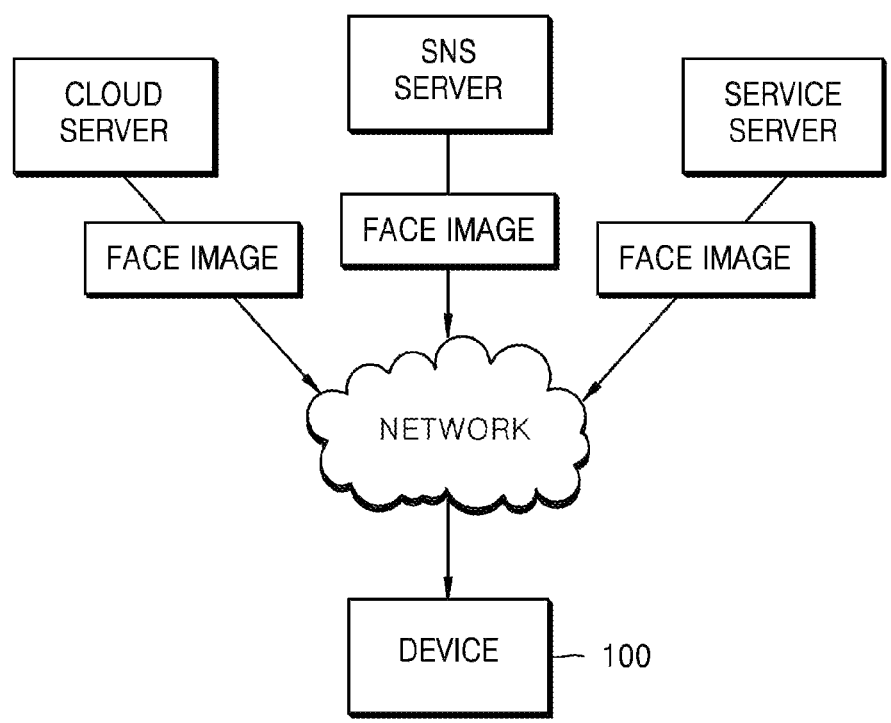
FIG. 22 is a diagram for describing a method of obtaining, by a device, a face image from an external server, according to an exemplary embodiment.

FIG. 22 is a diagram for describing a method of obtaining, by the device 100, a face image from an external server, according to an exemplary embodiment.

Referring to FIG. 22, the device 100 may exchange data, such as a face image, facial condition information, and health status information, with an external device or an external server.

The device 100 may use the received data to obtain health status information, or may transmit the face image, the facial condition information, or the health status information to the external device or the external server.

According to an exemplary embodiment, the device 100 may download the face image from the external server.

According to an exemplary embodiment, the device 100 may download the face image from a cloud server.

Alternatively, whenever an image including information that the image is a face image is added to a cloud account (e.g., a pre-assigned cloud account), the device 100 may download the image and use the image as a face image. Whether a new image is added to the cloud server may be determined, for example, via a notification pushed from the cloud server or periodical communication with the cloud server.

According to an exemplary embodiment, the device 100 may download a face image from an SNS server. For example, whenever an image is added to a pre-assigned SNS account, the device 100 may determine whether the image satisfies a face image obtaining condition, and use the image as the face image when the image satisfies the face image obtaining condition.

Alternatively, when an image including information that the image is a face image is added to the pre-assigned SNS account, the device 100 may download the image and use the image as a face image.

According to another exemplary embodiment, the device 100 may extract a face image from images available by using the pre-assigned SNS account. For example, the device 100 may extract the face image from a photograph registered in another SNS account registered as a friend of the pre-assigned SNS account, a photograph available in the pre-assigned SNS account by being shared by a user of the other SNS account, and a photograph to which the pre-assigned SNS account is tagged. The device 100 may determine whether the images available by using the pre-assigned SNS account satisfy a face image obtaining condition, and use an image that satisfies the face image obtaining condition as the face image.

Whether a new image is registered in the pre-assigned SNS account or the other SNS account may be determined, for example, via a notification pushed from the pre-assigned SNS account or the other SNS account, or periodical communication with the SNS server.

According to another exemplary embodiment, the device 100 may download the face image from a service server that provides a function of providing health status information. For example, face images may be stored in the service server according to user accounts, and the device 100 may download a face image from a certain account by accessing the certain account. According to an exemplary embodiment, the service server may provide the face image together with facial condition information and/or health status information related to the face image to the device 100.

According to an exemplary embodiment, the device 100 may adjust the face image according to a certain algorithm, extract facial condition information from the adjusted face image, and obtain health status information from the extracted facial condition information.

Figure 23A:
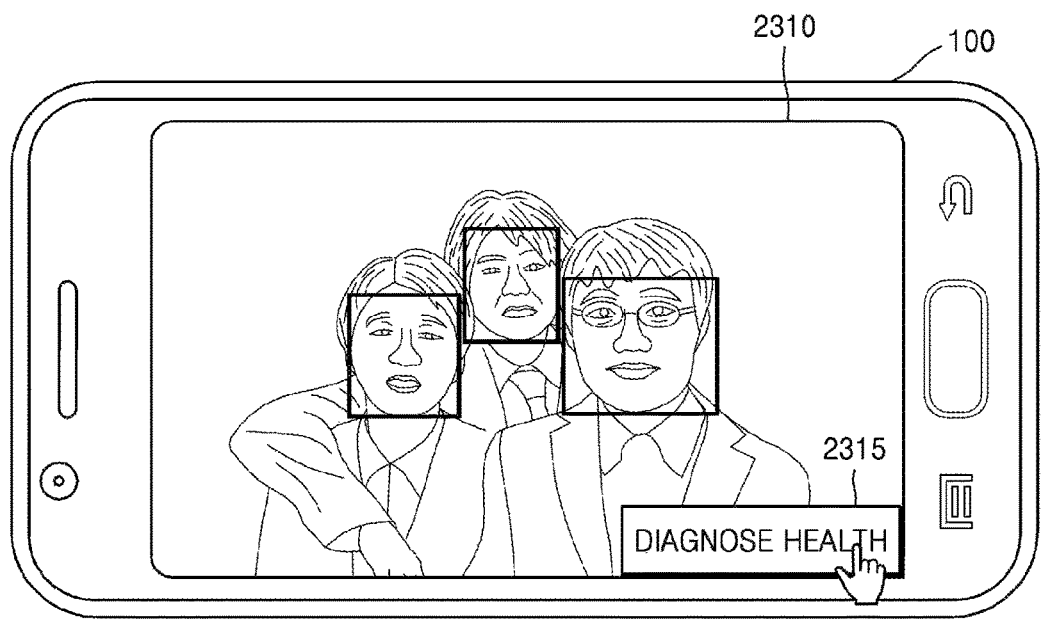
FIGS. 23A and 23B are diagrams for describing a method of obtaining, by a device, a face image of a user from an image selected by the user, according to an exemplary embodiment.
Figure 23B:
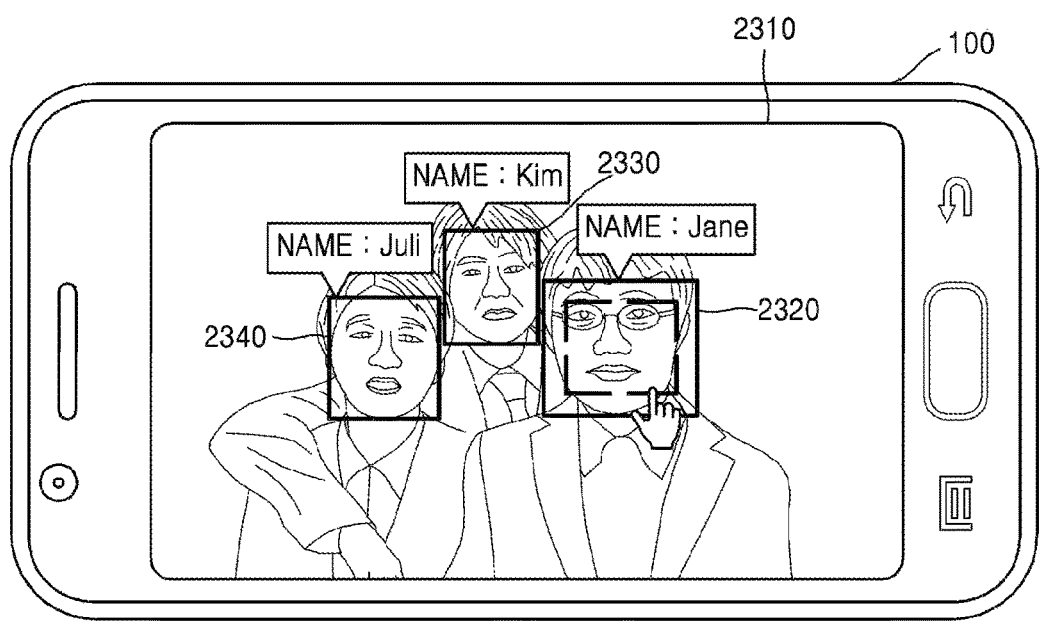

FIGS. 23A and 23B are diagrams for describing a method of obtaining, by the device 100, a face image of a user from an image 2310 selected by the user, according to an exemplary embodiment.

Referring to FIGS. 23A and 23B, the device 100 may obtain the face image of the user from the image 2310 selected by the user.

The device 100 may display the image 2310 from among a plurality of images stored in the device 100, on a screen. Also, the device 100 may display a menu 2315 for providing health status information of the user from a face of the user in the image 2310.

Upon receiving a user input of selecting the menu 2315, the device 100 may determine the image 2310 as an input image. When the image 2310 is determined as the input image, face regions 2320 through 2340 may be detected from the image 2310. The device 100 may detect the face regions 2320 through 2340 from the image 2310, and extract locations of the face regions 2320 through 2340.

Upon extracting the locations of the face regions 2320 through 2340, the device 100 may extract features of faces from the face regions 2320 through 2340. The device 100 may compare the features extracted from the face regions 2320 through 2340 with pre-registered features of the face of the user to determine the face of the user from the face regions 2320 through 2340. For example, when similarity between the features extracted from one of the face regions 2320 through 2340 and the pre-registered features is within a pre-set range, the one of the face regions 2320 through 2340 may be determined as the face region of the user.

Upon determining users indicated by the face regions 2320 through 2340, the device 100 may display ID information of the users according to the face regions 2320 through 2340.

Then, upon receiving a user input of selecting one of the face regions 2320 through 2340, for example, the face region 2330, the device 100 may determine whether the face region 2330 satisfies a face image obtaining condition. When the face region 2330 satisfies the face image obtaining condition, the face region 2330 may be obtained as a face image.

Also, the device 100 may normalize the face image based on a pre-set standard. The device 100 may extract facial condition information from the normalized face image. The device 100 may obtain health status information by using the facial condition information, and provide the health status information.

FIG. 24 is a diagram for describing a process of obtaining, by the device 100, a face image from images stored in the device 100, according to an exemplary embodiment.

Referring to FIG. 24, the device 100 may extract the face image from the images stored in the device 100. The device 100 may determine whether each of the stored images satisfies a face image obtaining condition, and extract a stored image satisfying the face image obtaining condition as the face image.

According to an exemplary embodiment, the device 100 may determine whether a new image satisfies the face image obtaining condition whenever the new image is captured and stored in the device 100 or whenever the new image is input from an external device and stored in the device 100.

According to another exemplary embodiment, the device 100 may periodically determine images of the stored images, which do not satisfy the face image obtaining condition yet, satisfy the face image obtaining condition. For example, the device 100 may determine whether new images that are stored for one week satisfy the face image obtaining condition per week.

According to another exemplary embodiment, the device 100 may determine whether images, for which satisfaction of the face image obtaining condition has not yet been determined, satisfy the face image obtaining condition, whenever a user inputs a request signal requesting health status information. For example, when the user inputs the request signal requesting for health status information while 100 images are stored in an electronic apparatus and it is determined whether the face image obtaining condition is satisfied for 90 images, the device 100 may extract face images from the remaining 10 images, extract facial condition information from the face images, and provide health status information.

Figure 25:
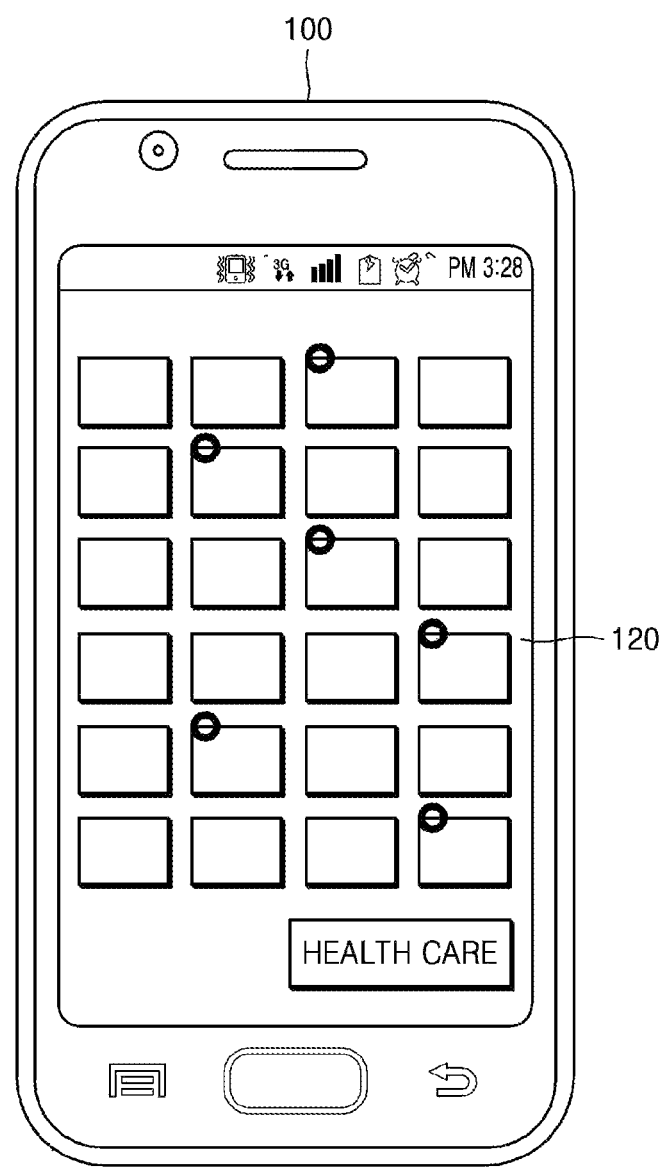
FIG. 25 is a diagram for describing a method of extracting, by a device, a face image from an image selected by a user, according to an exemplary embodiment.

FIG. 25 is a diagram for describing a method of extracting, by the device 100, a face image from an image selected by a user, according to an exemplary embodiment.

Referring to FIG. 25, the user may directly select an image to be used as the face image, from among images stored in the device 100. For example, the user may select the image to be used as the face image while a function or an application, such as a photo album or a gallery, is being executed. At this time, as shown in FIG. 25, the user may select the image to be used as the face image while thumbnail images 120 of the images stored in the device 100 are displayed.

According to an exemplary embodiment, the device 100 may use all images selected by the user as face images.

According to another exemplary embodiment, the device 100 may determine whether images selected by the user satisfy a face image obtaining condition, and extract only an image satisfying the face image obtaining condition as the face image.

According to an exemplary embodiment, as shown in FIG. 25, when the user inputs a control signal requesting health status information while a plurality of images are selected, the device 100 may extract facial condition information by using the selected images, and extract and provide health status information. The control signal may be generated as the user presses a "health care" button shown in FIG. 25.

According to another exemplary embodiment, when the user inputs the control signal while the function, such as the photo album or the gallery, is being executed, the device 100 may automatically determine whether an image included in the photo album or the gallery satisfies the face image obtaining condition, extract a face image, and obtain and provide facial condition information and health status information from the face image. In this case, the user may obtain the health status information via one selection signal, without having to select an image to be used as the face image.

Figure 26:
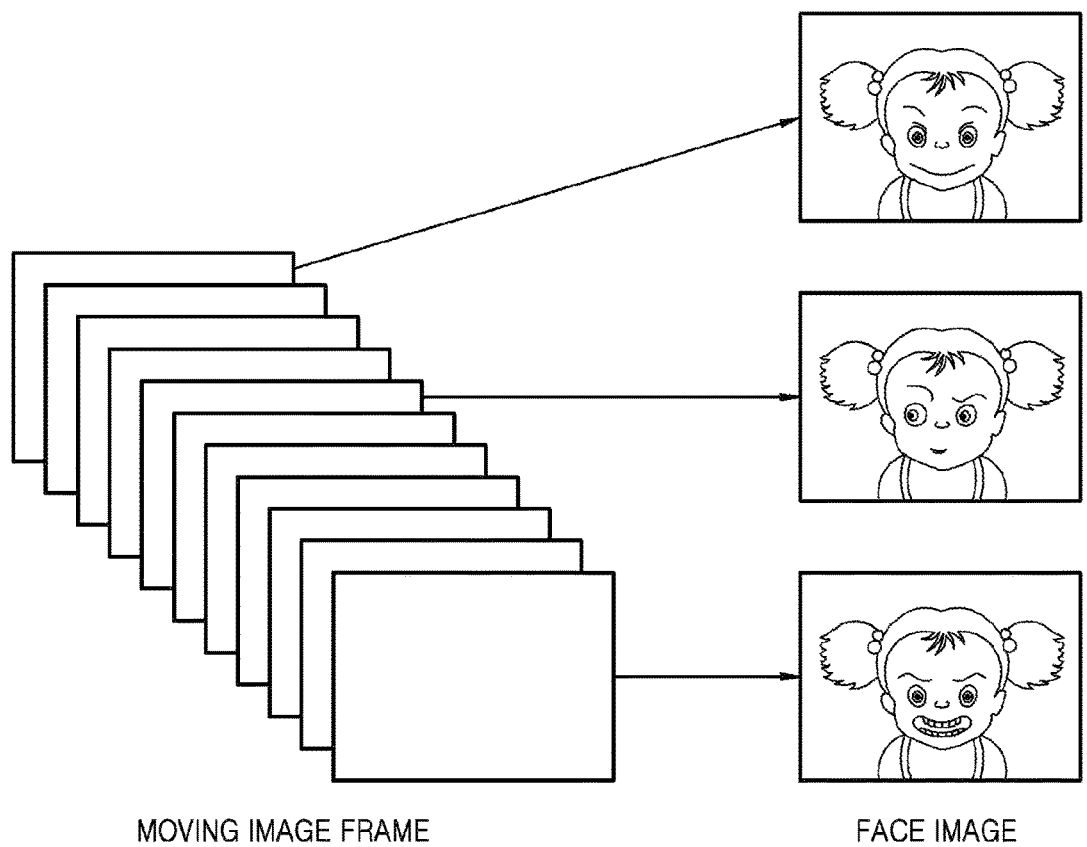
FIG. 26 is a diagram for describing a method of extracting, by a device, a face image from a moving image, according to an exemplary embodiment.

FIG. 26 is a diagram for describing a method of extracting, by the device 100, a face image from a moving image, according to an exemplary embodiment.

Referring to FIG. 26, the device 100 may extract the face image from the moving image. In this case, the device 100 may determine whether each of moving image frames satisfies a face image obtaining condition and extract a moving image frame satisfying the face image obtaining condition to be used as the face image. According to an exemplary embodiment, when consecutive moving image frames satisfy the face image obtaining condition, the device 100 may extract one of the consecutive moving image frames as the face image (e.g., a first or a middle one of the consecutive moving image frames).

According to an exemplary embodiment, a user may select a health examination function while the moving image is reproduced, and extract health status information from the moving image. When an input of selecting the health examination function is received from the user while the moving image is reproduced, the device 100 may determine whether the moving image frames of the moving image satisfy the face image obtaining condition, extract a face image, extract facial condition information, and then extract and provide health status information.

According to another exemplary embodiment, the device 100 may obtain the facial condition information and the health status information by using the moving image. For example, the device 100 may extract the facial condition information, such as movement of facial muscles, blinking degrees of eyes, and flexibility of a neck, by using the moving image. Then, the device 100 may determine a condition of the user by using the movement of the facial muscles, the blinking degrees of the eyes, and the flexibility of the neck.

Figure 27:
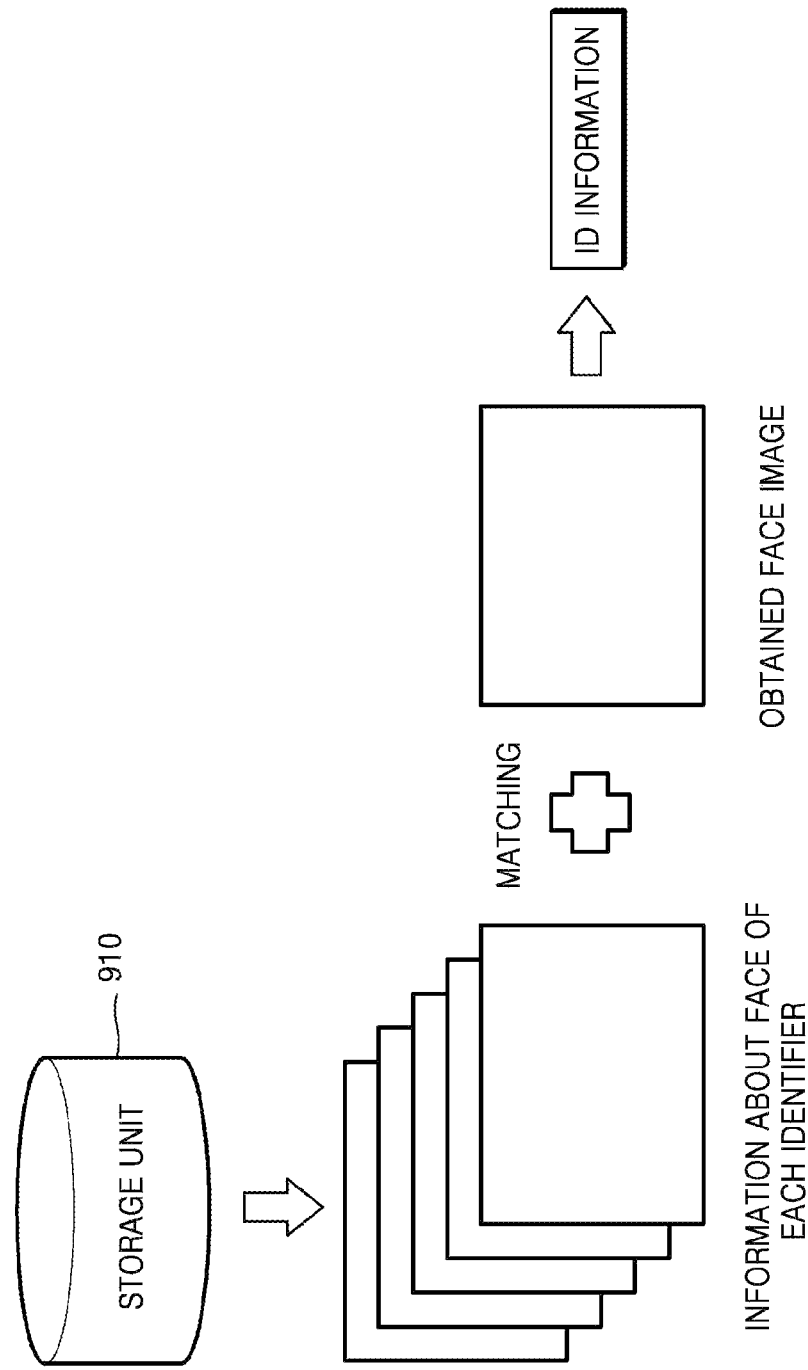
FIG. 27 is a diagram for describing a process of assigning, by a device, an identifier to a face image, according to an exemplary embodiment.

FIG. 27 is a diagram for describing a process of assigning, by the device 100, an identifier to a face image, according to an exemplary embodiment.

According to the current exemplary embodiment, when the face image is input, the device 100 may compare information about faces of registered identifiers and the face image to determine ID information of the face image. For example, a representative face image of each identifier or facial feature point information of each identifier may be stored in the device 100. In this case, the device 100 may compare the representative face image or the facial feature point information with the face image, and determine to which identifier the face image belongs.

According to the current exemplary embodiment, classification information and an identifier of the face image may be stored together with the face image. The classification information is information indicating that the face image is used to determine health status information. Also, according to an exemplary embodiment, additional information may be stored together with the face image and the identifier.

Figure 28:
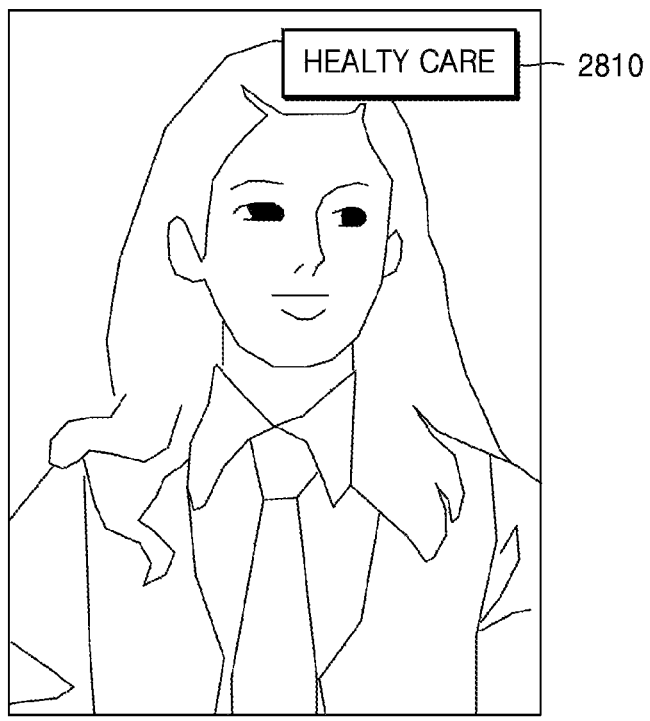
FIG. 28 is a diagram for describing a method of recording, by a device, information that health status information is obtained from an image, on a file of the image, according to an exemplary embodiment.

FIG. 28 is a diagram for describing a method of recording, by the device 100, information that health status information is obtained from an image, in a file of the image, according to an exemplary embodiment.

According to the current exemplary embodiment, the device 100 may record at least one or a combination of classification information, an identifier, and additional information in a face image as a pixel value in a visible form. For example, as shown in FIG. 28, a button 2810 of "HEALTH CARE" may be inserted on the face image in a pixel value. Recording information as a pixel value in a visible form may mean that the information is recorded in a letter, an icon, a barcode, or a quick response (QR) code. According to the current exemplary embodiment, when information is recorded on an image as a pixel value in a visible form, a user may intuitively know that the image is a face image for a health examination. Also, by inserting an icon, a barcode, or a QR code to an image, the user may request facial condition information or health status information in more detail or the device 100 may enter a health examination mode, by using the icon, the barcode, or the QR code.

According to an exemplary embodiment, the device 100 may record at least one of or a combination of the classification information, the identifier, and the additional information on the face image as a pixel value in a non-visible form. For example, a code or a sign indicating that the face image is used for a health examination function may be recorded on the face image as a pixel value in a non-visible form. Recording information as a pixel value in a non-visible form may mean that the information is recorded in a letter, an icon, a barcode, or a QR code. Such information may be read by using an algorithm for reading the non-visible form.

According to the current exemplary embodiment in which at least one or a combination of the classification information, the identifier, the additional information is recorded as a pixel value in a visible or non-visible form, certain information may be stored in a face image without having to use an additional storage space. Also, according to the current exemplary embodiment, the classification information, the identifier, and the additional information may be stored without being restricted by a file format. According to the current exemplary embodiment, the classification information, the identifier, or the additional information may not be recorded as a pixel value, but information about a storage path or link of the classification information, the identifier, or the additional information may be recorded as a pixel value.

According to an exemplary embodiment, the device 100 may store at least one or a combination of the classification information, the identifier, and the additional information in a header of a file of the face image. For example, when an image file is stored in an exchangeable image file (Exif) format, at least one or a combination of the classification information, the identifier, and the additional information may be stored in the header of an Exif file.

FIG. 29 is a table for describing a method of storing, by the device 100, a face image, according to an exemplary embodiment.

According to an exemplary embodiment, the device 100 may store and manage at least one or a combination of classification information, an identifier, and additional information of each of files of face images used for a health examination functions, as separate data. For example, the device 100 may store at least one of or a combination of the classification information, the identifier, and the additional information of each of the files of the face images as separate management files.

According to an exemplary embodiment, such separate management files may be stored in a storage space, such as a photo album or a gallery, where the face images are stored. According to another exemplary embodiment, the separate management files may be stored in a storage space for an application providing the health examination function. As shown in FIG. 29, the separate management files may store a storage path and an identifier of each file.

Figure 30:
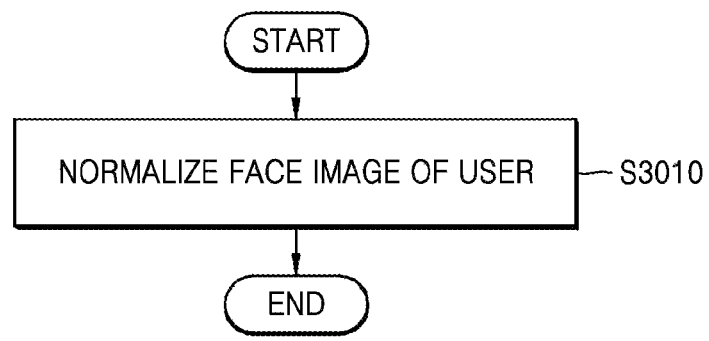
FIG. 30 is a flowchart of a method of normalizing, by a device, a face image, according to an exemplary embodiment.

FIG. 30 is a flowchart of a method of normalizing, by the device 100, a face image, according to an exemplary embodiment.

In operation S3010, the device 100 may normalize the face image.

The normalizing of the face image may mean that an attribute value of the face image is adjusted to a pre-set standard. The attribute value may be a size of the face image, brightness of the face image, and a hue change value according to an effect of illuminance.

Since photographing environments or photographing methods may be different according to input images, attribute values of face images obtained from the input images may be different. Accordingly, the device 100 may normalize the face images so as to obtain health status information of the same user under the same or similar condition.

Also, since the input images are captured under different photographing conditions, accuracy of the health status information may deteriorate as facial condition information is wrongly extracted based on the photographing conditions. In order to exclude variables according to the photographing conditions from the face images as much as possible, the device 100 may adjust the face images to increase the accuracy of the health status information.

According to an exemplary embodiment, the device 100 may adjust the face images according to the photographing conditions. For example, brightness of the face image may be adjusted by using information about illumination during photographing. The information about illumination may be detected by an illumination sensor included in an electronic apparatus. Alternatively, white balance of the face image may be adjusted by using information about white balance during photographing.

According to an exemplary embodiment, the device 100 may adjust a color of the face image based on a color of a certain organ or region of the face image. For example, since a color of a neck does not largely change according to a health status, the color of the face image may be adjusted based on the color of the neck. In this case, color information of a neck of a user corresponding to the face image may be pre-stored and when the face image of the user is obtained, the color of the face image may be adjusted based on the pre-stored color information of the neck. The entire color of the face image may be adjusted such that the color of the neck in the face image is adjusted according to the pre-stored color information of the neck.

According to an exemplary embodiment, when a red-eye effect is generated in the face image, the device 100 may perform red-eye compensation.

According to an exemplary embodiment, when the face image is shaken while being captured or captured by an imaging unit that is shaking, the device 100 may perform shaking compensation.

According to an exemplary embodiment, when the face image is captured in a health examination mode, the device 100 may request the user to capture a white subject or object in order to obtain information about white balance during photographing. The white object may be, for example, a white paper.

According to an exemplary embodiment, some or all of a method of adjusting the face image according to the photographing condition, a method of adjusting the color of the face image based on the color of the certain organ or region, a method of performing the red-eye compensation, and a method of performing shaking compensation may be performed.

After adjusting the face image, the device 100 may extract facial condition information from the adjusted face image, obtain health status information, and provide the health status information.

Figure 31:
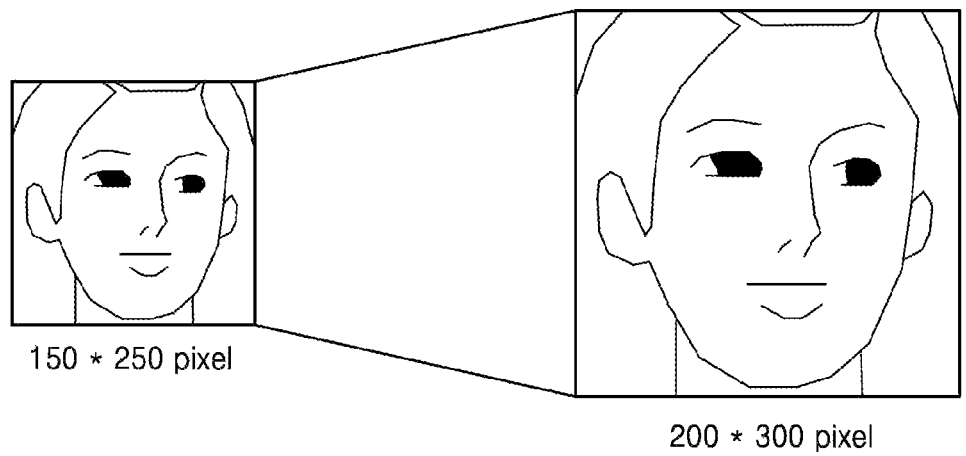
FIG. 31 is a diagram for describing a method of normalizing, by a device, a size of a face image, according to an exemplary embodiment.

FIG. 31 is a diagram for describing a method of normalizing, by the device 100, a size of a face image, according to an exemplary embodiment.

Referring to FIG. 31, the device 100 may obtain the face image from an input image, and normalize the size of the face image to a base size.

The base size may be stored in the device 100. For example, the base size may be set to be a resolution of 200×300 in the device 100.

When the size of the face image is smaller than the base size, the device 100 may increase the face image to the base size by applying an up-sampling or interpolation method on pixel data of the face image. When the size of the face image is larger than the base size, the device 100 may decrease the face image to the base size by applying a sub-sampling or down-sampling method on the pixel data of the face image.

By normalizing the size of the face image to the base size, a size of a face region in the face image may also be normalized. Also, since the face image is an image from which only the face region is detected from the input image, the size of the face image may be considered as the size of the face region. By adjusting the size of the face image to the base size, facial condition information shown on a face of a user may be extracted from the face image under the same face size condition.

Figure 32A:
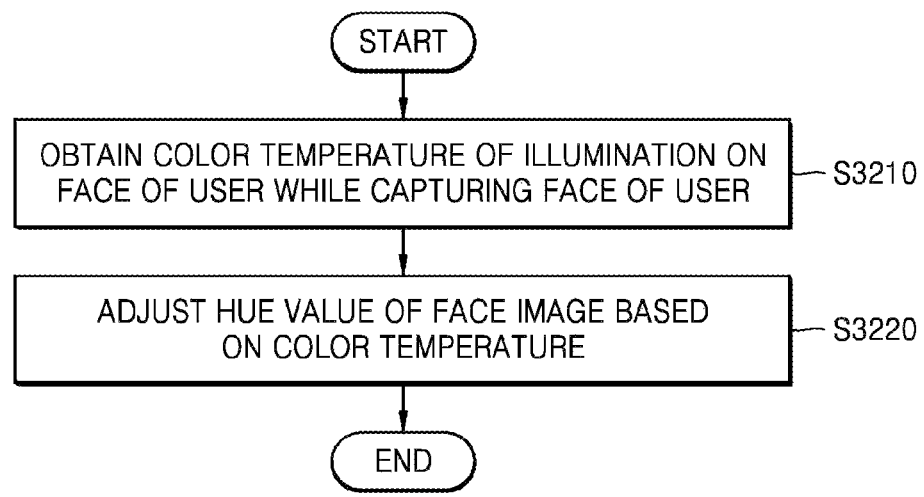
Figure 32C:
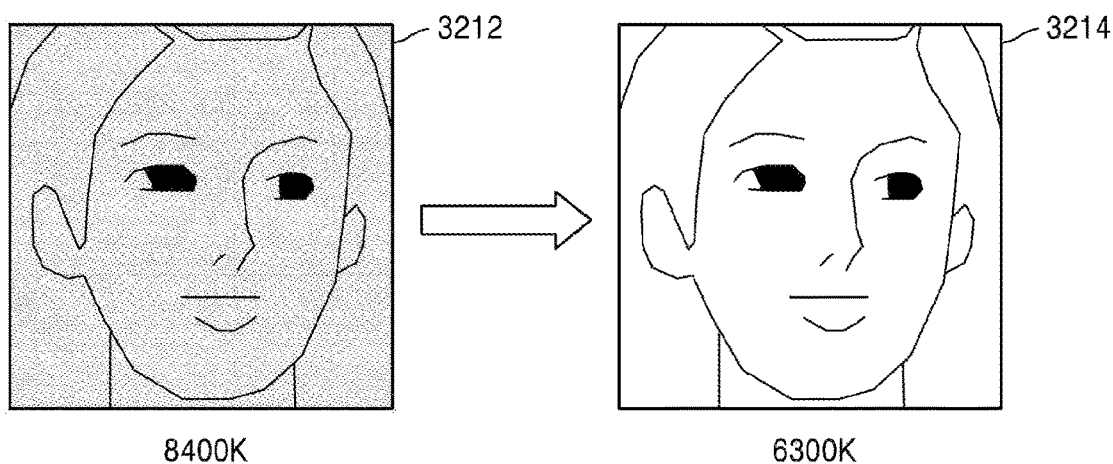

FIGS. 32A through 32C are diagrams for describing a method of normalizing, by the device 100, a hue value of a face region based on a base color temperature, according to an exemplary embodiment.

When types of illuminance on a face of a user are different, colors of the face in face images of the user may vary. A color temperature may be a numerical value expressing a color of illumination of an object by using a temperature of a black body having the same illumination as the illumination of the object.

For example, as shown in FIG. 32B, a fluorescent light having a color temperature of 4000 K shows a white object to be slightly red, a daylight of a daytime having a color temperature of 5200 K shows a white object to be white, and a cloudy day with clouds having a color temperature of 7000 K shows a white object to be slightly blue.

Accordingly, the same object may be red under a fluorescent light but blue under the sun. Thus, the color of the face of the user in the face image may vary based on illuminance on the face during photographing.

In operation S3210, the device 100 may obtain a color temperature of illumination on the face of the user while capturing the face of the user.

For example, the color temperature of the illumination obtained from a color temperature detecting sensor may be recorded on an input image as metadata, such as Exif information. The device 100 may obtain the color temperature of the illumination recorded on the input image from the metadata of the input image.

Alternatively, the device 100 may extract the color temperature of the illumination at a point of time when the input image is captured from the input image. For example, the device 100 may determine a brightest region of the input image as a region where an original white color is captured. By detecting the brightest region of the input image, the device 100 may detect an average hue value of the brightest region. Then, the device 100 may obtain the color temperature of the illumination corresponding to the hue value, based on the hue value. The device 100 may determine the color temperature of the illumination corresponding to the hue value as the color temperature of the illumination at the point of time when the input image is captured.

In operation S3220, the device 100 may adjust a hue value of the face image based on the color temperature of the illumination.

By obtaining the color temperature of the illumination, the device 100 may obtain a hue value shown when illumination having the obtained color temperature lights (i.e., illuminates) a white object, based on pre-stored information about color temperatures. Since a hue value is determined based on gains of red, green, and blue, the device 100 may determine gains of red, green, and blue corresponding to the hue value shown when the illumination having the obtained color temperature lights a white object.

The device 100 may exclude an effect of the color temperature of the illumination from the face image, based on the determined gains of red, green, and blue. For example, the device 100 may adjust the determined gains such that the white object is in original white. Also, the device 100 may exclude the effect of the color temperature of the illumination by adjusting gains of red, green, and blue of pixel values of the face image by the adjusted gains.

As such, by excluding the effect of the color temperature of the illumination from the face image, a hue value of the face of the user captured in a base color temperature may be obtained. According to an exemplary embodiment, such a method may be referred to as a white balance adjusting method.

Referring to FIG. 32C, the device 100 may normalize the hue value of the face image based on the base color temperature.

For example, when a color temperature of an input image 3212 is 8400 K and a base color temperature is 6300 K, the device 100 may normalize the color temperature of the input image 3212 to 6300 K by changing gains of red, green, and blue of pixel values of the input image 3212. By normalizing the color temperature of the input image 3212, the device 100 may determine a color of a face region in a normalized input image 3214 as a face color of a user.

Figure 32D:
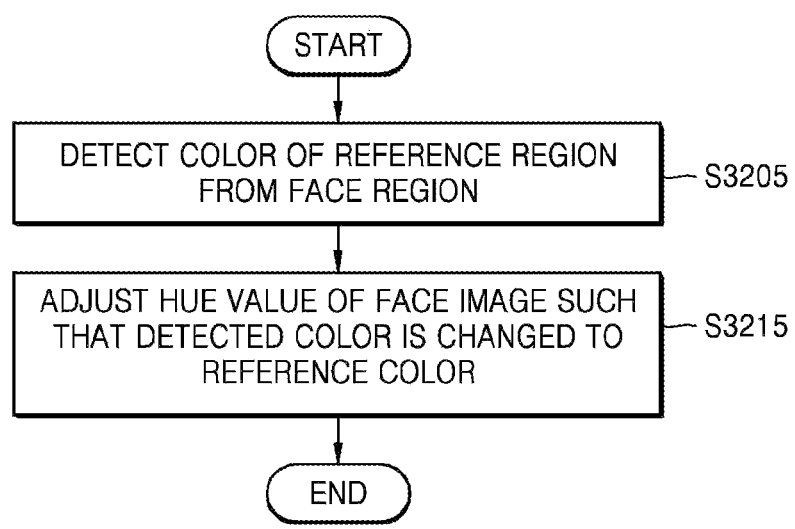
FIG. 32D is a flowchart of a method of normalizing, by a device, a color of a face in an input image based on a color of a base region, according to an exemplary embodiment.

FIG. 32D is a flowchart of a method of normalizing, by the device 100, a color of a face in an input image based on a color of a base region, according to an exemplary embodiment.

In operation S3205, the device 100 may detect the color of the base region from a face region.

The base region may be eyebrows, eyelashes, hair, a neck, or white regions of pupils, but is not limited thereto in one or more other exemplary embodiments. The device 100 may detect an area of the base region from the face region in an input image, and detect the color of the area.

In operation S3215, the device 100 may adjust a hue value of a face image such that the detected color is changed to a base color.

The base color may be pre-stored according to the base region. For example, base colors of eyebrows, eyelashes, and hair may be black, and base colors of white regions of pupils may be white.

The device 100 may adjust the hue value of the face region such that the color detected from the base region is changed to the base color. The device 100 may determine the color of the face region having the adjusted hue value to be a face color of a user.

Figure 32E:
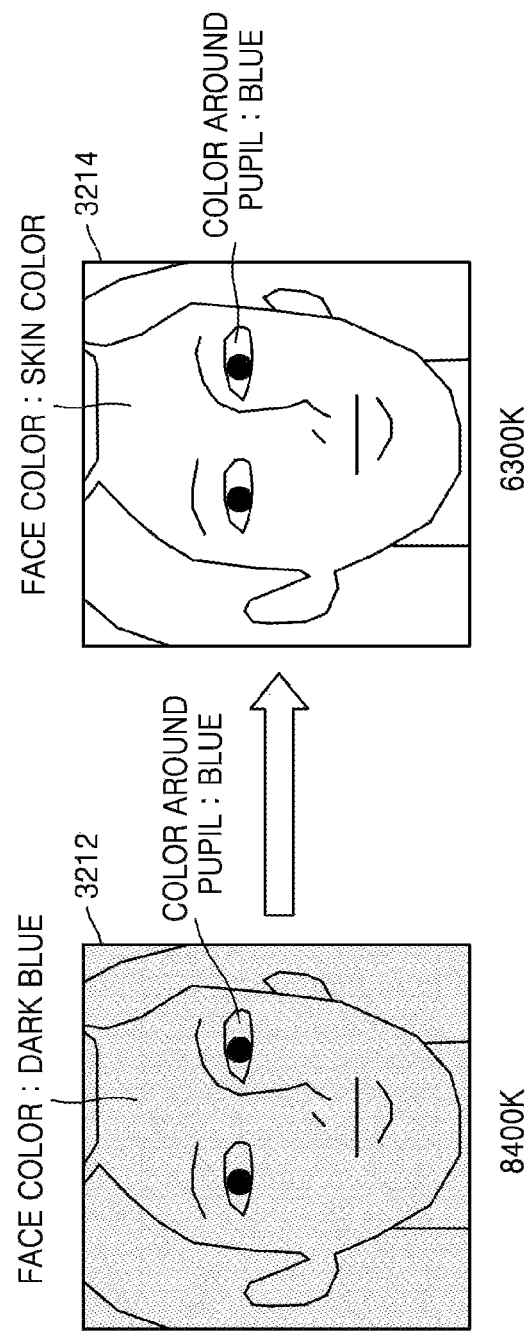
FIG. 32E is a diagram for describing a method of normalizing a color of a face in an input image based on a color of a base region, according to an exemplary embodiment.

FIG. 32E is a diagram for describing a method of normalizing, by the device 100, a color of a face in an input image based on a color of a base region, according to an exemplary embodiment.

Referring to FIG. 32E, when the base region is a white region of an eye, and a base color is white, the device 100 may determine an area of the white region of the eye in the input image 3212, and determine a color of the determined area. When the color of the determined area is blue, the device 100 may adjust a hue value of the input image 3212 such that the color of the determined area is white.

By adjusting the hue value of the input image 3212, a face color in the input image 3212 may be changed from dark blue to a skin color.

Figure 33:
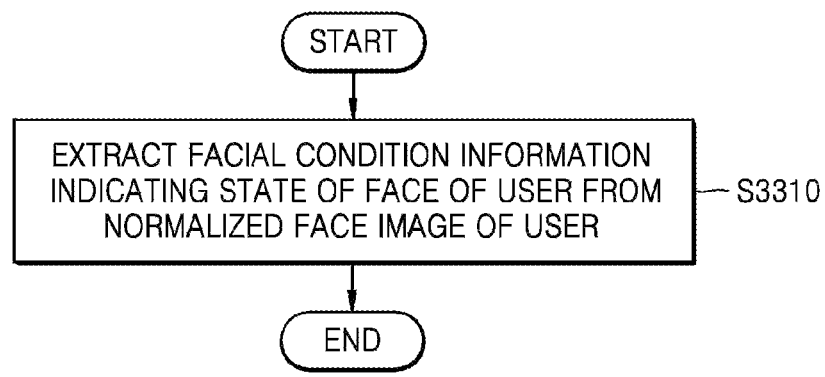
FIG. 33 is a flowchart of a method of extracting, by a device, facial condition information indicating a condition of a face of a user, from a normalized face image of the user, according to an exemplary embodiment.

FIG. 33 is a flowchart of a method of extracting, by the device 100, facial condition information indicating a condition of a face of a user, from a normalized face image of the user, according to an exemplary embodiment.

In operation S3310, the device 100 may extract the facial condition information indicating the condition of the face of the user from the normalized face image of the user.

The facial condition information may be a base state of a face for determining health information.

By normalizing a face image, the device 100 may determine a region from which the facial condition information is to be extracted from the normalized face image. For example, the device 100 may determine locations of regions under eyes, a nose region, and a region around a mouth in the face image.

After determining the region from which the facial condition information is to be extracted, the device 100 may extract the facial condition information from the region. For example, the device 100 may determine whether the regions under the eyes are swollen. Alternatively, the device 100 may determine whether colors of the regions under the eyes are darker than before.

A method of determining the location of the region from which the facial condition information is to be extracted, a symptom to be checked, and a method of checking the symptom may be stored in the device 100. Accordingly, the device 100 may determine whether the symptom is shown in the region from which the facial condition information is to be extracted.

A symptom shown on a face when a body malfunctions may be shown on a certain region of the face. For example, when hyperthyroidism or an allergic disease or reaction is generated, fat under the eyes may increase. Also, for example, when allergic rhinitis is generated, a dark circle may be generated under the eyes.

The device 100 may store symptom information according to regions of the face. For example, the device 100 may store information about whether the regions under the eyes are swollen or are darker as the symptom information according to the regions under the eyes.

Accordingly, the device 100 may determine the regions under the eyes from among entire regions of the face as the region from which the facial condition information is to be extracted, and extract the information about whether the regions under the eyes are swollen or are darker from the regions under the eyes, as the facial condition information.

Figure 34:
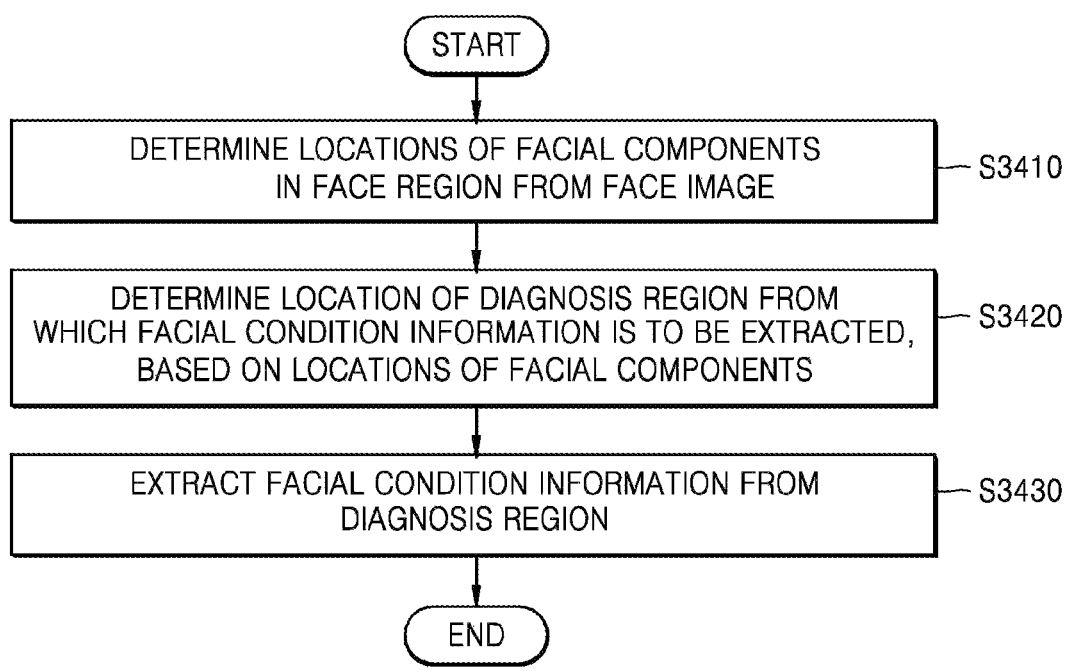
FIG. 34 is a flowchart of a method of extracting, by a device, facial condition information shown on a face from a normalized face image, according to an exemplary embodiment.

FIG. 34 is a flowchart of a method of extracting, by the device 100, facial condition information shown on a face from a normalized face image, according to an exemplary embodiment.

In operation S3410, the device 100 may determine locations of facial components in a face region from a face image.

The facial components may include at least one of eyes, a nose, and a mouth. The device 100 may determine the locations of the facial components from the face image in any one of various methods.

For example, by using features that brightness of eyes, eyebrows, and a mouth are darker than other facial components of a face, the device 100 may binarize the face image and determine locations of darker regions as the locations of the eyes, the eyebrows, and the mouth.

Alternatively, the device 100 may extract a skin color region from the face image and determine the locations of the eyes, the eyebrows, and the mouth from the extracted skin color region.

Alternatively, since the locations of the eyes, the eyebrows, the nose, and the mouth show a certain pattern in the face, the device 100 may determine the locations of the facial components by using an active appearance model (AAM) method in which locations of facial components are determined based on a facial pattern.

In operation S3420, the device 100 may determine a location of a diagnosis region from which facial condition information is to be extracted, based on the locations of the facial components.

The diagnosis region may be pre-stored in the device 100. For example, a forehead, a region under an eye, a nose, a region around a mouth, or a chin region may be set as the diagnosis region in the device 100.

Also, a method of determining the location of the diagnosis region may be pre-stored in the device 100. For example, a nose region may be determined to be a triangular region connecting two end points of sides of a nose and a starting point of the nose. The method of determining the location of the diagnosis region will be described in detail below with reference to FIG. 35.

In operation S3430, the device 100 may extract facial condition information from the diagnosis region.

The facial condition information may be extracted by analyzing the face image. For example, the device 100 may extract the facial condition information by using color information of the face region in the face image, a face recognition algorithm, or a facial expression recognition algorithm. A type of facial condition information extractable according to the diagnosis region and a method of extracting the facial condition information may be pre-stored in the device 100.

The device 100 may extract information about a color of the face, a number of blemishes or pimples, an eye color, or a lip color by using color information of the face region. Also, for example, the device 100 may extract information about an inflamed eye, a pupil size, movement of a pupil, a face size, a shape of a face contour, a cracked lip, a location of each organ of the face, and movement of facial muscles, by using the face recognition algorithm or the facial expression recognition algorithm. Any other algorithms or methods may be used to extract the facial condition information.

A skin condition may be determined by using the color of the face, the number of blemishes or pimples, and the shape of the face contour. For example, the skin condition may be determined to be bad when the color of the face is dark, the number of blemishes or pimples is high, and the shape of the face contour is loose.

An eye condition may be determined by using at least one of the inflamed eye, the eye color, the pupil size, and the movement of the pupil. For example, when the eyes are inflamed, the white regions of the eyes are dark, and a reaction speed of the pupils is slow, the device 100 may determine that the eye condition is bad. Also, the device 100 may determine that a liver is bad or eyes are infected based on the color of the white regions of the eyes.

A weight change may be determined based on at least one of the face size and the shape of the face contour. For example, it may be determined that a weight increased if the face size increased and a face contour of a cheek portion from among the face counter moved outward compared to a previously captured face image.

A lip condition may be determined by using at least one of the lip color and whether the lip is cracked. For example, when the lip is red, has high saturation, and is not cracked, it is determined that the lip condition is good, and when the lip has low saturation or is blue and is cracked, it is determined that the lip condition is bad. Also, the device 100 may determine malfunction of the body based on whether the lip is dark red, blue, or skin color, and whether the saturation of the lip is low.

A hair condition may be determined by using at least one of a hair color, gloss of the air, and whether the hair is damaged. For example, when the hair color is dark, the hair is glossy and is not damaged, the device 100 may determine that the hair condition is good, and otherwise, determine that the hair condition is bad. The gloss of the hair may be determined by detecting a bright region shown in a curved region of a hair region.

A body condition may be determined by gathering or determining at least one of the skin condition, the eye condition, the lip condition, the hair condition, and the movement of the facial muscles. For example, the device 100 may determine that the body condition is good when the eye condition, the lip condition, the hair condition, and the movement of the facial muscles are good.

FIGS. 35A and 35B are diagrams for describing a method of determining, by the device 100, a location of a diagnosis region, according to an exemplary embodiment.

Referring to FIG. 35A, the device 100 may determine locations of facial components in a face image.

For example, the device 100 may determine end points 3420 through 3426 of eyes, end points 3410 through 3416 of eyebrows, side points 3430 and 3432 of a nose, end points 3440 and 3442 of a lip, an end point 3434 of the nose, and a starting point 3436 of the nose.

Referring to FIG. 35B, the device 100 may determine the location of the diagnosis region based on the locations of the facial components.

For example, a forehead, regions under the eyes, the nose, a region around a mouth, and a chin region may be set as diagnosis regions in the device 100.

Also, a method of determining the location of each diagnosis region may be set in the device 100. For example, a nose region may be determined to be a triangular region 3450 connecting the side points 3430 and 3432 of the nose and the starting point 3436 of the nose. Also, an upper boundary of a region 3460 around the mouth 3460 may be determined to be a Y-axis coordinate of a center point 3446 between the end point 3434 of the nose and a center point 3444 of the lip.

Figure 36A:
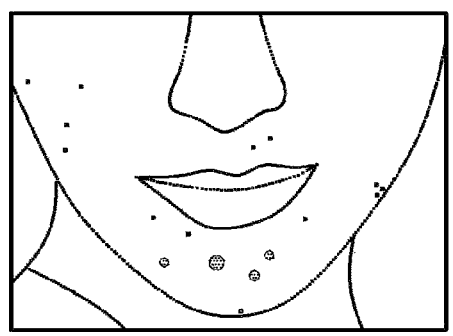
FIGS. 36A and 36B are diagrams for describing a method of extracting, by a device, facial condition information from a diagnosis region, according to an exemplary embodiment.
Figure 36B:
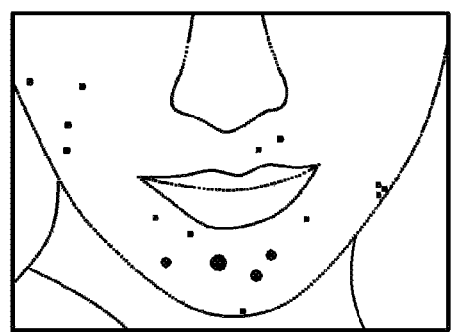

FIGS. 36A and 36B are diagrams for describing a method of extracting, by the device 100, facial condition information from a diagnosis region, according to an exemplary embodiment.

Referring to FIGS. 36A and 36B, the device 100 may extract the facial condition information corresponding to the diagnosis region from the diagnosis region.

At least one of a lip color and whether a pimple is generated in a region around a mouth may be set as symptoms in the device 100 correspondingly to a mouth region.

Referring to FIG. 36A, the device 100 determines a location of a lip region, and extract a hue value or saturation value of the lip from the lip region as facial condition information. For example, the device 100 may extract the hue value of the lip by averaging hue values of pixels forming the lip region.

Alternatively, the device 100 may determine a location of the region around the mouth, and extract a skin trouble level from the region as facial condition information.

Referring to FIG. 36B, the device 100 may use any of various image processing methods in order to detect pimples on a skin.

For example, the device 100 may emphasize pimples compared to the skin by increasing contrast of the region. Here, since pimples or skin troubles are darker than a normal skin, the device 100 may binarize the region and determine locations of the pimples or skin troubles in the binarized region. Alternatively, since the pimples or skin troubles are red, locations of pixels showing a red color may be determined as the locations of the pimples or skin troubles.

The device 100 may determine whether the number of pimples or skin troubles increased or decreased based on a change of areas the pimples or skin troubles are generated.

Figure 37:
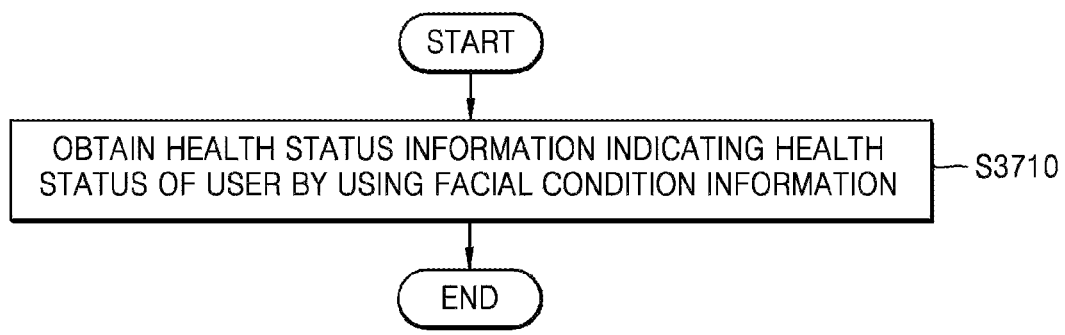
FIG. 37 is a flowchart of a method of obtaining, by a device, health status information related to health of a user based on facial condition information, according to an exemplary embodiment.

FIG. 37 is a flowchart of a method of obtaining, by the device 100, health status information related to health of a user based on facial condition information, according to an exemplary embodiment.

In operation S3710, the device 100 may obtain the health status information indicating a health status of the user by using the facial condition information.

The device 100 may obtain the health status information by using the facial condition information extracted from a diagnosis region in a face image.

The health status information may include information about a disease of the user, an organ having a deteriorated function, or a condition of the user, which are predicted from the facial condition information. The health status information may be stored in the device 100.

The device 100 may obtain the health status information from the facial condition information by considering photographing circumstance information obtained while capturing a face of the user. The photographing circumstance information may include a photographed time, a photographed place, activity of the user during photographing, and bio-information of the user obtained during photographing.

Also, the device 100 may obtain the health status information from the facial condition information by considering at least one of a physical condition, such as a height, a weight, an age, a gender, or a medical history, such as a current disease or a past disease, of the user.

FIGS. 38A and 38B are tables for describing a method of extracting, by the device 100, health status information of a user based on facial condition information extracted from a face image, according to an exemplary embodiment.

Referring to FIG. 38A, the device 100 may store information about a predicted disease according to a face color.

Accordingly, the device 100 may determine that a liver is malfunctioning when a face is dark blue, a kidney is malfunctioning when a face is black, a lung is malfunctioning when a face is white, and a heart is malfunctioning when a face is red.

Referring to FIG. 38B, the device 100 may store information about predicted diseases or causes of symptoms according to symptoms extracted from diagnosis regions.

Accordingly, the device 100 may determine a predicted disease or a cause of a symptom based on a symptom extracted from each diagnosis region. For example, when facial condition information extracted from eyes is that the eyes are inflamed, the device 100 may determine that a liver and a heart are malfunctioning.

Figure 39:
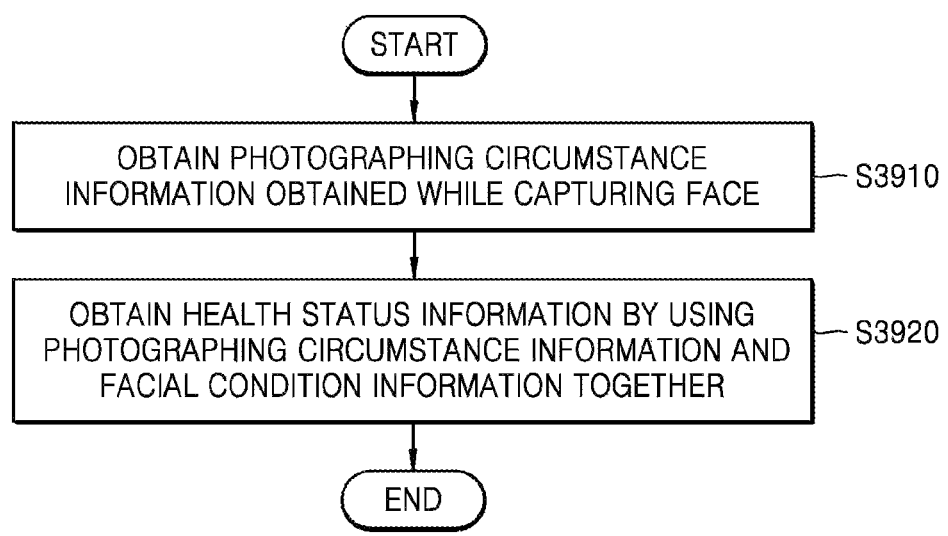
FIG. 39 is a flowchart of a method of obtaining, by a device, health status information from facial condition information by considering photographing circumstance information obtained while capturing a face, according to an exemplary embodiment.

FIG. 39 is a flowchart of a method of obtaining, by the device 100, health status information from facial condition information by considering photographing circumstance information obtained while capturing a face, according to an exemplary embodiment.

In operation S3910, the device 10 may obtain the photographing circumstance information obtained while capturing the face.

The photographing circumstance information may be stored in a file of an input image in a form of metadata of the input image. Alternatively, the device 100 may store the photographing circumstance information according to ID information of the input image, while generating the input image.

The photographing circumstance information may include at least one of a photographed time, a photographed place, an activity of a user during photographing, and bio-information of the user obtained during photographing.

In operation S3920, the device 100 may obtain the health status information related to health of the user while considering the facial condition information and the photographing circumstance information together.

For example, when a photographed time of the face is 3:00 am, the device 100 may determine that, even if a facial condition extracted from a face image is much lower than a pre-set standard, such a facial condition is due to temporary overwork. In this case, the device 100 may determine a degree of the extracted facial condition to be lighter while obtaining the health status information from the facial condition information.

Alternatively, for example, when a photographed time is dawn, the device 100 may determine that the face is not made up, and obtain the health status information by assigning a weight compared to other time zones.

Alternatively, for example, when sleeping hours of the user is 2 hours when the face is captured, the device 100 may determine that, even if the facial condition extracted from the face image is much lower than the pre-set standard, such a facial condition is due to temporary overwork. In this case, the device 100 may determine a degree of the extracted facial condition to be lighter while obtaining the health status information from the facial condition information.

Alternatively, for example, when a photographed place is a bar and a symptom extracted from the face image is a flush, the device 100 may determine that the flush is due to temporary drinking, and obtain the health status information by excluding the symptom of flush.

Alternatively, the device 100 may determine a biological condition of the user at a point of time when the input image is captured based on bio-information at the point of time when the input image is captured, and exclude information shown on the face of the user due to the biological condition from the facial condition information.

For example, when a pulse rate of the user is higher than normal, the device 100 may determine that the face is captured immediately after an exercise, and exclude a face color of the user from the facial condition information.

Alternatively, for example, when an activity amount of the user is high when the face is captured, a heart rate is high, or a symptom extracted from the face image is a flushed face, the device 100 may determine that the flushed face is due to a temporary exercise, and obtain the health status information by excluding the symptom of the flushed face from the facial condition information.

Figure 40:
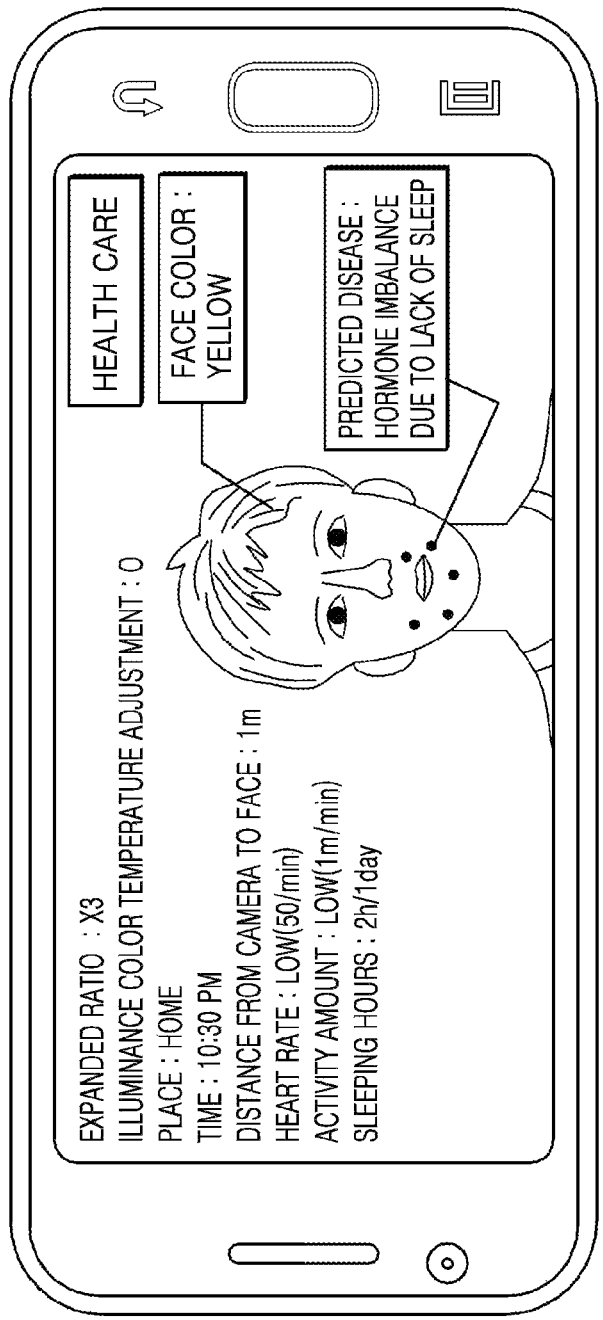
FIG. 40 is a diagram for describing a method of displaying photographing circumstance information obtained while capturing an image, together with health status information of a user, according to an exemplary embodiment.

FIG. 40 is a diagram for describing a method of displaying photographing circumstance information obtained while capturing an image, together with health status information of a user, according to an exemplary embodiment.

Referring to FIG. 40, the device 100 displays a face image on a screen, and displays the health status information of the user extracted from the displayed face image. Also, the device 100 may display the photographing circumstance information considered while extracting the health status information from the face image, together with the health status information.

The device 100 may consider at least one of a photographed place, a photographed time, a distance from a camera to the face, a heart rate during photographing, an activity amount during photographing, and sleeping hours during photographing, while extracting the health status information from the face image.

Also, the device 100 may display an image processing method applied to an original input image in order to extract the health status information from the original input image. For example, the device 100 may display information about an expanded ratio or whether illumination is adjusted.

Figure 41A:
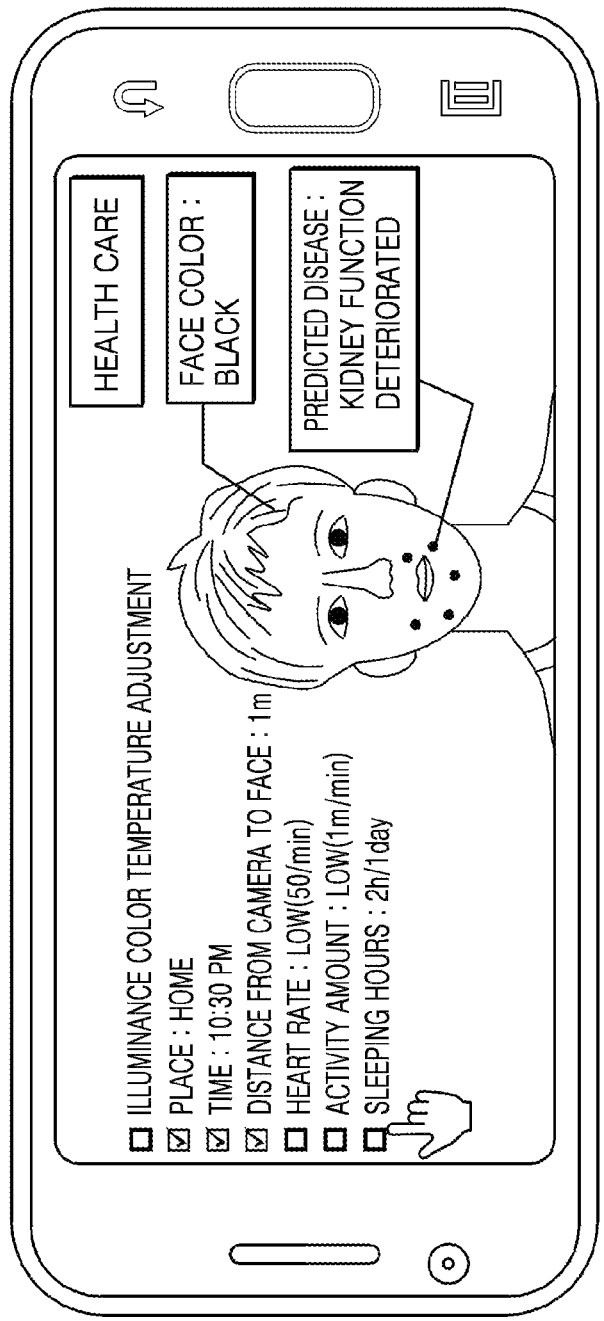
FIGS. 41A and 41B are diagrams for describing a method of providing, by a device, a function of selecting photographing circumstance information to be considered by the device from among a plurality of pieces of photographing circumstance information, while obtaining health status information from facial condition information, according to an exemplary embodiment.
Figure 41B:
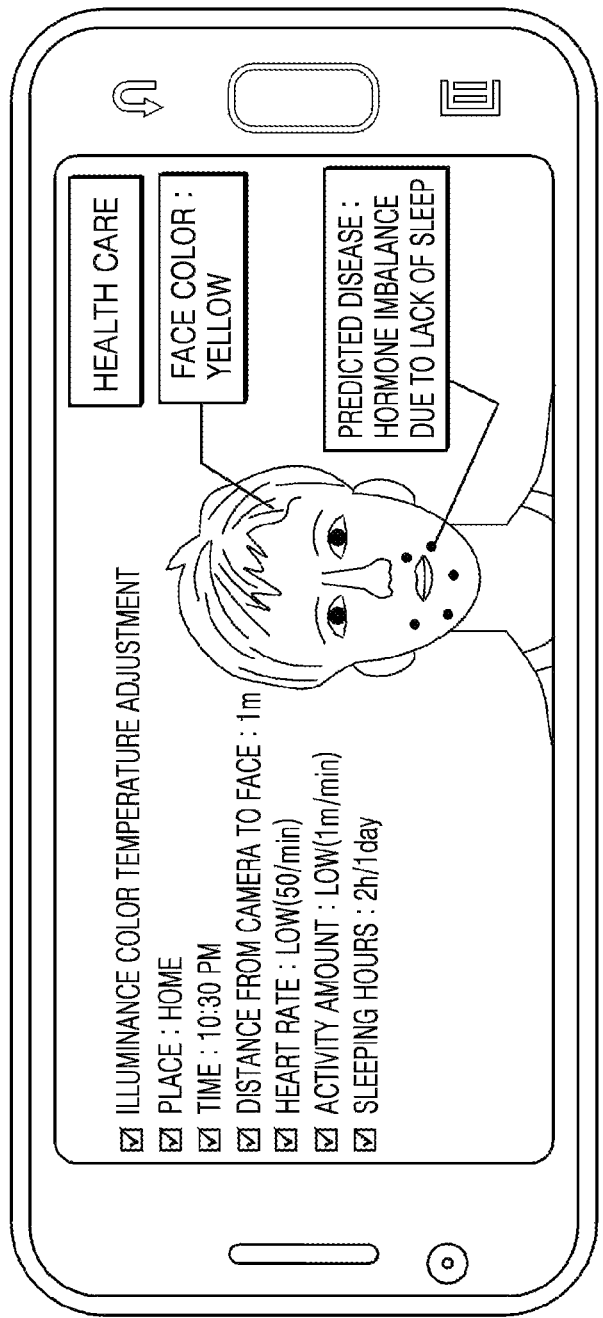

FIGS. 41A and 41B are diagrams for describing a method of providing, by the device 100, a function of selecting photographing circumstance information to be considered by the device 100 from among a plurality of pieces of photographing circumstance information, while obtaining health status information from facial condition information, according to an exemplary embodiment.

The device 100 may display a user interface for selecting the photographing circumstance information to be considered while obtaining the health status information from the facial condition information. Based on a user input of selecting at least one of the plurality of pieces of photographing information displayed on the screen, the device 100 may obtain the health status information from the facial condition information based on the selected photographing circumstance information.

Alternatively, the device 100 may display a user interface for selecting an image processing method to be applied to a face image while obtaining the health status information from the facial condition information. Based on a user input of selecting at least one of image processing methods displayed on the screen, the device 100 may adjust the face image based on the selected at least one image processing method, and obtain the facial condition information from the adjusted face image.

Referring to FIG. 41A, the device 100 may extract skin troubles around a mouth as the facial condition information from the face image. Also, the device 100 may determine that a face color in the face image is black. The device 100 may obtain deterioration of a kidney function as the health status information based on the skin troubles around the mouth and the black face color.

Referring to FIG. 41B, the device 100 may display a user interface for adjusting a color temperature of illumination on the face image, and a user interface for considering at least one of a heart rate, an activity amount, and sleeping hours when the health status information is obtained.

Upon receiving user inputs of adjusting the color temperature of the illumination and selecting the heart rate, the activity amount, and the sleeping hours, the device 100 may determine a hue value of the face image by considering the color temperature of the illumination.

By adjusting the hue value of the face image, the device 100 may change the face color from black to yellow. Then, by considering the yellow face color and that the sleeping hours is 2 hours during photographing, the device 100 may obtain the health status information indicating that the skin trouble around the mouth is caused by hormone imbalance due to lack of sleep, instead of deterioration of a kidney function.

Figure 42:
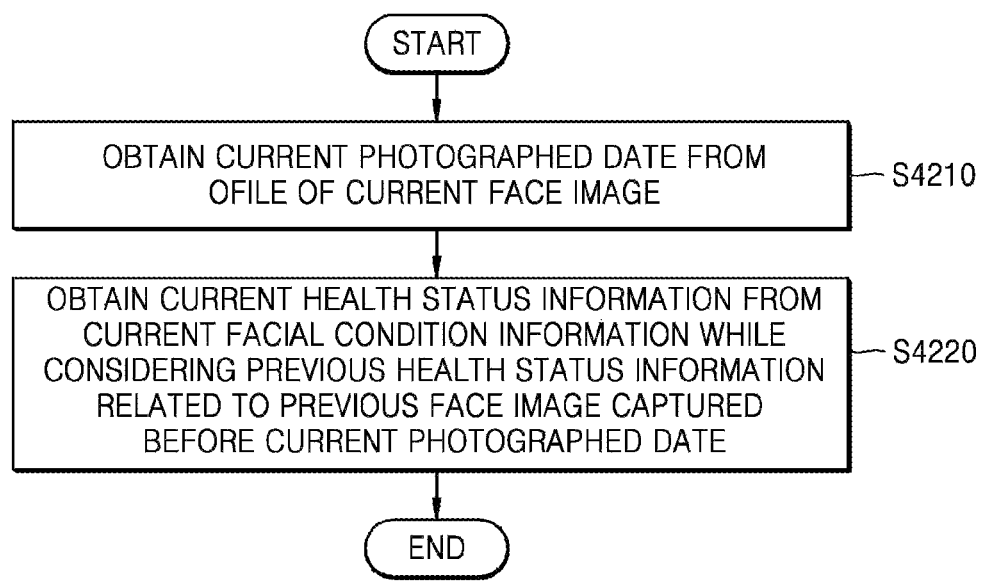
FIG. 42 is a flowchart of a method of obtaining, by a device, health status information from facial condition information based on a point of time when a face image is captured, according to an exemplary embodiment.

FIG. 42 is a flowchart of a method of obtaining, by the device 100, current health status information from current facial condition information based on a point of time when a current face image is captured, according to an exemplary embodiment.

In operation S4210, the device 100 may obtain a current photographed date from a file of the current face image.

For example, the current photographed date may be recorded in the current face image in a form of metadata. Accordingly, the device 100 may obtain the current photographed date from the metadata of the current face image.

In operation S4220, the device 100 may obtain the current health status information from the current facial condition information while considering previous health status information related to a previous face image that is captured before the current photographed date.

The device 100 may extract previous facial condition information from a plurality of pre-obtained face images of a user. Upon extracting the previous facial condition information from the plurality of pre-obtained face images, the device 100 may store previous health status information obtained from the previous facial condition information according to previous photographed dates of the plurality of pre-obtained face images. Accordingly, the device 100 may obtain the previous health status information of the user according to the previous photographed dates.

The device 100 may obtain the previous health status information related to the previous face image that is captured before the current photographed date obtained in operation S4210. The device 100 may obtain the previous health status information of the previous face image based on health statuses of the user according to the previous photographed dates.

Accordingly, the device 100 may obtain a disease or an abnormality of the user before the point of time the current face image is captured.

Upon obtaining the previous health status information before the current photographed date, the device 100 may obtain the current health status information from the current facial condition information of the current face image while considering the previous health status information before the photographed date.

The device 100 may obtain the current health status information from the current facial condition information based on the disease or the abnormality of the user before the current photographed date.

When a symptom extracted from the current face image is determined to be a result of a plurality of diseases or abnormalities, the device 100 may determine the current health status information based on the previous health status information extracted from the plurality of pre-obtained face images.

For example, when a disease or an abnormality extracted from previous face images obtained for a month before a current photographed date of a current face image is gastroenteritis, and gastroenteritis, overwork, or drinking is extracted as a cause of current facial condition information extracted from the current face image, the device 100 may determine that a cause of a current symptom is gastroenteritis.

Also, when a number of times the disease or the abnormality is shown before the current photographed time is lower than a reference number, the device 10 may not determine the disease or the abnormality as the health status information.

Also, the device 100 may determine whether a certain disease is worse or improved based on the previous health status information extracted from the previous face images.

Health status information extracted from temporally consecutive face images may be similar. For example, health status information extracted from a face of the same person, which is captured for one month, may show similar diseases or abnormalities. Thus, the device 100 may obtain accurate health status information from facial condition information by using diseases or abnormalities a user had before a point of time a current face image is captured.

Figure 43:
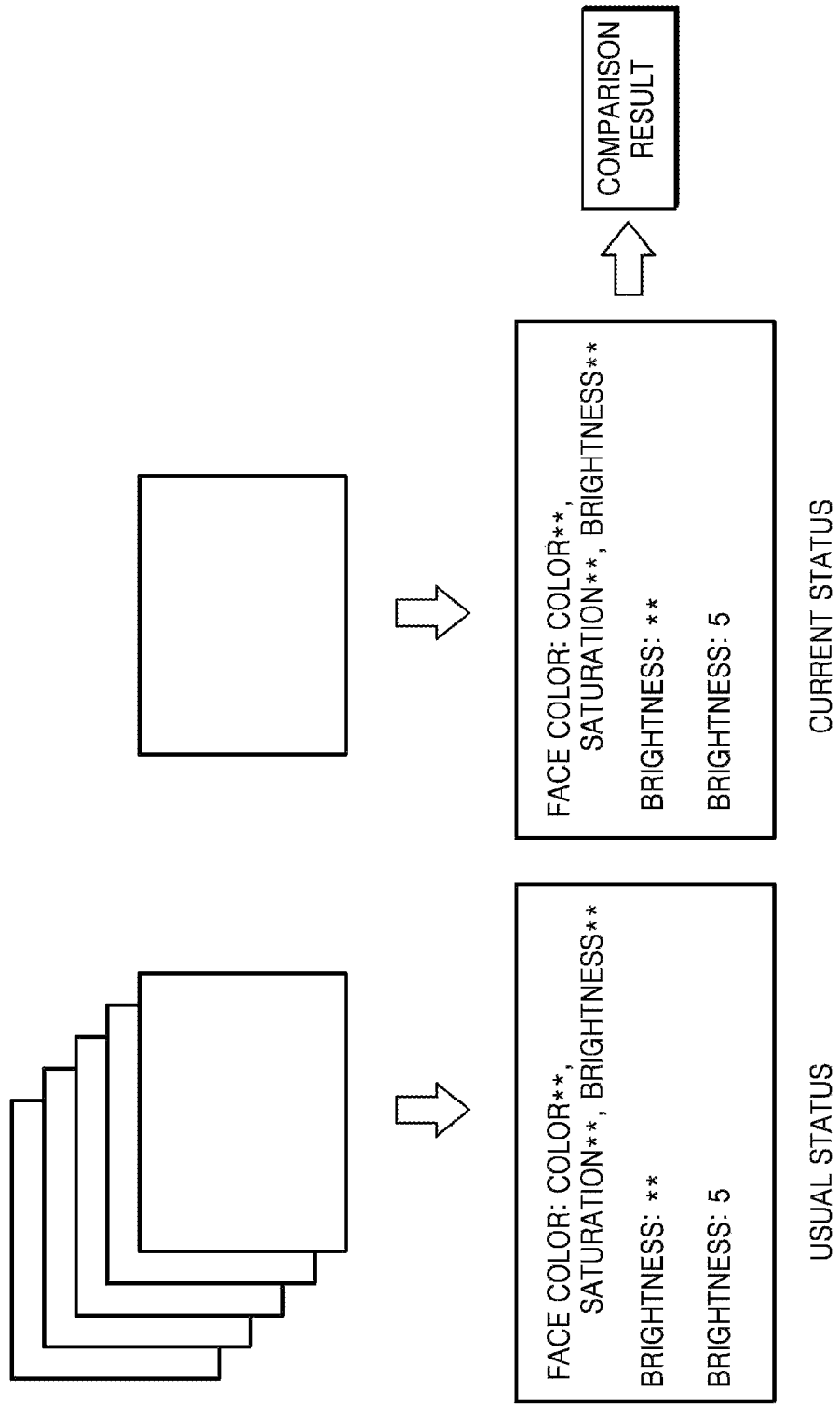
FIG. 43 is a diagram for describing a process of obtaining, by a device, health status information, according to an exemplary embodiment.

FIG. 43 is a diagram for describing a process of obtaining, by the device 100, current health status information, according to an exemplary embodiment.

According to an exemplary embodiment, the device 100 may obtain the current health status information by comparing a usual (e.g., reference) status and a current status. For example, the device 100 may extract previous facial condition information from previous face images of a user captured and stored in the past, and calculate the usual status of the user by calculating an average value of the previous facial condition information.

Also, the device 100 may calculate the current status of the user by extracting current facial condition information from a current face image. The usual status and the current state may be calculated according to types of facial condition information. Examples of the types of the facial condition information include at least one of a face color, a number or sizes of blemishes or pimples, an inflamed eye, an eye color, a pupil size, movement of a pupil, a face size, a shape of a face contour, a lip color, a cracked lip, a location of each organ (eyes, a nose, a mouth, ears, or eyebrows) of a face, an hair color, glass of hair, damaged hair, and movement of facial muscles.

Based on a result of comparing the usual status and the current status, the device 100 may evaluate a current health status according to the types of the facial condition information or by gathering a result of comparing the facial condition information.

According to another exemplary embodiment, the device 100 may obtain the current health status information by calculating a difference between a pre-stored normal status and the current status. For example, the normal status of facial condition information may be defined based on at least one of an age of the user, a gender of the user, a height of the user, a weight of the user, a time zone, and weather.

The device 100 may calculate the difference between the pre-stored normal status and the current state according to the types of the facial condition information. Based on a result of comparing the pre-stored normal status and the current status, the device 100 may evaluate the current health status according to the types of the facial condition information or by gathering (e.g., obtaining) a result of comparing the facial condition information.

According to an exemplary embodiment, an operation of obtaining and providing the current health status information may be performed while a function of a photo album or a gallery of the device 100 is being executed. For example, when the user selects images to be used as face images from among images stored in a photo album and executes a health examination function of the device 100, the device 100 may calculate and provide health status information from the selected face images.

Alternatively, when the user executes the health examination function while the photo album is being executed, the device 100 may extract face images satisfying a face image obtaining condition from the images stored in the photo album, and calculate and provide health status information by using the extracted face images. In this case, the face images may be classified according to users and provide health status information of each user.

Alternatively, the device 100 may provide a list of people included in face images, and obtain and provide health status information of a person selected by the user.

According to another exemplary embodiment, an operation of obtaining and providing the current health status information may be performed while a certain application is being executed in the device 100. For example, the user may obtain the current health status information by executing an application having a health examination function.

According to an exemplary embodiment, the current health status information may be calculated by the device 100. In this case, the device 100 may use a certain algorithm to calculate the current health status information.

When the current health status information is calculated, the device 100 provides the current health status information to the user. The current health status information may be provided to the user via any of various methods, such as at least one of displaying, outputting audio, outputting to an external device, or storing in a memory.

According to one or more exemplary embodiments, the device 100 may display the current face image and the current health status information on one screen, or display only the current health status information.

Figure 44A:
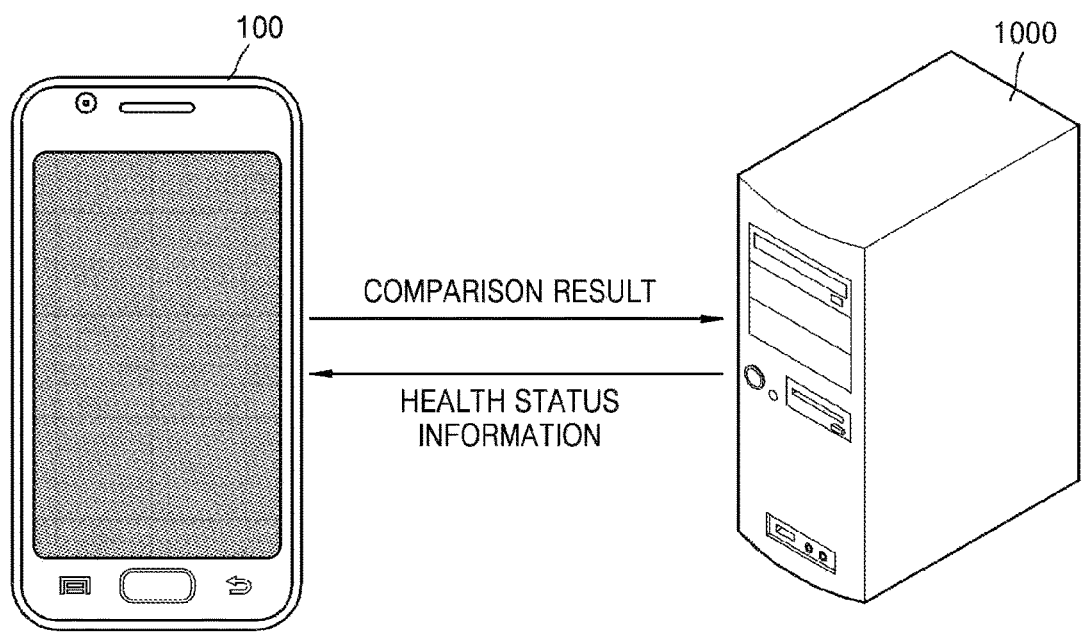
FIG. 44A is a diagram for describing a method of obtaining, by a device, health state information by using a service server, according to an exemplary embodiment.

FIG. 44A is a diagram for describing a method of obtaining, by the device 100, health state information by using a service server 1000, according to an exemplary embodiment.

Referring to FIG. 44A, the device 100 may obtain the health status information of the user from the face image by using the service server 1000.

At least one of address information of the service server 1000 and account information of the user registered in the service server 1000 may be stored in the device 100. The address information of the service server 1000 may include an Internet Protocol (IP) address of the service server 1000.

The device 100 may transmit the face image of the user to the service server 1000 based on the address information of the service server 1000. At this time, the device 100 may extract only a facial region of the user from an input image and transmit only the face region to the service server 1000, or alternatively, may transmit the input image including the face of the user to the service server 1000. Also, at this time, the device 100 may transmit the account information of the user registered in the service server 1000 to the service server 1000. The device 100 may periodically transmit the face image to the service server 1000, or may transmit the face image based on a user input.

Upon receiving the face image and the account information from the device 100, the service server 1000 may obtain feature information of the face of the user, which is stored correspondingly to the account information, and determine a location of the face region in the face image based on the feature information.

By determining the location of the face region in the face image, the service server 1000 may obtain the facial condition information of the user by analyzing the face region in the face image. At this time, the service server 1000 may obtain the facial condition information by comparing the face image with a reference image that is stored correspondingly to the account information of the user. The reference image may be a previous face image of the user, which is captured before a point of time the face image was captured. Also, the reference image may be automatically selected by the service server 1000 or may be determined based on user's selection.

Upon obtaining the facial condition information, the service server 1000 may obtain the health status information of the user based on the facial condition information.

The service server 1000 may store the facial condition information and the health status information according to the account information of the user. Also, the service server 1000 may transmit the facial condition information and the health status information to the device 100.

FIG. 44B illustrates a database 4400 of users, which is stored in the service server 1000, according to an exemplary embodiment.

Referring to FIG. 44B, the service server 1000 may store information about users correspondingly to account information 4410 of the users.

The information about the users may include at least one of feature information 4420 of faces of the users for extracting face regions from face images, ID information 4430 of reference images that are to be compared with the face images to extract facial condition information 4440, the facial condition information 4440 of the users, and health status information 4450 of the users, but is not limited thereto in one or more other exemplary embodiments.

Figure 44C:
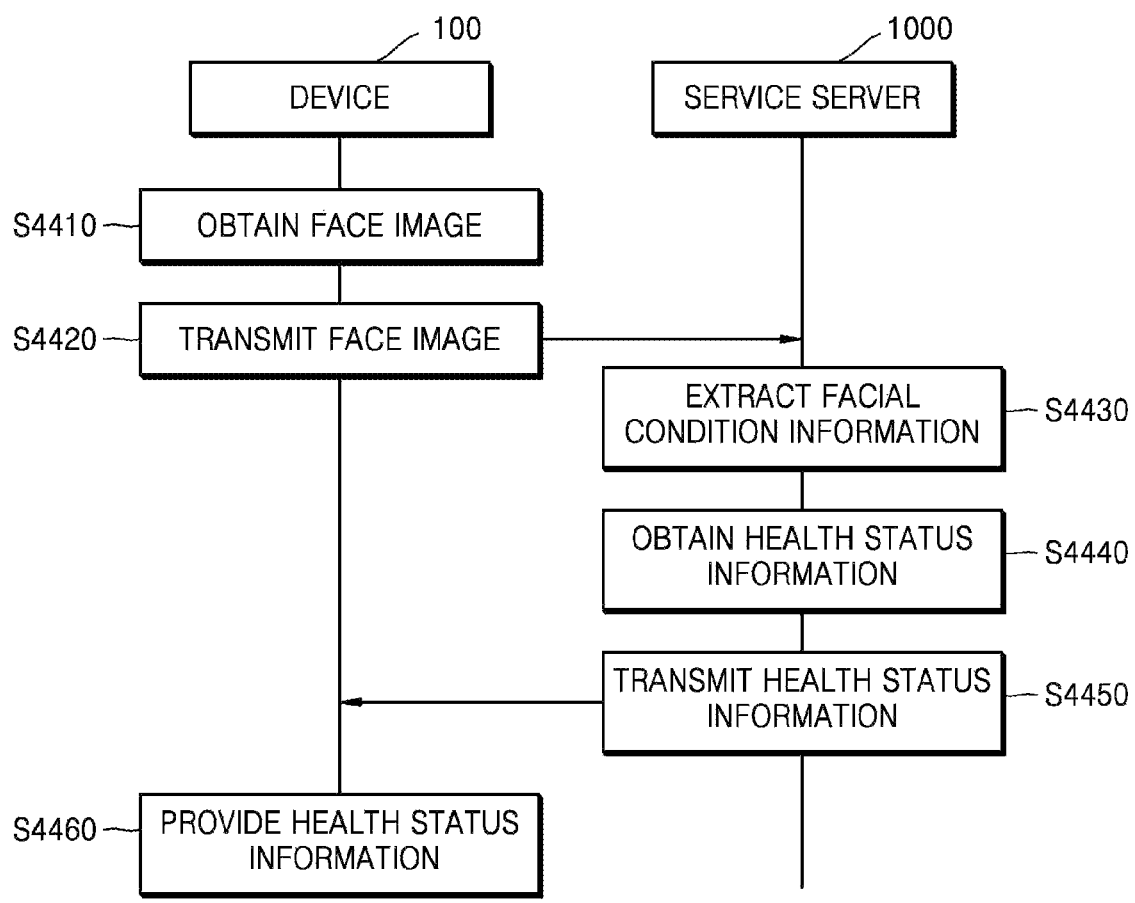
FIG. 44C is a flowchart of a process of obtaining, by a device, health status information by using a service server, according to an exemplary embodiment.

FIG. 44C is a flowchart of a process of obtaining, by the device 100, health status information by using the service server 1000, according to an exemplary embodiment.

According to the current exemplary embodiment, the process of obtaining the health status information may be performed by the service server 1000 communicating with the device 100. The service server 1000 may be, for example, a server that provides a service of obtaining health status information, and may be a medical service server, an application server, or a website server.

The device 100 obtains a face image in operation S4410. Then, the device 100 transmits the face image to the service server 1000 in operation S4420. The device 100 may access the service server 1000 via the Internet, a telephone network, or a wireless communication network. For example, when the device 100 is a mobile communication terminal, the device 100 may access a network by using a mobile communication method, such as WiFi, third generation mobile communication, fourth generation mobile communication, long term evolution (LTE), or long term evolution-advanced (LTE-A), and access the service server 1000. Also, according to one or more exemplary embodiments, the device 100 may transmit a face image to the service server 1000 via any of various methods, for example, transmit a face image from a photo album to the service server 1000, transmit a face image in an application to the service server 1000, transmit a face image to the service server 1000 through a short message service (SMS), transmit a face image to the service server 1000 by using a messenger application, and transmit a face image to the service server 1000 via an email.

According to an exemplary embodiment, the device 100 may transmit an image file of the face image to the service server 1000. In this case, the service server 1000 may extract ID information of the face image included in the image file. The service server 1000 may store face feature point information according to ID information, and extract the ID information of the face image by using the stored face feature point information. Also, according to an exemplary embodiment, the service server 1000 may search for information stored in the service server 1000 with respect to the extracted ID information. For example, the service server 1000 may store at least one of facial condition information, health status information, personal information, medical history information and another face image with respect to the ID information, and search for such information by using the ID information.

According to another exemplary embodiment, the device 100 may transmit the image file and the ID information of the face image to the service server 1000. The ID information may include, for example, at least one or a combination of an ID, a phone number, an IP address, and a media access control (MAC) address. The service server 1000 may search for the facial condition information, the health status information, the personal information, the medical history information, and the other face image stored in the service server 1000 and corresponding to the ID information, by using the ID information.

According to another exemplary embodiment, the device 100 may transmit the image file of the face image, the ID information, and the facial condition information and the health status information with respect to the ID information to the service server 1000. According to another exemplary embodiment, the device 100 may transmit the personal information and additional information with respect to the ID information to the service server 1000, together with the image file. The personal information may be at least one of information about a name, a contact number, or an occupation. The additional information may be information about at least one of a medical record, a medical history, a height, a weight, an age, blood pressure, blood sugar, a waist measurement, a hip circumference, a chest size, etc.

Upon receiving the face image in operation S4420, the service server 1000 extracts facial condition information from the face image in operation S4430. The facial condition information may be extracted by analyzing the face image. For example, the service server 1000 may extract the facial condition information by using at least one of color information of a face region, a face recognition algorithm, or a facial expression recognition algorithm. For example, the service server 1000 may extract information about at least one of a face color, a number of blemishes or pimples, an eye color, or a lip color, by using the color information of the face region. Also, for example, the service server 1000 may extract information about at least one of an inflamed eye, a pupil size, movement of a pupil, a face size, a shape of a face contour, a cracked lip, a location of each organ of a face, or movement of facial muscles by using the face recognition algorithm or the facial expression recognition algorithm. Alternatively, any of various algorithms and methods may be used to extract the facial condition information.

Then, the service server 1000 extracts health status information by using the facial condition information in operation S4440. For example, the service server 1000 may extract the health status information by determining at least one of a skin condition, an eye status, a weight change, a lip status, a hair status, or a body condition.

Methods of extracting the facial condition information and the health status information may be updated by a user, e.g., a manager of the service server 1000 or a medical staff.

According to an exemplary embodiment, the service server 1000 may provide the facial condition information and/or the health status information extracted by a medical expert from the face image. In this case, the facial condition information and/or the health status information may be provided to the device 100 after some time or some days the face image is transmitted to the service server 1000.

After the health status information is obtained in operation S4440, the service server 1000 transmits the facial condition information and/or the health status information to the device 100 in operation S4450. The facial condition information and/or the health status information may be transmitted in operation S4450 via any of various methods, for example, via an application message, an SMS message, a message of a messenger application, or an email.

The device 100 provides the facial condition information and/or the health status information received from the service server 1000 to a user in operation S4460. For example, the device 100 may display the health status information on a screen of the device 100.

Figure 45:
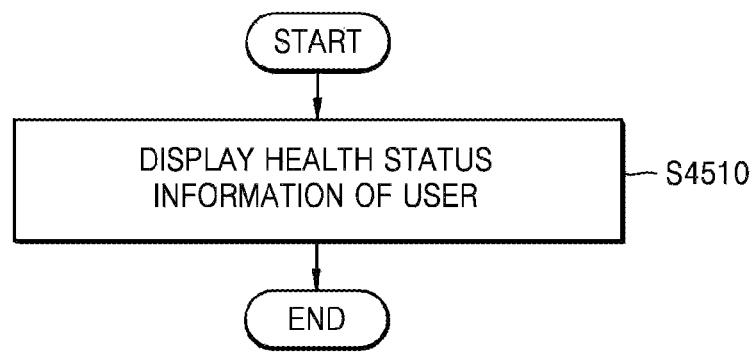
FIG. 45 is a flowchart of a method of displaying, by a device, health status information of a user, according to an exemplary embodiment.

FIG. 45 is a flowchart of a method of displaying, by the device 100, health status information of a user, according to an exemplary embodiment.

In operation S4510, the device 100 may display the health status information of the user.

The device 100 may display the health status information obtained by using facial condition information. Also, the device 100 may display not only the health status information, but also at least one of information about a symptom extracted from a face image, information about a cause of the symptom, information about another symptom that may be shown with the extracted symptom, or information about actions required to improve the symptom.

Figure 46:
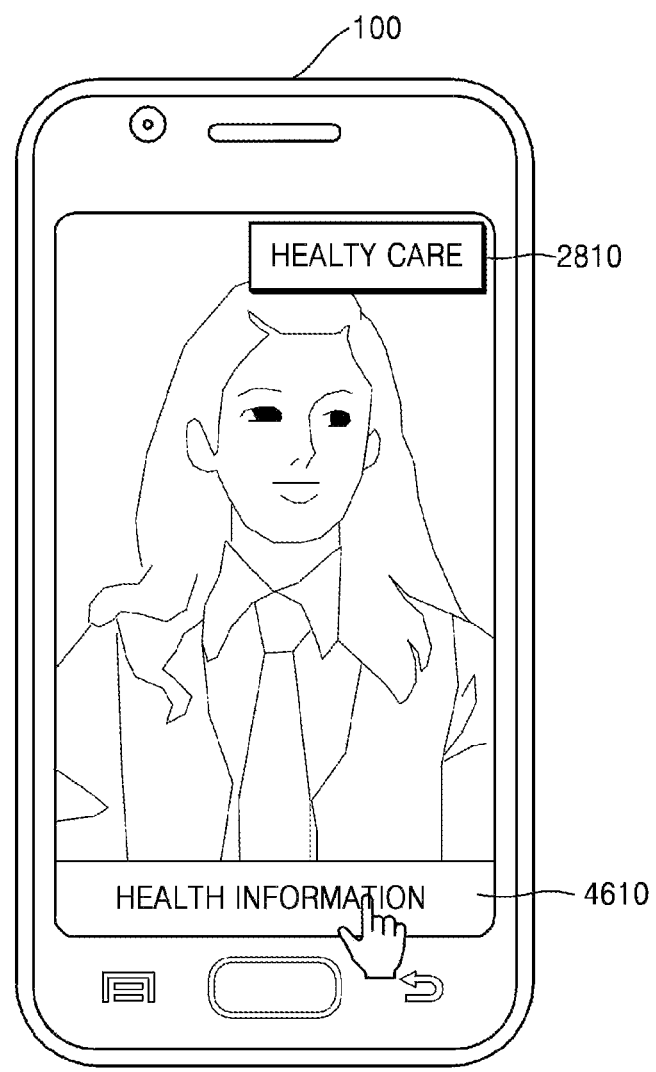
FIG. 46 is a diagram for describing a method of providing, by a device, a user interface for providing health status information calculated from a face of a user displayed by the device as the device displays a stored image, according to an exemplary embodiment.

FIG. 46 is a diagram for describing a method of providing, by the device 100, a user interface for providing health status information calculated from a face of a user displayed by the device 100 as the device 100 displays a stored image, according to an exemplary embodiment.

Referring to FIG. 46, the device 100 may display an image selected by the user from among images stored in the device 100.

Upon receiving a user input of selecting at least one of the stored images, the device 100 may determine whether the selected image is an image from which facial condition information is extracted. When the selected image is the image from which the facial condition information is extracted, the device 100 may display a user interface 4610 for providing health status information corresponding to a face image.

Upon receiving a user input of selecting the button 2810 of "HEALTH CARE" for providing the health status information, the device 100 may display the health status information stored correspondingly to the selected image.

Figure 47:
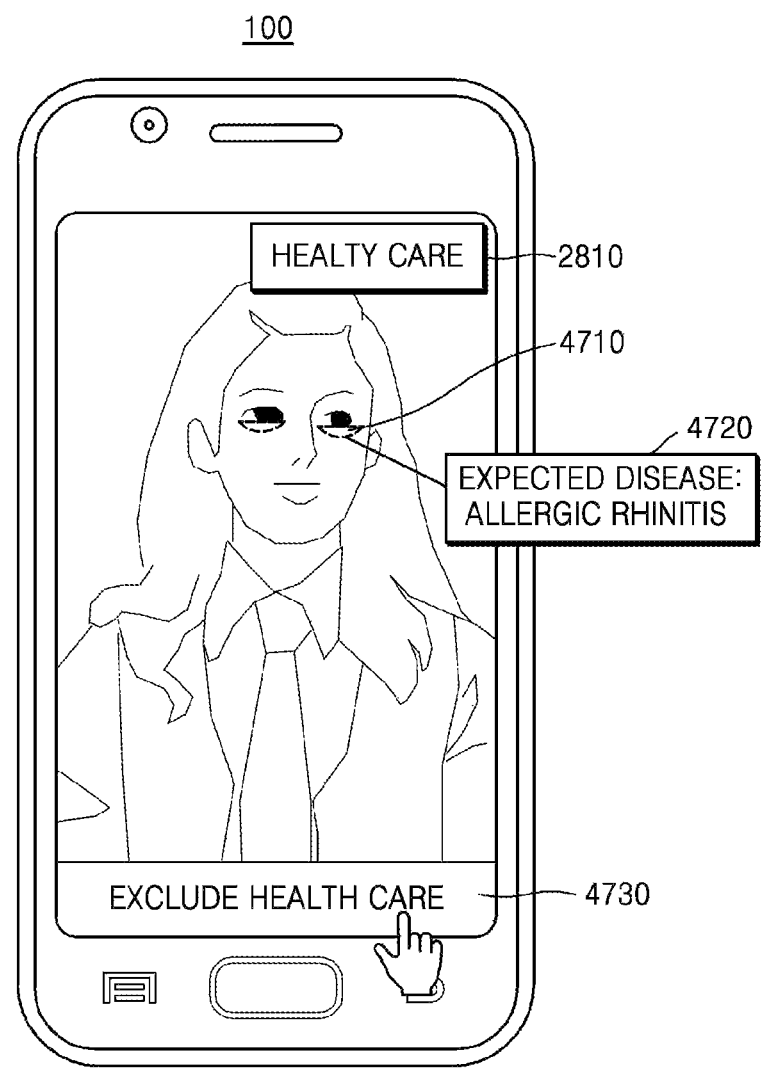
FIG. 47 is a diagram for describing a method of displaying, by a device, health status information on a displayed image, according to an exemplary embodiment.

FIG. 47 is a diagram for describing a method of displaying, by the device 100, health status information on a displayed image, according to an exemplary embodiment.

Referring to FIG. 47, the device 100 may display the health status information on the displayed image.

The device 100 may obtain ID information of the displayed image. The device 100 may obtain the health status information stored correspondingly to the obtained ID information. The device 100 may store a predicted disease according to the ID information and a location of a diagnosis region from which the predicted disease is extracted.

Accordingly, the device 100 may display a phrase 4720 indicating the predicted disease and an image 4710 indicating the diagnosis region from which the predicted disease is extracted, on the displayed image.

Also, the device 100 may provide a user interface 4730 for not extracting health status information from the displayed image. Upon receiving a user input of selecting the user interface 4730 for not extracting health status information from the displayed image, the device 100 may delete the health status information stored regarding the displayed image.

Accordingly, when health status information of a user is distorted since a face of the user is not clearly captured due to external environments, the distorted health status information may be deleted.

Figure 48A:
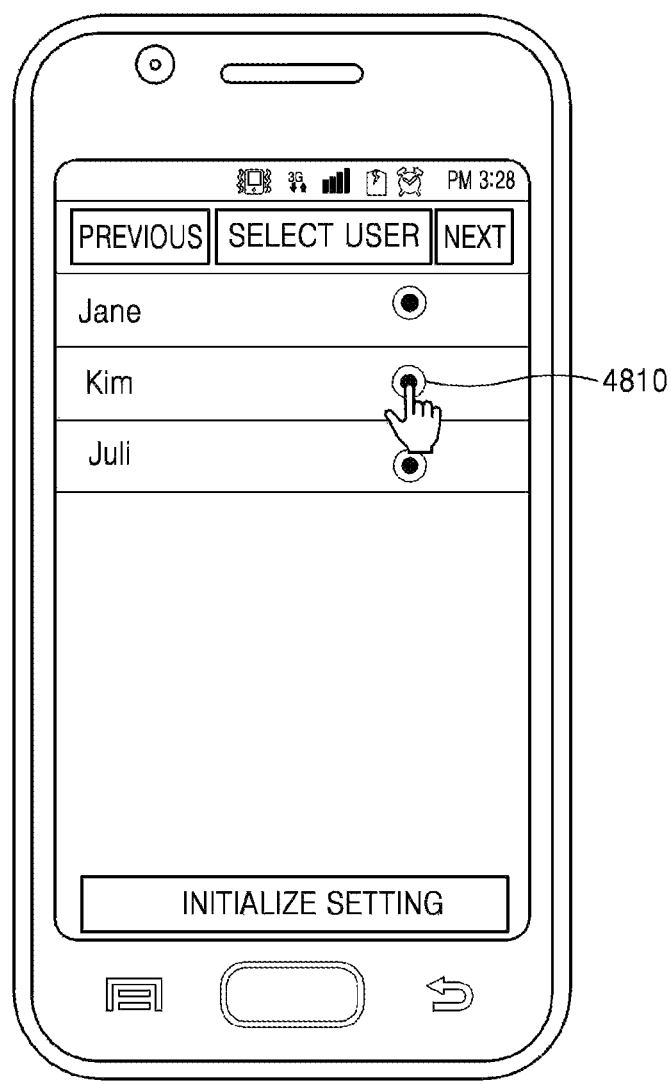
FIG. 48A is a diagram for describing a method of providing, by a device, a user interface for selecting a person to be displayed on a screen from health status information about a plurality of people, according to an exemplary embodiment.

FIG. 48A is a diagram for describing a method of providing, by the device 100, a user interface 4810 for selecting a person to be displayed on a screen from health status information about a plurality of people, according to an exemplary embodiment.

Referring to FIG. 48A, the device 100 may display the user interface 4810 for selecting a person to be displayed on the screen from the health status information of the plurality of people. The device 100 may extract, from the face image, the health status information of the plurality of people shown on a face image. Also, the device 100 may store ID information of an input image from which face condition information is extracted and health status information obtained from the facial condition information, correspondingly to ID information of a person. Upon receiving a user input of selecting one of the plurality of people, the device 100 may display an input image and health status information of the selected person.

Figure 48B:
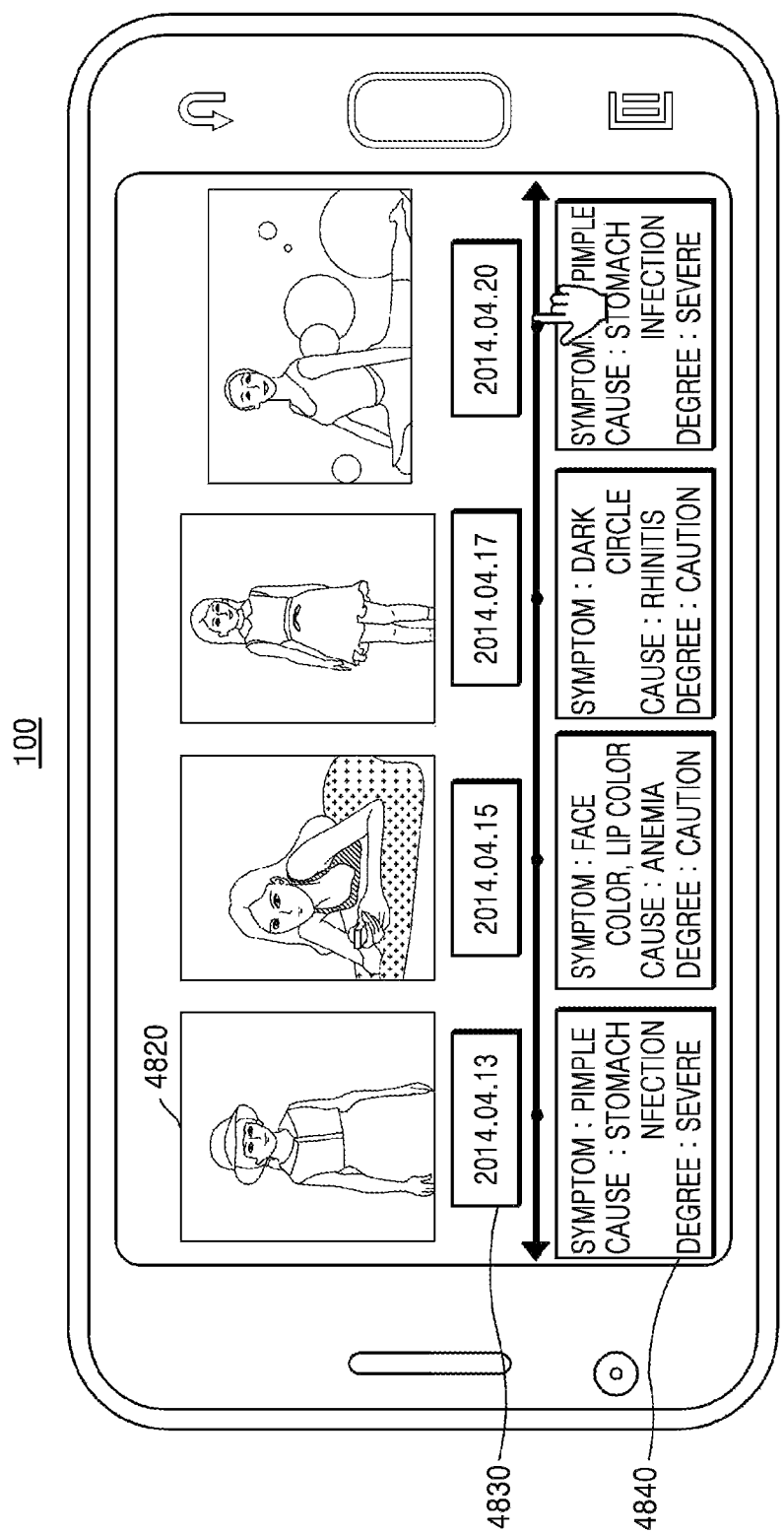
FIG. 48B is a diagram for describing a method of displaying, by a device, input images of a person selected by a user and health status information corresponding to the input images, according to an exemplary embodiment.

FIG. 48B is a diagram for describing a method of displaying, by the device 100, input images 4820 of a person selected by a user and health status information 4840 corresponding to the input images 4820, according to an exemplary embodiment.

Referring to FIG. 48B, the device 100 may display the input images 4820 of the person selected by the user, and the health status information 4840 corresponding to the input images 4820.

The device 100 may display the input images 4820 in a chronological order of photographed time of the input images 4820. Also, the device 100 may display date information 4830 when the input images 4820 are generated, together with the input images 4820. Also, the device 100 may display the health status information 4840 corresponding to the input images 4820.

Accordingly, the user may view the health status information 4940 according to a chronological order with respect to the selected person.

Figure 49A:
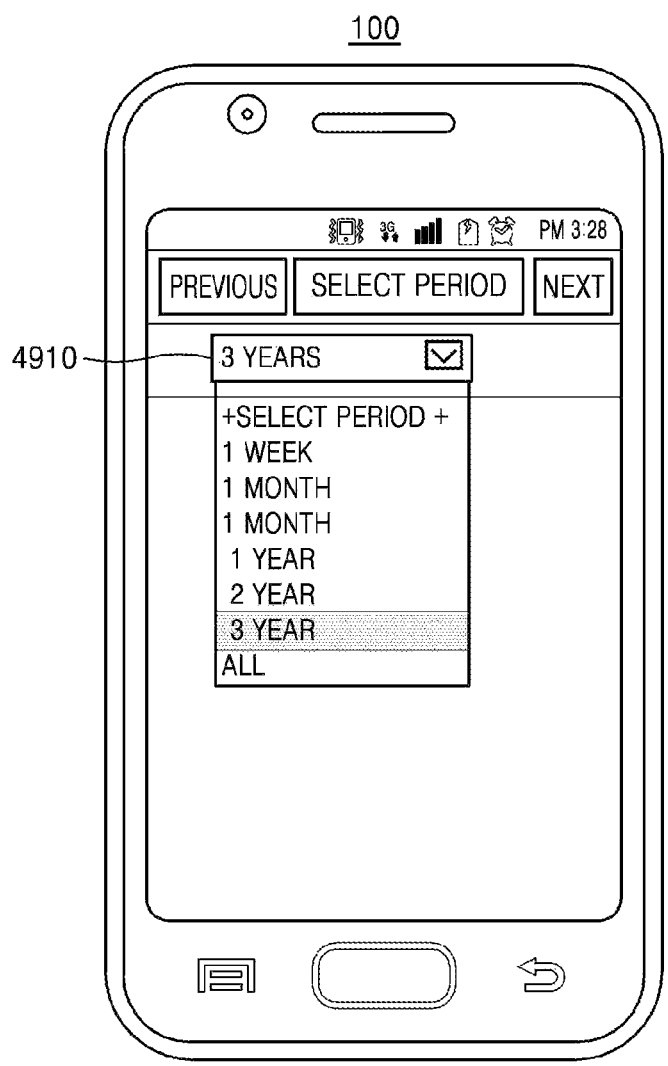
FIGS. 49A through 49C are diagrams for describing a method of providing, by a device, health status information about a period or a disease selected by a user, according to an exemplary embodiment.
Figure 49B:
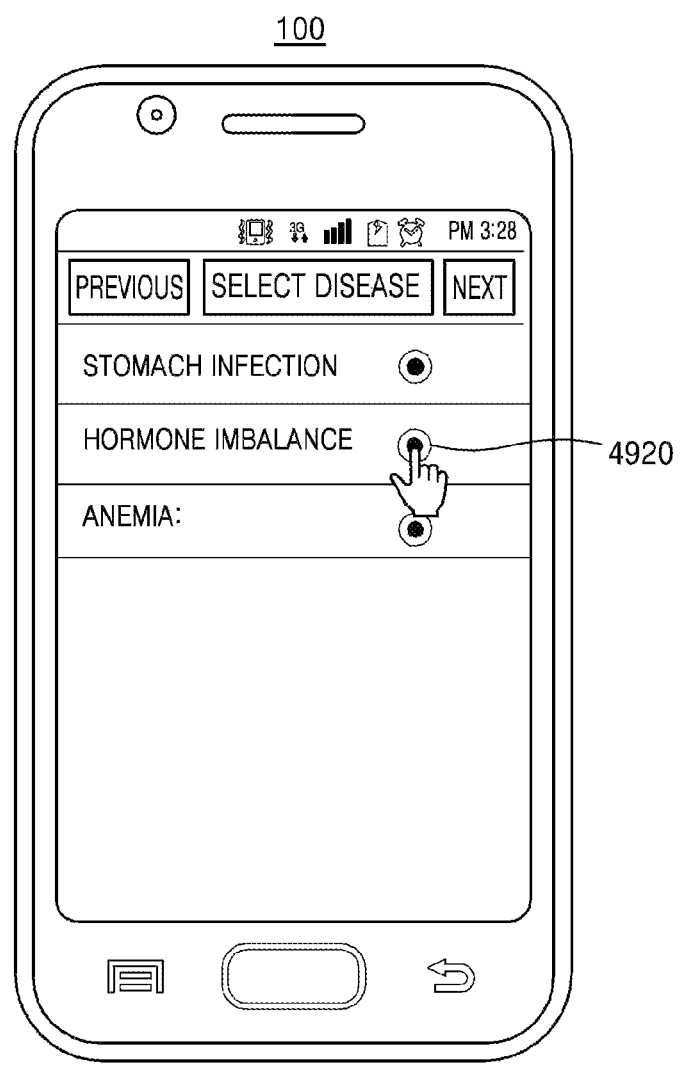
Figure 49C:
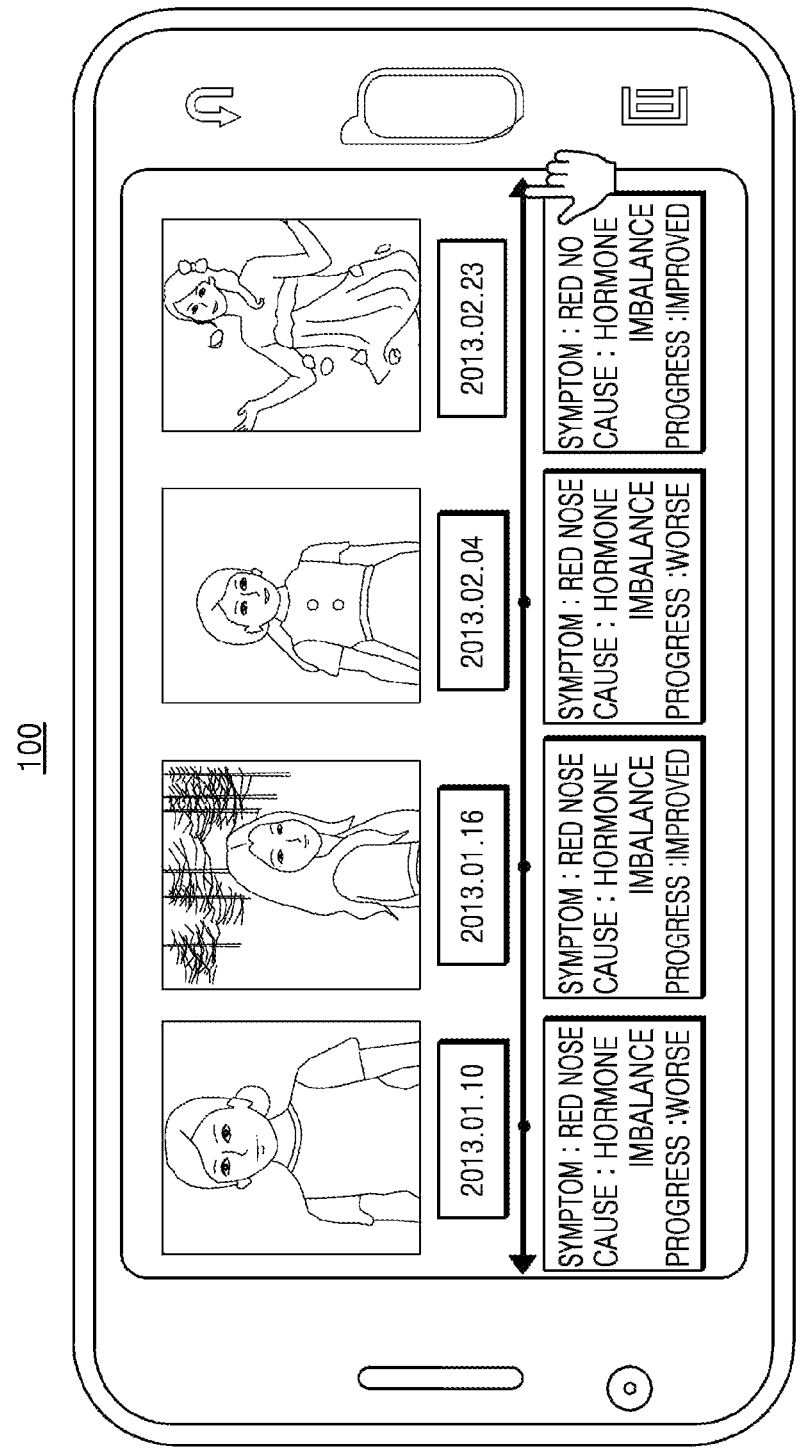

FIGS. 49A through 49C are diagrams for describing a method of providing, by the device 100, health status information about a period or a disease selected by a user, according to an exemplary embodiment.

Referring to FIG. 49A, the device 100 may display a user interface 4910 for selecting a period. The user interface 4910 may be a user interface for selecting a unit period from a current point of time to the past.

Upon receiving a user input of selecting a unit period from the current point of time to the past, the device 100 may display health status information extracted from images captured during the selected unit period.

Referring to FIG. 49B, the device 100 may display a user interface 4920 for selecting a disease. The device 100 may display a disease of the user related to images stored in the device 100. Also, the device 100 may display a disease of the user related to images captured during a unit period selected by the user from among the images stored in the device 100.

Referring to FIG. 49C, upon receiving user inputs of selecting a unit period and a disease, the device 100 may display input images related to the selected disease during the selected unit period in a chronological order.

Figure 50A:
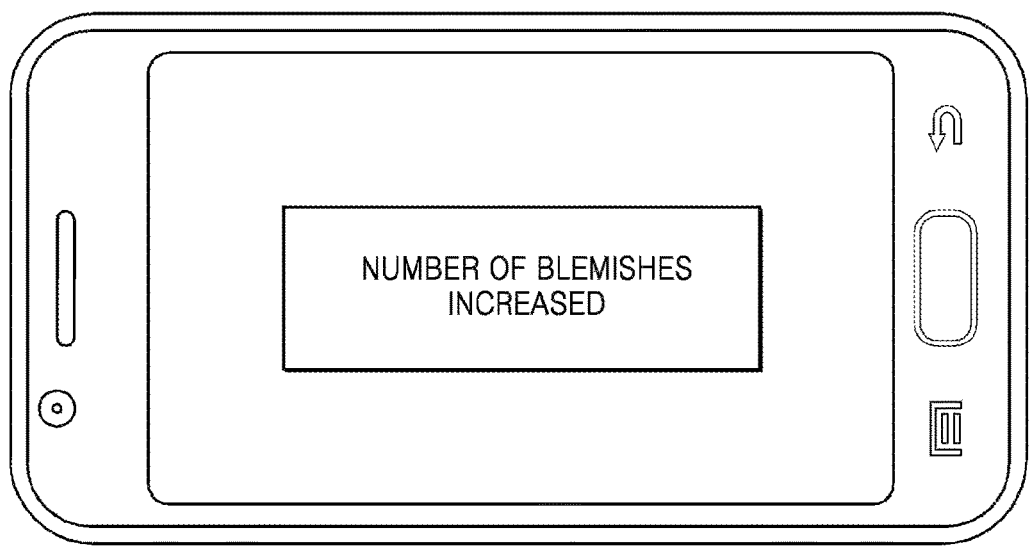
FIG. 50A illustrates a screen of providing health status information, according to an exemplary embodiment.

FIG. 50A illustrates a screen of providing health status information, according to an exemplary embodiment.

According to an exemplary embodiment, the health status information calculated (e.g., determined or obtained) by the device 100 may be displayed on the screen of the device 100. Also, when a health status changes, the device 100 may provide information about the change to a user. For example, as shown in FIG. 50A, a message indicating that a skin condition is worsened due to an increased number of blemishes may be displayed on the screen.

Figure 50B:
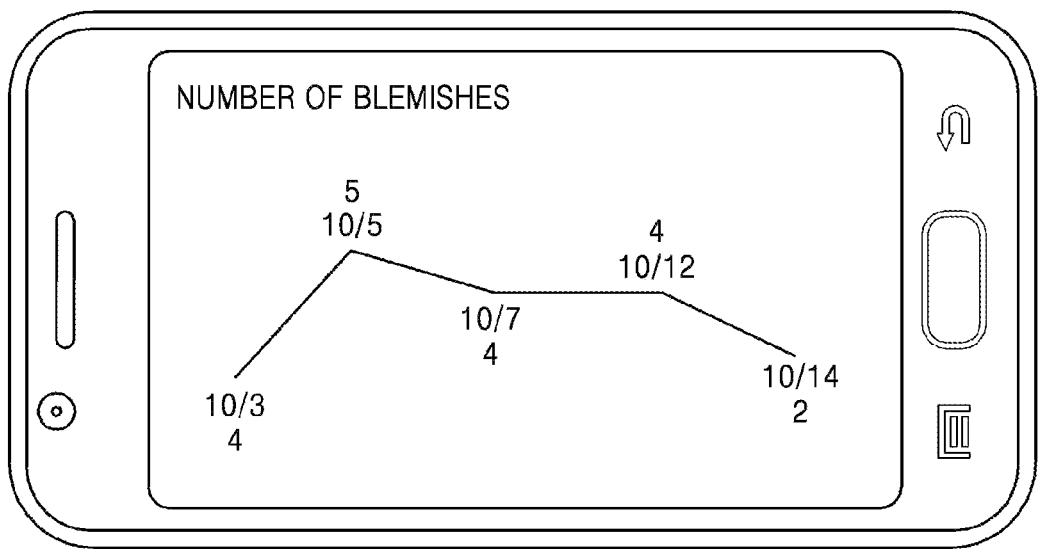
FIG. 50B illustrates a screen of providing health status information, according to another exemplary embodiment.

FIG. 50B illustrates a screen of providing health status information, according to another exemplary embodiment.

According to an exemplary embodiment, the health status information may be provided in a form of notifying a change of the health status information over time. When a face image is extracted by using a captured image, a time may be determined based on a captured time of the captured image or a current time. When a face image is extracted by using a stored image, time may be determined based on a photographed date stored in an image file of the stored image. For example, as shown in FIG. 50B, a change of a number of blemishes is shown according to dates to notify a user about skin condition according to time. Alternatively, the device 100 may provide a change of blood pressure, a skin color, an eye condition, or a skin condition according to time. According to the current exemplary embodiment, the user is able to easily recognize the change of the health status information according to time.

Figure 51A:
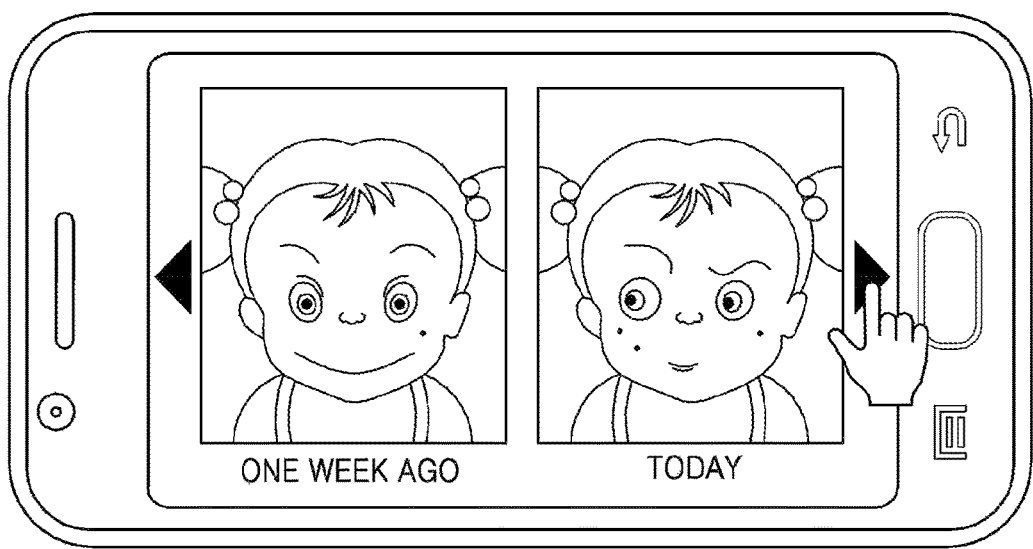
FIG. 51A illustrates a screen of providing health status information, according to another exemplary embodiment.

FIG. 51A illustrates a screen of providing health status information, according to another exemplary embodiment.

According to an exemplary embodiment, the device 100 may display the health status information together with a face image. For example, as shown in FIG. 51A, numbers of blemishes of one week ago and today may be shown by using face images. According to the current exemplary embodiment, a change of a health status may be shown intuitively and visually.

Also, according to the current exemplary embodiment, the device 100 may provide the face image and the health status information together by comparing a best status and a current status. For example, the device 100 may display a face image showing a best skin condition and a face image showing a current skin condition. According to the current exemplary embodiment, the user may intuitively determine the current status by comparing the best status and the current status.

Also, according to the current exemplary embodiment, the device 100 may provide the health status information by displaying the face image of the user showing the current status and a base face image showing a normal status. Here, the base face image may not be a face image of the user. According to the current exemplary embodiment, the user may intuitively determine his/her health status.

Figure 51B:
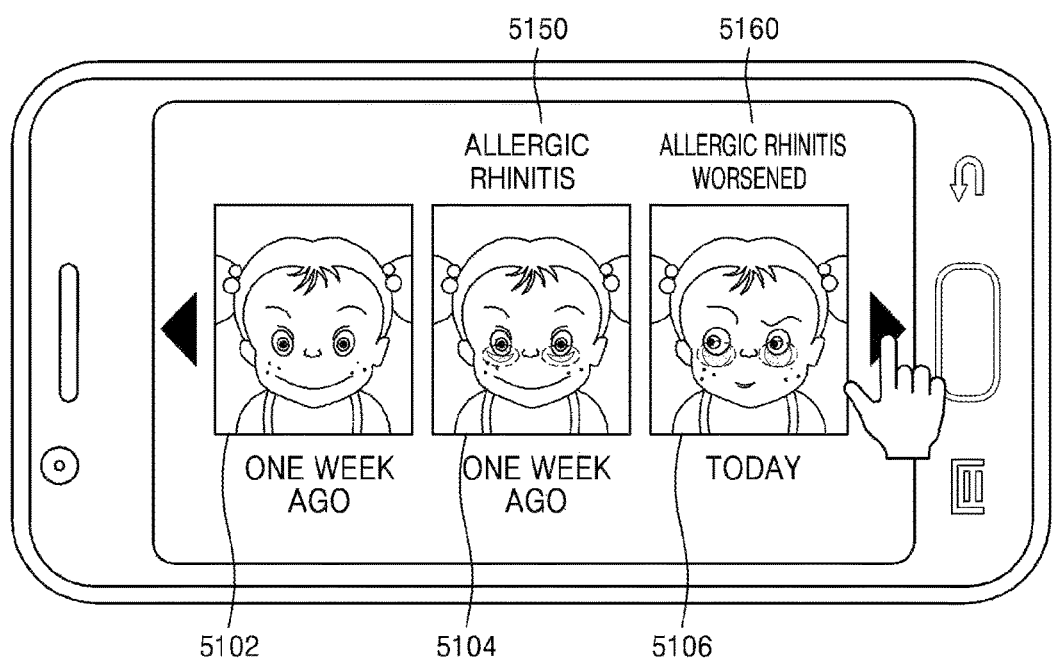
FIG. 51B is a diagram for describing a method of displaying, by a device, facial condition information that changes over time, from among pieces of facial condition information of a user, according to an exemplary embodiment.

FIG. 51B is a diagram for describing a method of displaying, by the device 100, facial condition information that changes over time, from among pieces of facial condition information of a user, according to an exemplary embodiment.

Referring to FIG. 51B, the device 100 may display the facial condition information that changes over time by comparing a photograph 5102 captured a first time period (e.g., one week) ago, a photograph 5104 captured a second time period (e.g., three days ago), and a current photograph 5106. Also, the device 100 may display, on a face region of an input image of the user, from which different facial condition information that is different from past facial condition information is extracted, an indicator indicating that the different facial condition information is extracted.

For example, the device 100 may extract information that a number of pimples on cheeks is equal to or higher than a threshold number from the photograph 5102, as facial condition information. Accordingly, the device 100 may obtain information that a function of lung is deteriorated from the photograph 5102, as health status information.

Upon obtaining the photograph 5104 as an input image, the device 100 may extract information that the number of pimples on cheeks is equal to or higher than the threshold number and dark circles are generated under eyes from the photograph 5104, as facial condition information. When a difference between the number of pimples in the photograph 5104 and the number of pimples in the photograph 5102 is within a threshold value, the device 100 may not separately display information about the pimples on the photograph 5104. Also, the device 100 may not determine that the pimples are worsened or improved.

Meanwhile, since the dark circles under the eyes detected from the photograph 5104 are not included in the facial condition information extracted from the photograph 5102, in order to indicate information about a facial condition of the user changed three days ago based on one week ago, the device 100 may display images 5110 and 5120 indicating such changes on regions of the dark circles.

Also, upon obtaining the current photograph 5106 as an input image, the device 100 may extract information that the number of pimples on cheeks is equal to or higher than the threshold number and the dark circles are generated under the eyes from the current photograph 5106, as facial condition information. When a difference between the number of pimples in the current photograph 5106 and the number of pimples in the photograph 5104 is within a threshold value, the device 100 may not separately display information about the pimples on the current photograph 5106. Also, the device 100 may not determine that the pimples are worsened or improved.

Meanwhile, since the dark circles under the eyes detected from the current photograph 5106 are determined to be larger and darker than those detected from the photograph 5104, in order to indicate information about a facial condition of the user currently changed based on three days ago, the device 100 may display images 5130 and 5140 indicating such changes on the regions of the dark circles.

As such, the device 100 may provide the information about the facial conditions that change over time.

Also, the device 100 may display health status information indicating a health status of the user, which is different at a point of time when a current input image is captured compared to a point of time when a past input image was captured, based on information indicating at least one difference between current facial condition information and past facial condition information of the user.

For example, based on the dark circles detected from the photograph 5104, the device 100 may display a phrase 5150 indicating allergic rhinitis, as health status information. Also, based on the darker and larger dark circles detected from the current photograph 5106, the device 100 may display a phrase 5160 indicating that the allergic rhinitis is worsened, as health status information.

As such, the device 100 may provide the health status information that changes over time.

Figure 52:
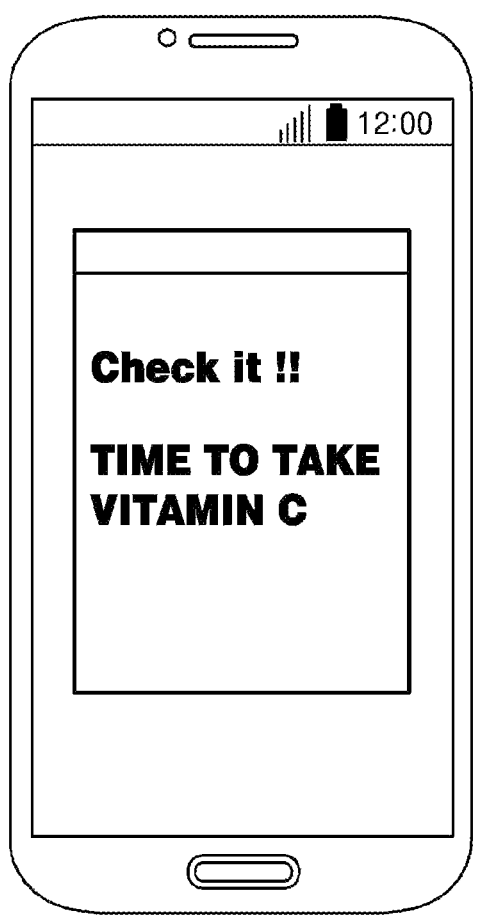
FIG. 52 illustrates a screen of providing health status information, according to another exemplary embodiment.

FIG. 52 illustrates a screen of providing health status information, according to another exemplary embodiment.

According to an exemplary embodiment, the device 100 may provide advice to a user based on the health status information. For example, when a skin condition of the user is bad, advice to take vitamin C may be provided. Here, in order to induce the user to take vitamin C twice a day, a notification to take vitamin C may be provided as a popup message at two certain points of time. Alternatively, for example, the device 100 may provide a message or notification inducing the user to exercise at a certain point of time.

Alternatively, the device 100 may provide information about a food, a lifestyle, or an exercise required by or suggested or determined for the user based on the health status information of the user.

Figure 53A:
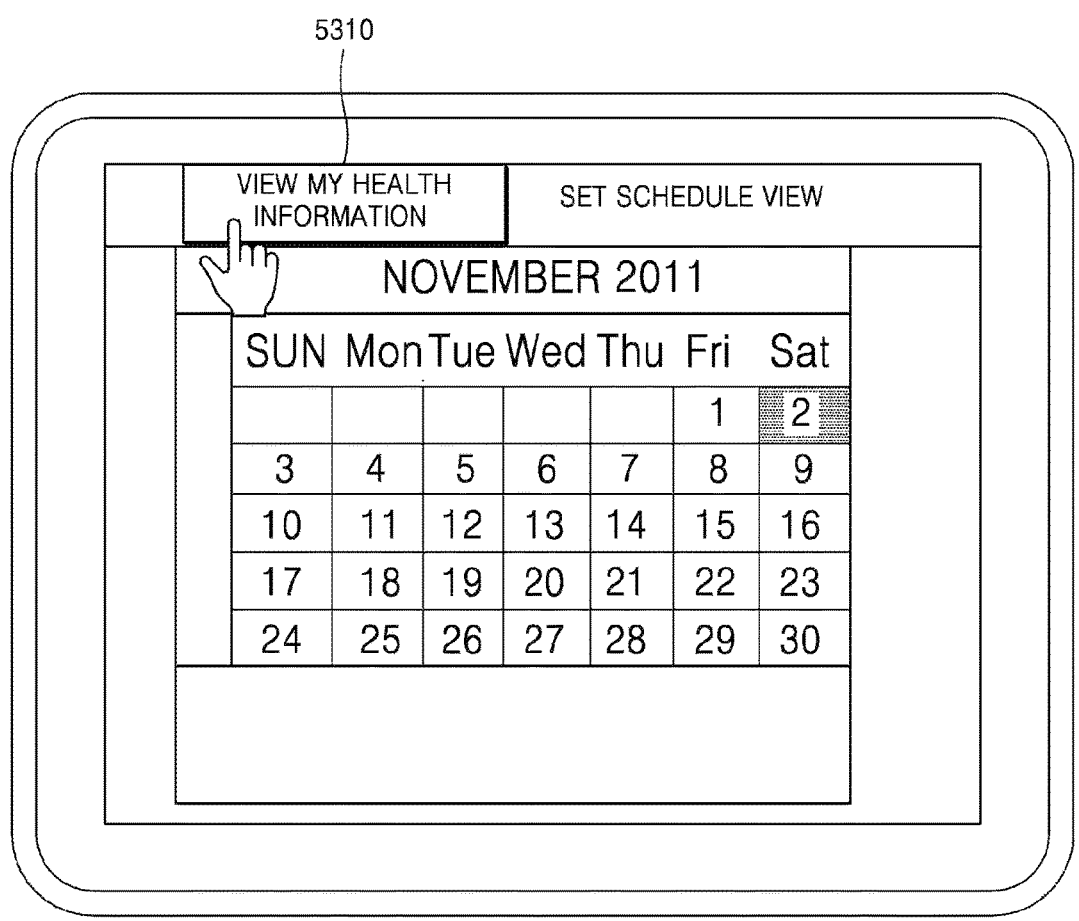
FIGS. 53A and 53B are diagrams for describing a method of providing, by a device, health status information of a user in a calendar form, according to an exemplary embodiment.
Figure 53B:
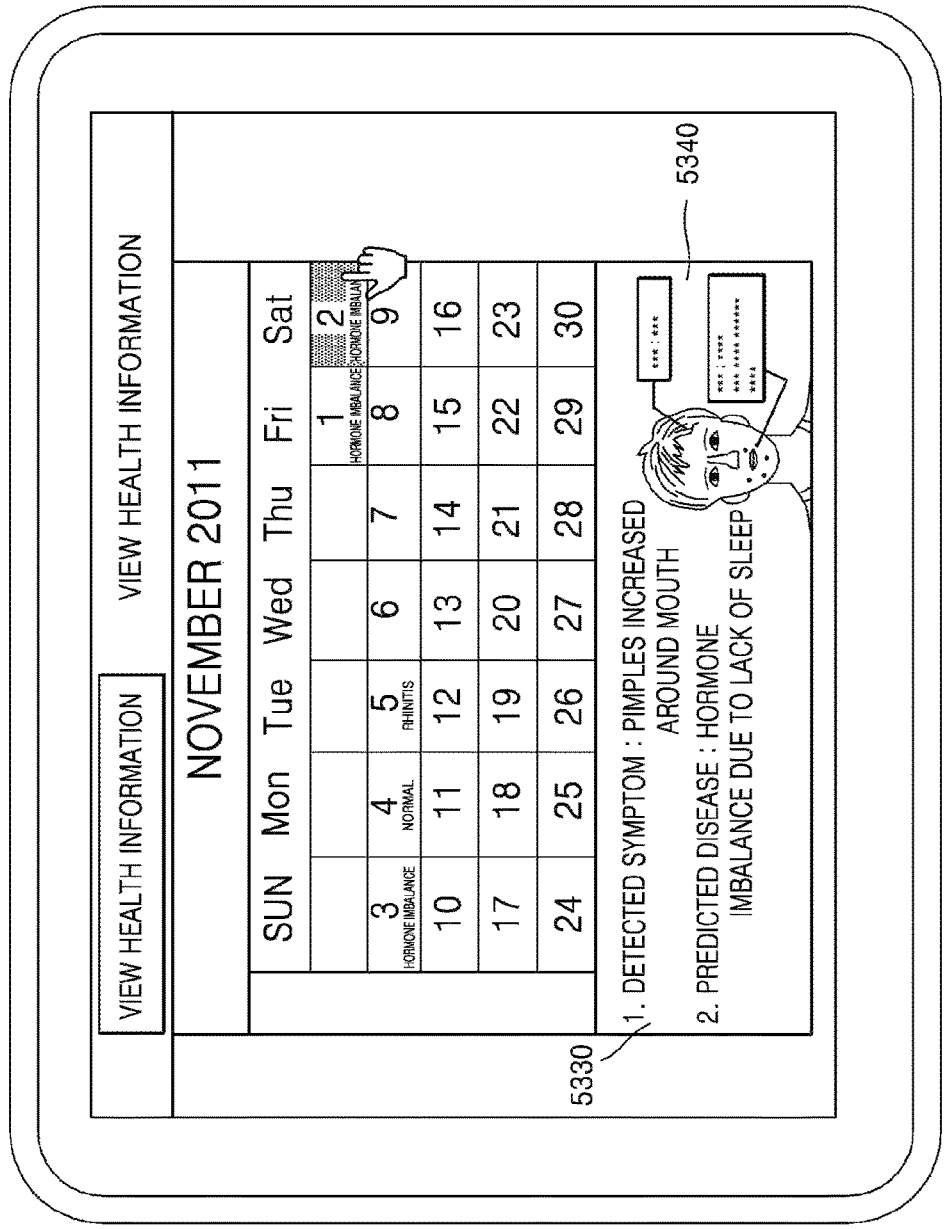

FIGS. 53A and 53B are diagrams for describing a method of providing, by the device 100, health status information of a user in a calendar form, according to an exemplary embodiment.

Referring to FIG. 53A, the device 100 may display a calendar showing dates per week or month on one screen. Also, the device 100 may display a user interface 5310 for displaying health status information corresponding to dates.

Referring to FIG. 53B, upon receiving a user input of selecting the user interface 5310 for displaying the health status information corresponding to dates, the device 100 may display health status information corresponding to a face image captured on each date, on a region corresponding to each date.

The device 100 may store the health status information corresponding to the face image captured on each date, and ID information of the face image. Here, the health status information corresponding to each date may be obtained from facial condition information extracted from the face image captured on each date.

Also, upon receiving a user input of selecting one date, the device 100 may display a face image 5340 captured on the selected date and health status information 5330 obtained from facial condition information extracted from the face image 5340.

Figure 54:
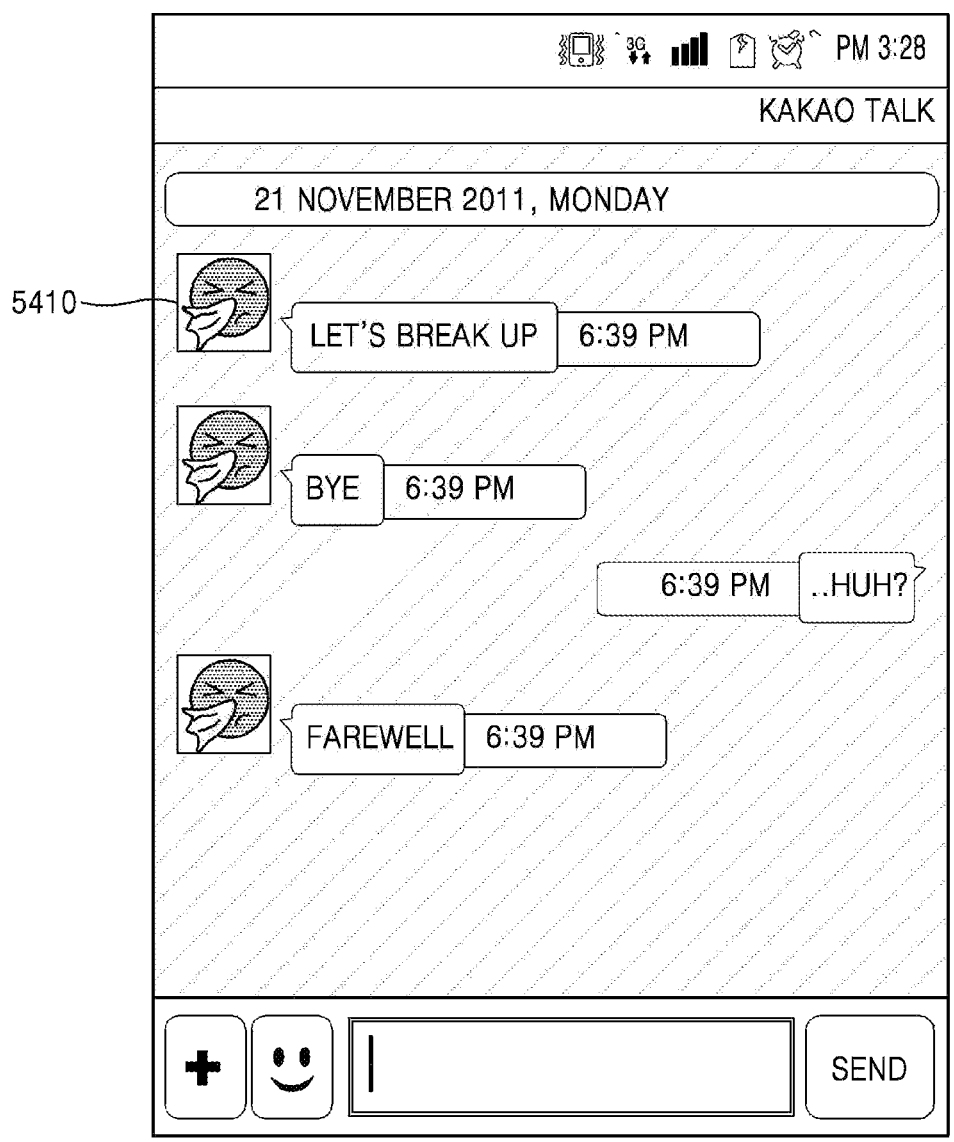
FIG. 54 is a diagram for describing a method of displaying, by a device, health status information of a user when a social network application is executed, according to an exemplary embodiment.

FIG. 54 is a diagram for describing a method of displaying, by the device 100, health status information of a user when a social network application is executed, according to an exemplary embodiment.

Referring to FIG. 54, the device 100 may display the health status information of the user when the social network application is executed.

For example, the device 100 may store health status information corresponding to a face image. The device 100 may store health status information corresponding to a face image that is recently captured as current health status information. In this case, the current health status information may be stored at a certain location. As such, the social network application executed in the device 100 may extract the health status information from the certain location.

Also, the social network application executed in the device 100 may display an image 5410 that shows a status of the user, based on the current health status information. For example, the social network application executed in the device 100 may display an image of a sick person when a health status of the user is equal to or lower than a reference value.

Figure 55:
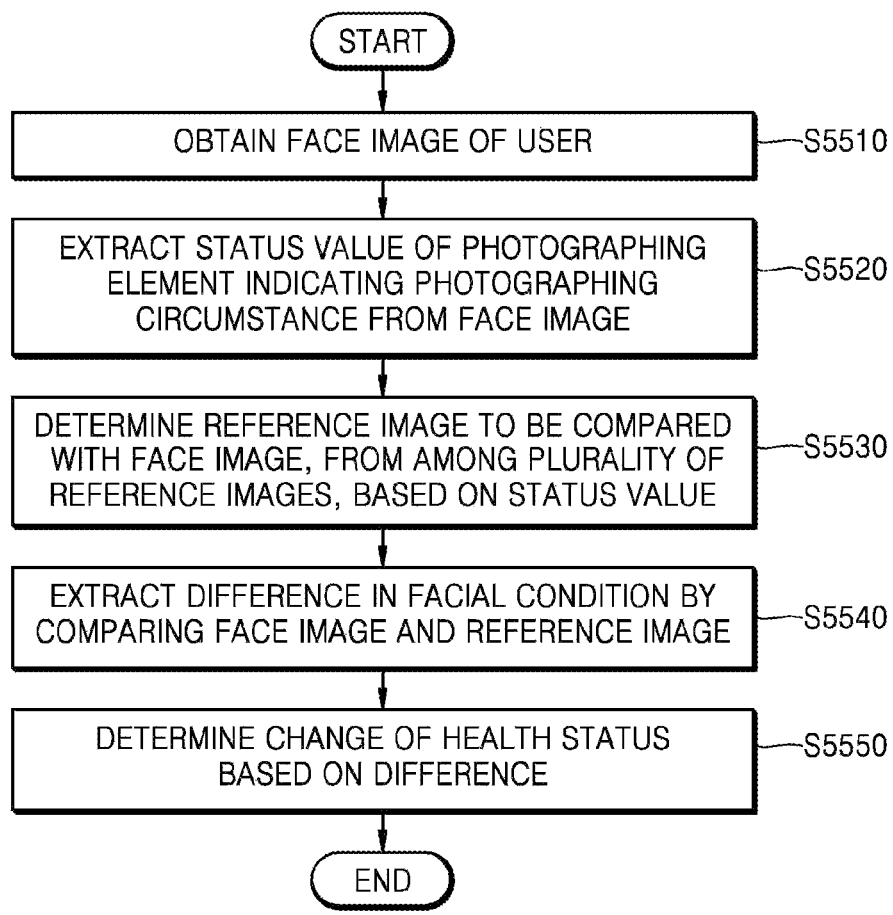
FIG. 55 is a flowchart illustrating a method of extracting, by a device, a difference in a facial condition of a user by comparing a face image and a reference image.

FIG. 55 is a flowchart illustrating a method of extracting, by the device 100, a difference in a facial condition of a user by comparing a face image and a reference image.

In operation S5510, the device 100 may obtain a face image of a user.

For example, the device 100 may receive an input image including a face of the user from an imaging unit (e.g., imager) included in the device 100. At this time, the device 100 may provide a template capturing interface for obtaining an input image satisfying a pre-set face image obtaining condition.

Also, when the input image satisfies the pre-set face image obtaining condition, the device 100 may capture the face of the user even if there is no user input.

Alternatively, the device 100 may obtain an image selected by the user from among images stored in the device 100, as the input image. Alternatively, the device 100 may obtain an image downloaded from an external device, as the input image.

The device 100 may extract a face region from the input image, and store the face region as the face image.

In operation S5520, the device 100 may extract a status value of a photographing element indicating a photographing circumstance from the face image.

The photographing element indicating the photographing circumstance may include at least one of lighting, a place, a background, a time zone, an angle of a face, or a facial expression, as shown in FIG. 56, but is not limited thereto in one or more other exemplary embodiments.

For example, the device 100 may extract brightness, a direction, and a color temperature of lighting during photographing, from the face image.

In operation S5530, the device 100 may determine a reference image to be compared with the face image, from among a plurality of reference images, based on the status value.

The device 100 may store the plurality of reference images correspondingly to ranges of the status value. For example, a reference image captured at a place where brightness of lighting is 60 lux may be stored as a reference image corresponding to 50 to 70 lux. Also, a reference image captured at a place where brightness of lighting is 80 lux may be stored as a reference image corresponding to 70 to 90 lux.

Accordingly, the device 100 may determine the reference image corresponding to the status value extracted from the face image. For example, when brightness of lighting extracted from the face image is 60 lux, the device 100 may determine a reference image corresponding to 50 to 70 lux from among a plurality of reference images as the reference image to be compared with the face image.

A reference image may not only be pre-determined correspondingly to a plurality of status values of one photographing element, but may also be pre-determined correspondingly to a combination of a plurality of photographing elements. For example, reference images may be pre-determined correspondingly to each of 18 combinations of conditions in which brightness of lighting are 50 to 70 lux, 70 to 90 lux, and 90 to 110 lux, conditions in which places are home, a school, and an office, and conditions in which directions of a face are left and right.

In operation S5540, the device 100 may extract the difference in the facial condition by comparing the face image and the reference image.

The device 100 may compare the face image and the reference image to extract the difference from the face image. For example, information about whether a number of pimples is increased in the face region, whether a face color is darkened, or whether lips are drier compared to the reference image may be extracted.

In operation S5550, the device 100 may determine a change of a health status of the user based on the difference.

For example, when the number of pimples is increased, the device 100 may determine that hormone secretion of the user is unstable. Also, when the face color is darkened, the device 100 may determine that blood circulation of the user is not smooth.

As such, the device 100 may compare the face image and the reference image reflecting the photographing circumstance of the face image to accurately determine the health status of the user.

FIG. 56 is a table of photographing elements according to an exemplary embodiment.

Referring to FIG. 56, the device 100 may determine not only a user, but also elements other than the user, as photographing elements.

The photographing elements may be elements that affect facial condition information extracted from a face image of the user.

The photographing elements may include at least one of brightness of lighting, a direction of lighting, and a color temperature of lighting. Darkness of a face color of the user may vary based on the brightness of the lighting. Also, shading in a face region of the user may vary based on the direction of the lighting. Also, the face color of the user may vary based on the color temperature of the lighting.

Also, the photographing elements may include at least one of a place and information about whether the user is indoors or outdoors. The place may not only include information about an absolute location, such as longitude and latitude, but also include information about a relative location, such as home, an office, or a school. A color temperature of the face image may vary based on whether the user is indoors or outdoors. Also, a makeup degree of the user may vary based on whether the user is at home, in an office, or in a school. Also, activities of the user at home, in an office, or in a school may differ based on a life pattern of the user.

Furthermore, the photographing elements may include a background color around a face of the user in the face image or an object around the face of the user in the face image. The device 100 may determine whether it is day or night based on whether the background color around the face is dark. Also, when a color around the face is a skin color, accuracy of a location of the face region may be affected.

Also, the photographing elements may include a time zone. A condition of the user may show a uniform pattern based on time zones, and a facial condition of the user may vary according to the condition. A pattern of the condition may be determined based on a day or a month. Alternatively, the condition may show a uniform pattern based on a day of the week.

Also, a makeup degree of the user may show a uniform pattern based on time zones. For example, the user may not be wearing makeup from 00:00 to 07:00, and may be wearing makeup from 10:00 to 17:00.

Also, the photographing elements may include an angle of the face of the user with respect to a camera during photographing. A region of the face exposed in the face image may differ based on the angle of the face. Furthermore, the photographing elements may include a facial expression of the user during photographing. A region of the face from which facial condition information is extracted may differ based on the facial expression.

FIG. 57 is a diagram for describing a method of determining, by the device 100, a reference image, according to an exemplary embodiment.

As shown in FIG. 57, the device 100 may provide a user interface for selecting an image to be used as a reference image from among a plurality of images stored in the device 100.

For example, when a button for selecting a reference image is selected, the device 100 may display images 5710 through 5740 including a face of a user from among the plurality of images stored in the device 100. Also, the device 100 may display a toggle button for selecting an image on each of the images 5710 through 5740.

Upon receiving a user input of selecting an image, the device 100 may store the selected image as a reference image.

Then, the device 100 may extract a status value of a photographing element indicating a photographing circumstance of the reference image from the reference image. For example, the device 100 may extract at least one of a time, a place, and a direction, an angle, and a color temperature of lighting from the reference image from metadata of in a reference image file. Also, the device 100 may analyze the reference image to obtain at least one of an angle, a direction, and a facial expression of the face of the user in a face image.

Furthermore, the device 100 may automatically determine the reference image. For example, the device 100 may determine a pre-registered image including the face of the user from among the plurality of images stored in the device 100, as the reference image. The device 100 may determine, as the reference image, an image in which resolution (for example, a number of pixels indicating the face of the user) of the face of the user is equal to or higher than a reference value.

Figure 58B:
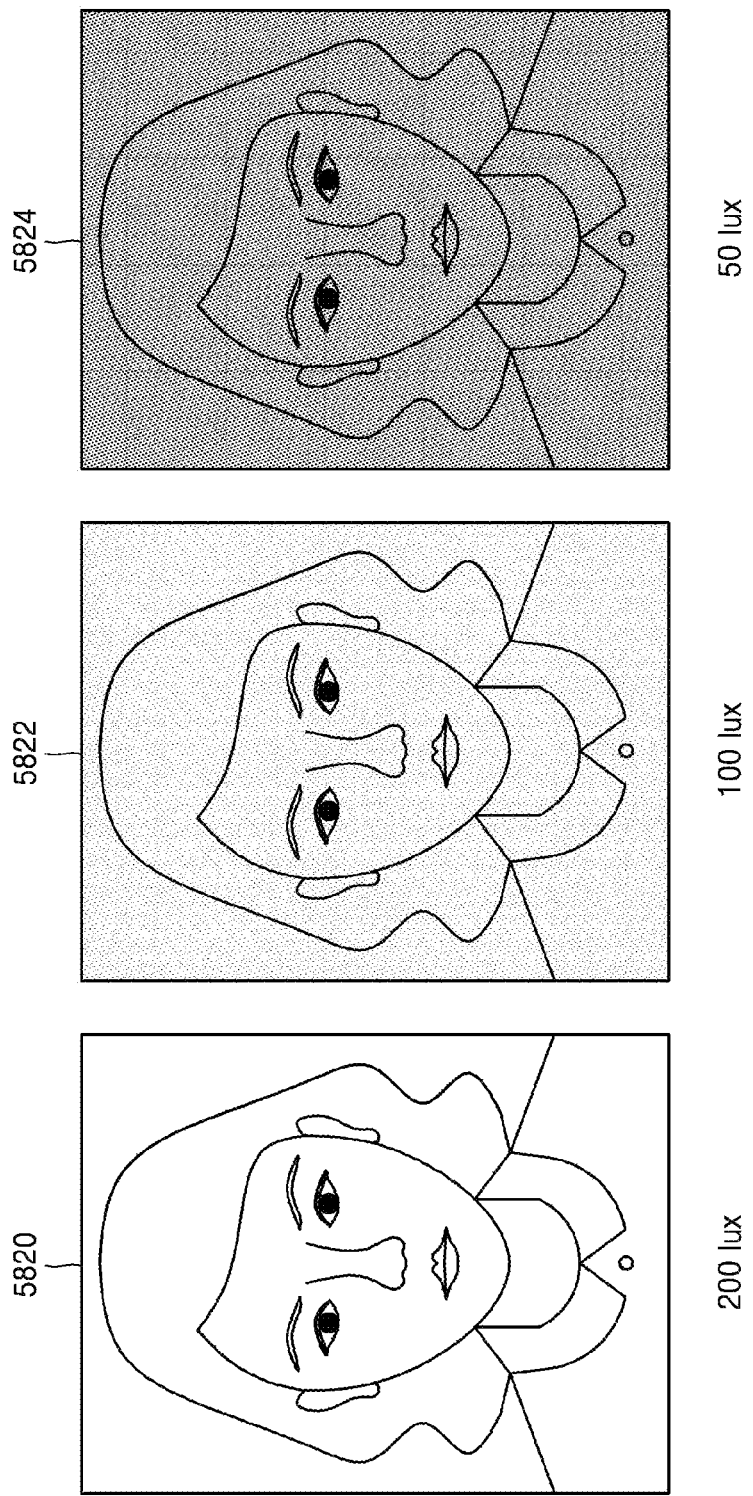

FIGS. 58A through 58C are diagrams for describing a method of determining, by the device 100, a reference image, according to one or more exemplary embodiments.

Referring to FIG. 58A, the device 100 may determine a reference image according to a place, from among a plurality of images.

For example, the device 100 may determine a reference image according to longitude and latitude, based on longitude and latitude stored as metadata in an image file. Alternatively, the image file may store a relative location, such as home or an office, instead of an absolute location. Accordingly, the device 100 may determine a reference image 5810 corresponding to home and a reference image 5815 corresponding to an office.

Referring to FIG. 58B, the device 100 may determine a reference image according to brightness of lighting, from among a plurality of images.

For example, the device 100 may determine a reference image according to brightness of lighting, based on brightness of lighting stored as metadata in an image file. For example, a reference image 5820 when brightness of lighting during photographing is 200 lux, a reference image 5822 when brightness of lighting during photographing is 100 lux, and a reference image 5824 when brightness of lighting during photographing is 50 lux may be determined.

Referring to FIG. 58C, the device 100 may determine a reference image according to a location of lighting, from among a plurality of images.

The device 100 may determine a location of lighting by analyzing an image. For example, when a right side of a face of a user in an image is darker than a left side by at least a threshold value, it may be determined that lighting during photographing is located at the left. Also, when brightness is even throughout a face region, it may be determined that lighting is in the same direction as a camera. Furthermore, when a top portion of a face of a user in a face image is darker than a bottom portion by at least a threshold value, it may be determined that lighting is directly below the face of the user during photographing.

Accordingly, the device 100 may determine a reference image 5830 when a location of lighting during photographing is at left of a user, a reference image 5832 when a location of lighting during photographing is at right of a user, a reference image 5834 when a location of lighting during photographing is above a camera lens, and a reference image 5836 when a location of lighting during photographing is directly below a face of a user may be determined.

Figure 59:
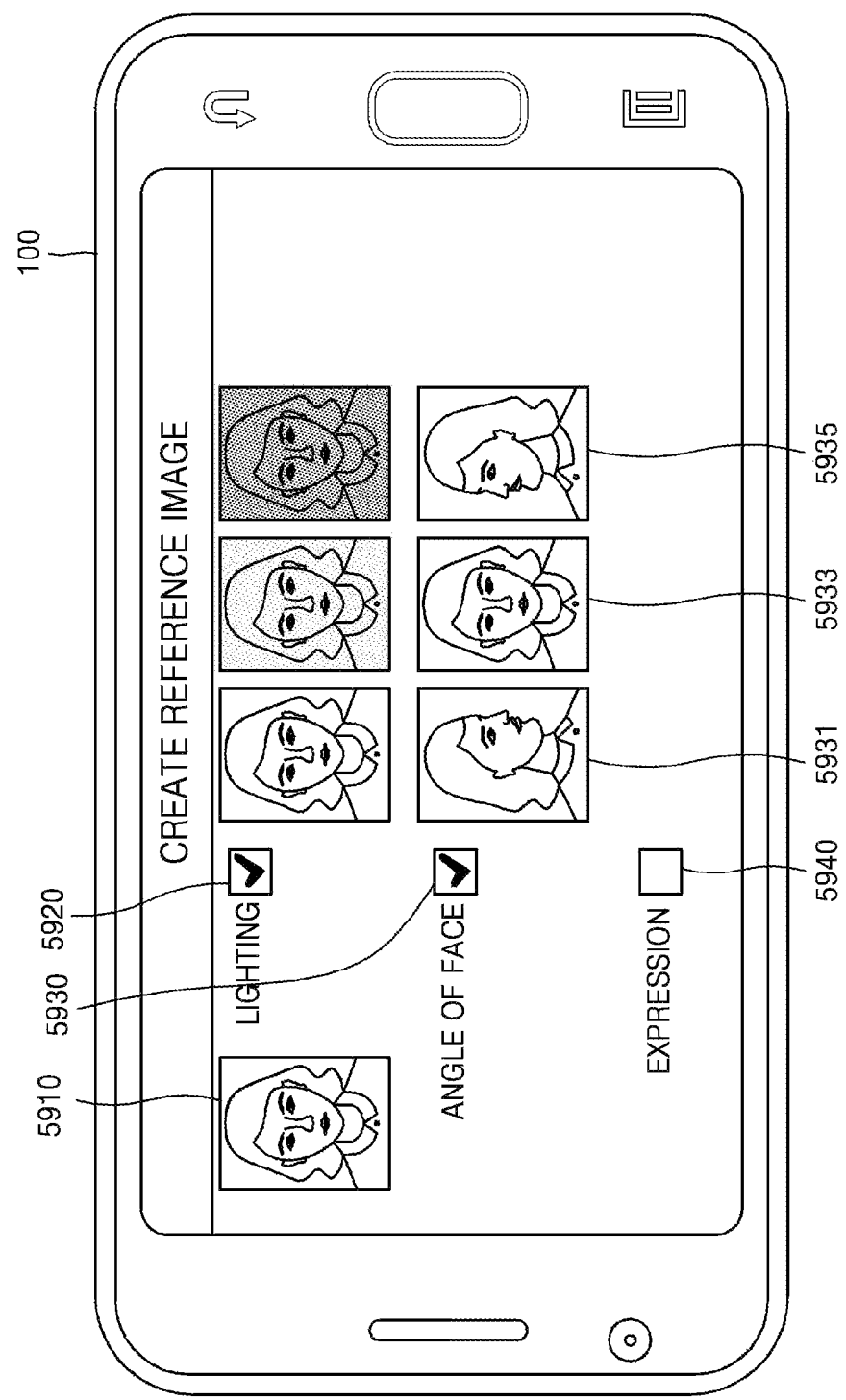
FIG. 59 is a diagram for describing a method of generating, by a device, a plurality of reference images according to circumstances by compensating one base image, according to an exemplary embodiment.

FIG. 59 is a diagram for describing a method of generating, by the device 100, a plurality of reference images 5921, 5923, 5925, 5931, 5933, and 5935 according to circumstances by compensating one base image 5910, according to an exemplary embodiment.

The reference image 5910 may be selected by a user, or the device 100 may automatically select an image that is closest to a face image obtaining condition, as the reference image 5910.

The device 100 may display a plurality of photographing elements, and may display toggle buttons 5920, 5930, and 5940 for selecting whether to generate a reference image according to the photographing elements.

Upon receiving a user input of selecting the toggle button 5920 for generating a reference image according to brightness of lighting, the device 100 may generate reference images in different brightness by compensating the base image 5910. For example, the device 100 may generate the reference images 5921, 5923, and 5925 respectively corresponding to 200 lux, 100 lux, and 50 lux by adjusting luminance of pixels in the base image 5910.

Also, upon receiving a user input of selecting the toggle button 5930 for generating a reference image according to an angle of a face, the device 100 may generate reference images in different angles by compensating the base image 5910. For example, the device 100 may generate the reference images 5931, 5933, and 5935 in which the face is respectively yawed to left, front, and right. Also, the device 100 may generate a reference image in which the face is pitched up or down. Also, the device 100 may generate a reference image in which the face is rolled left or right. As such, the device 100 may generate reference images according to various angles of the face.

Figure 60A:
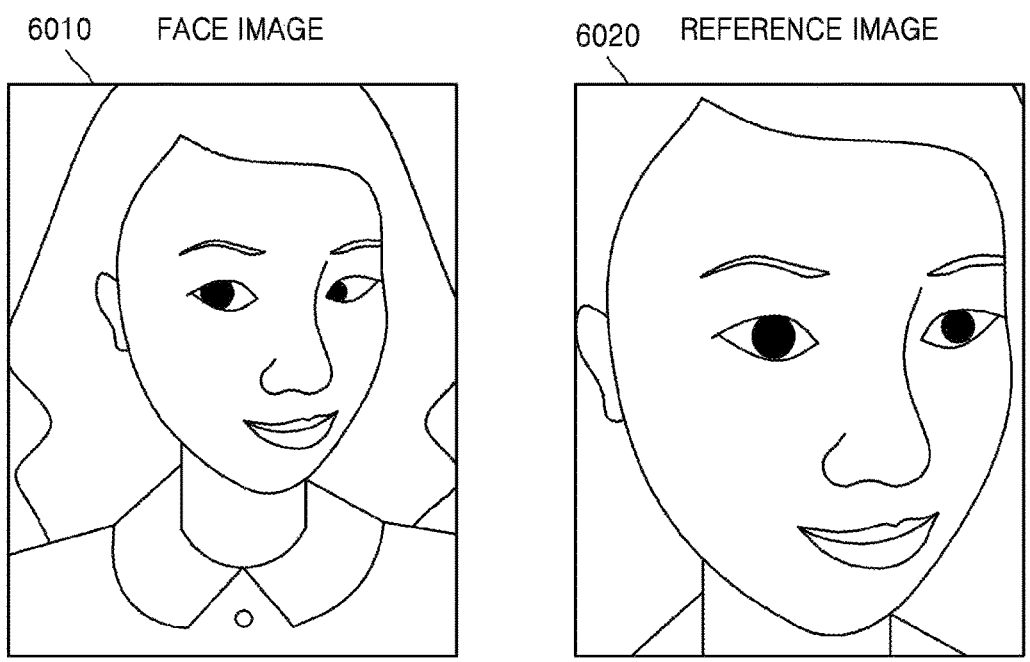
FIGS. 60A through 60B are diagrams for describing a method of determining, by a device, a reference image based on a status value of a photographing element of a face image, and determining, by the device, a health status of a user by comparing the face image and the reference image, according to an exemplary embodiment.
Figure 60B:
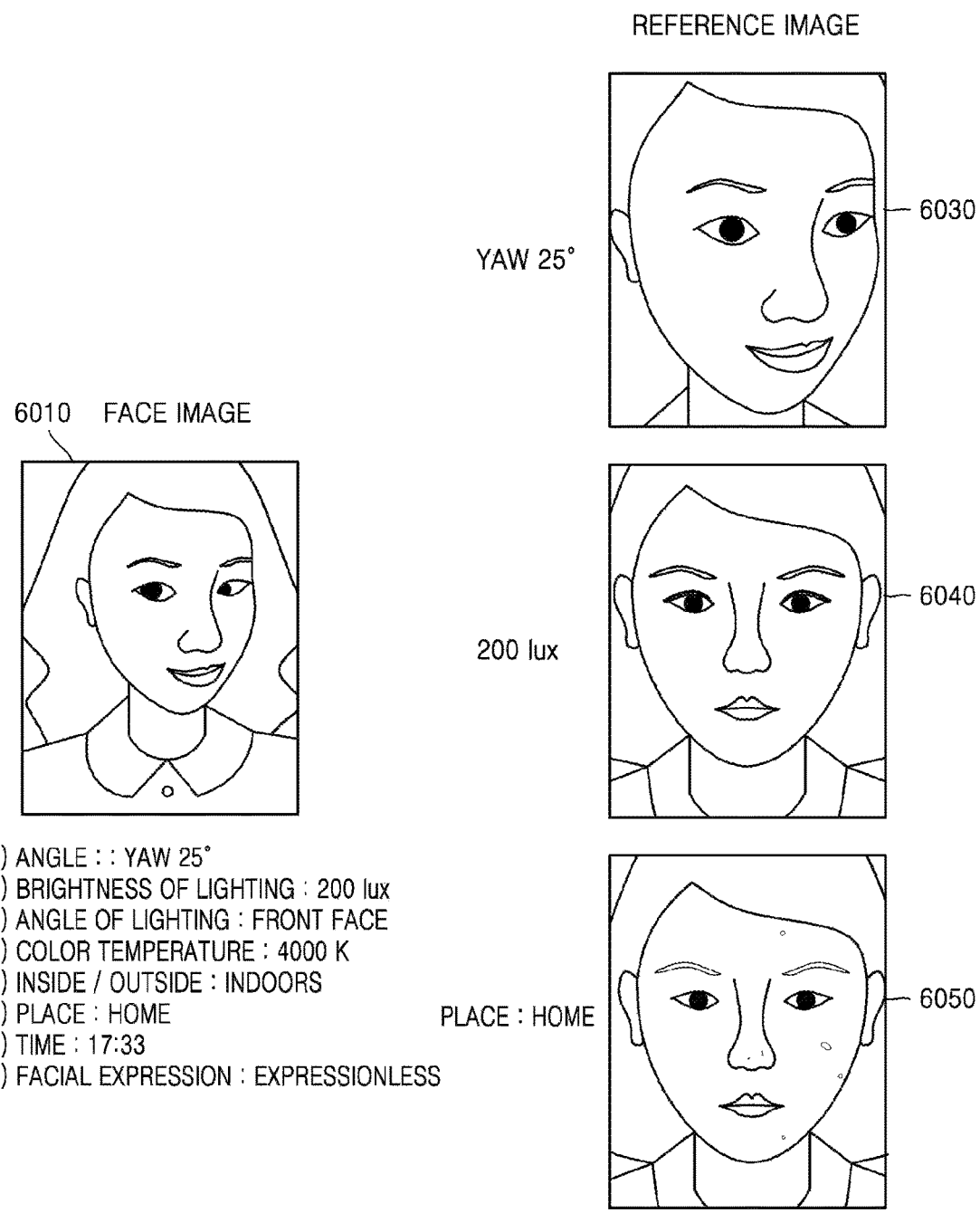

FIGS. 60A through 60B are diagrams for describing a method of determining, by the device 100, a reference image based on a status value of a photographing element of a face image, and determining, by the device 100, a health status of a user by comparing the face image and the reference image, according to an exemplary embodiment.

Referring to FIG. 60A, the device 100 may determine a state value of a photographing element of a face image 6010.

For example, the device 100 may calculate an angle of a face of a user in the face image 6010 to be yaw 25° by analyzing the face image 6010. Also, the device 100 may determine brightness of lighting during photographing to be 200 lux based on metadata in a file of the face image 6010. Furthermore, the device 100 may determine a photographed place to be home based on photographing location information in the file of the face image 6010. Also, the device 100 may determine that lighting is lighting the user straight by analyzing the face image 6010. Moreover, the device 100 may determine that a color temperature of the lighting is 4000 K by analyzing the face image 6010. Also, the device 100 may determine that the lighting is a fluorescent light based on the determined color temperature, and determine that the photographed place is indoors. Furthermore, the device 100 may determine that a photographed time is 17:33, and a facial expression of the user in the face image 6010 is expressionless.

Upon determining the status value of the photographing element of the face image 6010, the device 100 may determine one reference image based on the determined status value.

For example, the device 100 may obtain one reference image reflecting the determined status value. For example, the device 100 may obtain a reference image in which an angle of a face is yaw 25°, brightness of lighting is 200 lux, an angle of the lighting is a front face, a color temperature of the lighting is 4000 K, a photographed place is home, a photographed time is 17:33, and a facial expression is expressionless. At this time, the reference image may be a representative image in which an angle of a face is 15° to 30°, brightness of lighting is 150 to 200 lux, an angle of the lighting is a front face, a color temperature of the lighting is 3500 to 4500 K, a photographed place is home, a photographed time is 16:00 to 18:00, and a facial expression is expressionless.

According to an exemplary embodiment, the device 100 may determine a reference image based only on a photographing element having a status value outside a base range, from among a plurality of photographing elements. For example, when an angle of a face is equal to or higher than a base value, i.e., equal to or higher than 20° based on a front face, the device 100 may determine the angle of the face as a photographing element for determining a reference image. Alternatively, the device 100 may determine brightness of lighting as a photographing element for determining a reference image when the brightness is equal to or higher than 150 lux or 50 lux. Alternatively, the device 100 may determine a color temperature of lighting as a photographing element for determining a reference image when the color temperature is lower than or equal to 3000 K or is equal to or higher than 8000 K. Alternatively, the device 100 may determine a photographed time as a photographing element for determining a reference image when the photographed time is before 06:00 or after 23:00. Alternatively, the device 100 may determine a facial expression as a photographing element for determining a reference image when the facial expression is a smiling face or a frowning face.

As such, regarding the face image 6010 of FIG. 60A, the device 100 may select an angle of a face or brightness of lighting as a photographing element for determining a reference image. Also, the device 100 may determine a reference image 6020, in which an angle of a face is yaw 25° and brightness of lighting is 200 lux, from among a plurality of reference images, as a reference image to be compared with the face image 6010.

Alternatively, according to an exemplary embodiment, the device 100 may not only determine, as a reference image, an image that is pre-stored according to the status value of the photographing element of the face image 6010, but may also generate or obtain a reference image by compensating the face image 6010.

For example, the device 100 may obtain an image in which an angle of a face is yaw 25°, and generate a reference image to be compared with the face image 6010 by adjusting brightness of the obtained image to 200 lux.

Upon obtaining or generating the reference image 6020, the device 100 may compare the face image 6010 with the reference image 6020 to determine different facial condition information, and determine current health status information based on the different facial condition information.

Referring to FIG. 60B, the device 100 may determine a plurality of reference images based on the status values of the photographing elements of the face image 6010.

For example, the device 100 may obtain a reference image 6030 in which an angle of a face is yaw 25°, a reference image 6040 in which brightness of lighting is 200 lux, a reference image in which an angle of lighting is a front face, and a reference image in which a color temperature of lighting is 4000 K. Also, the device 100 may obtain a reference image 6050 in which a photographed place is home, a reference image in which a photographed time is about 17:00, and a reference image in which a facial expression is expressionless.

Upon determining the plurality of reference images corresponding to the photographing elements of the face image 6010, the device 100 may compare the face image 6010 with each of the plurality of reference images to determine a plurality of pieces of facial condition information corresponding to each of the plurality of reference images. Also, the device 100 may determine one piece of facial condition information by averaging or weight-averaging the plurality of pieces of facial condition information.

According to an exemplary embodiment, the device 100 may determine a reference image based only on a photographing element having a status value outside a base range, from among a plurality of photographing elements.

For example, the device 100 may determine three pieces of facial condition information by comparing the face image 6010 with each of the reference image 6030 in which an angle of a face is yaw 25°, the reference image 6040 in which brightness of lighting is 200 lux, and the reference image 6050 in which a photographed place is home, and determine the health status information by averaging or weight-averaging the three pieces of facial condition information.

FIGS. 61A through 61E are diagrams for describing a method of obtaining, by the device 100, health status information of a user from a face image of the user, and providing, by the device 100, a hospital related service based on the health status information, according to one or more exemplary embodiments.

Figure 61A:
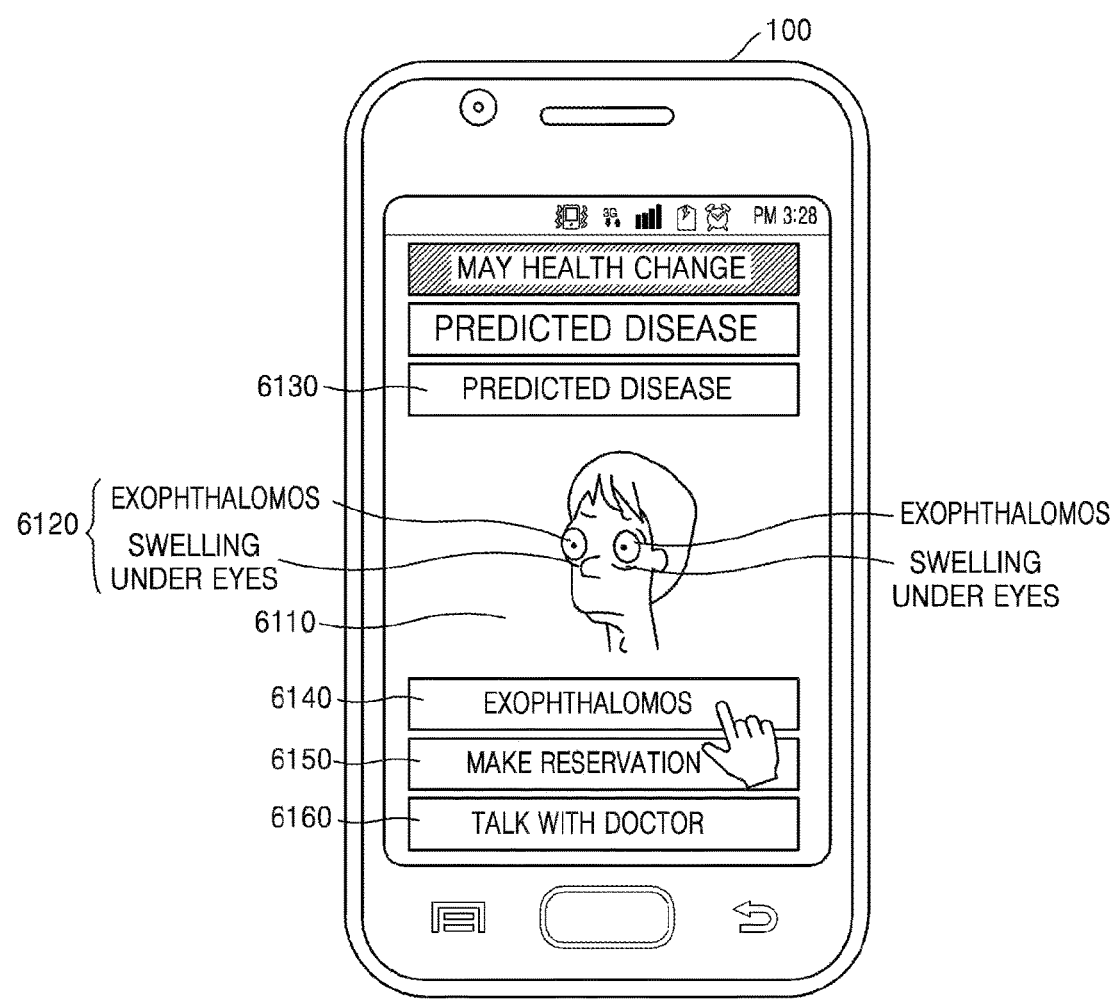
FIGS. 61A through 61E are diagrams for describing a method of obtaining, by a device, health status information of a user from a face image of the user, and providing, by the device, a hospital related service based on the health status information, according to one or more exemplary embodiments.

Referring to FIG. 61A, the device 100 may provide a hospital related service based on health status information 6130.

For example, upon receiving a user input of displaying the health status information 6130 obtained from a face image 6110, the device 100 may display or output the face image 6110, facial condition information 6120 obtained from the face image 6110, and the health status information 6130 obtained based on the facial condition information 6120. For example, the facial condition information 6120 may be exophthalomos and swelling under eyes, and the health status information 6130 may be hyperthyreosis.

Also, the device 100 may display or output a user interface for providing the hospital related service together with the facial condition information 6120 and the health status information 6130. For example, the device 100 may display a button 6140 for providing a reservation service, a button 6150 for displaying a list of nearby hospitals, and a button 6160 for talking to a doctor.

Figure 61B:
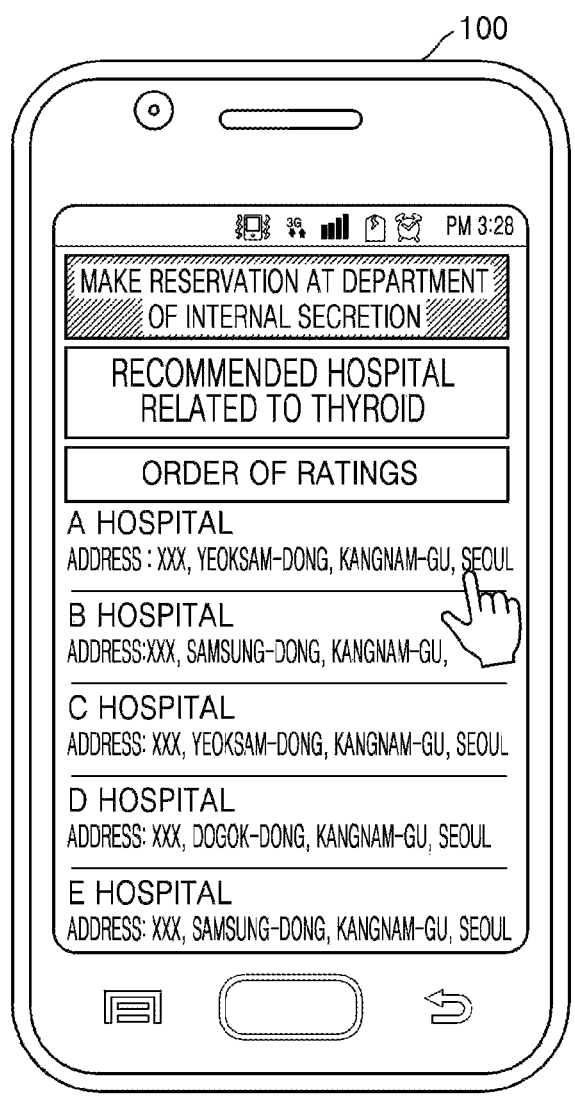

Referring to FIG. 61B, upon receiving a user input of selecting the button 6140 for providing a reservation service, the device 100 may display a user interface for making a reservation at a hospital related to health status information of a user.

For example, when the health status information is hyperthyreosis, the device 100 may display a list of hospitals related to thyroid. Here, the device 100 may receive the list of hospitals related to thyroid from a server (e.g., a third party server), and receive the list of hospitals related to thyroid from the service server 1000 connected to the third party server.

Figure 61C:
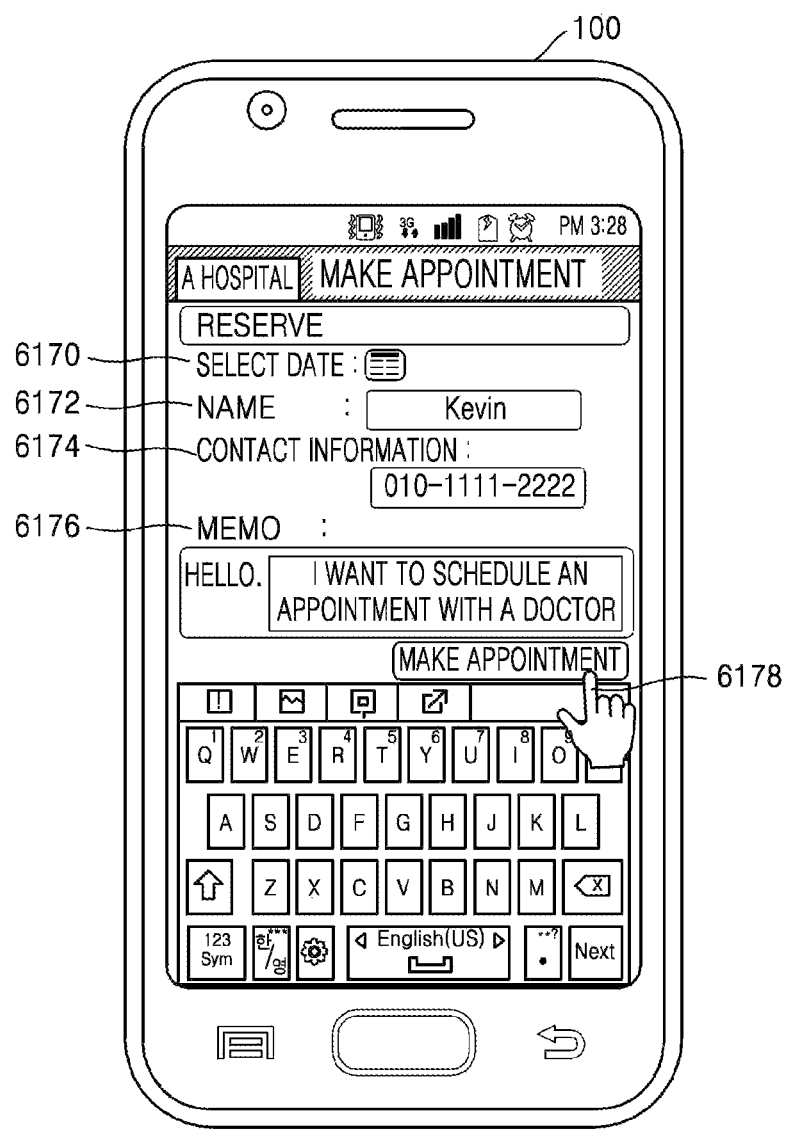

Referring to FIG. 61C, upon receiving a user input of selecting a hospital from a list of hospitals, the device 100 may provide a user interface for making a reservation at the selected hospital.

The user interface for making a reservation may include an item 6170 for selecting a date and time, an item 6172 for inputting a name of a user, an item 6174 for inputting contact information, and an item 6176 for inputting a memo.

When the items 6170 through 6176 are filled in and a user input of selecting a reservation button 6178 is received, the device 100 may transmit information in the items 6170 through 6176 to the service server 1000 or a third party server. Upon receiving information indicating that the reservation is made from the service server 1000 or the third party server, the device 100 may display a phrase indicating that the reservation is made.

Figure 61D:
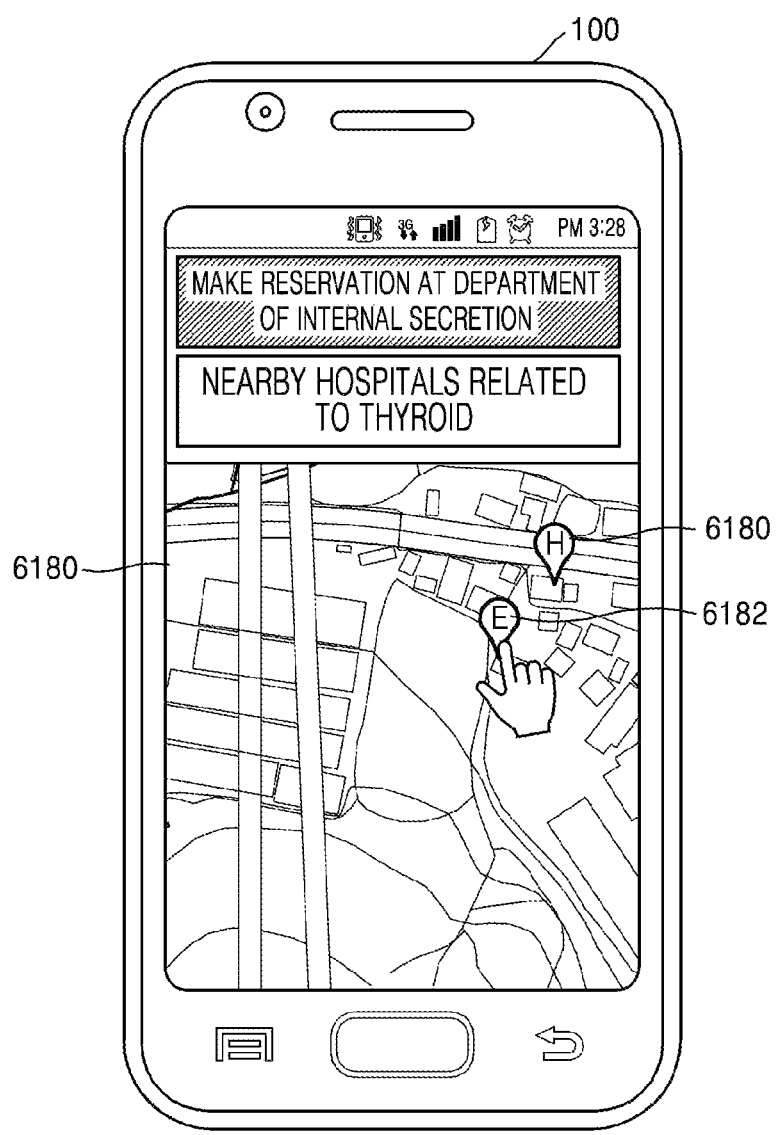

Referring to FIG. 61D, upon receiving a user input of selecting the button 6150 of FIG. 61A for displaying a list of nearby hospitals, the device 100 may provide location information about hospitals near a current location of a user based on location information of the device 100.

For example, the device 100 may obtain a current latitude and longitude of the device 100 by using a GPS included in the device 100. Based on the current latitude and longitude, the device 100 may provide a hospital related to health status information of the user, from among the hospitals near the current location of the user. At this time, the device 100 may display a map 6180 showing locations of hospitals.

For example, the device 100 may display locations 6181 through 6186 of hospitals specializing in internal secretion handling hyperthyreosis on the map 6180, from among hospitals near the current location of the user.

Figure 61E:
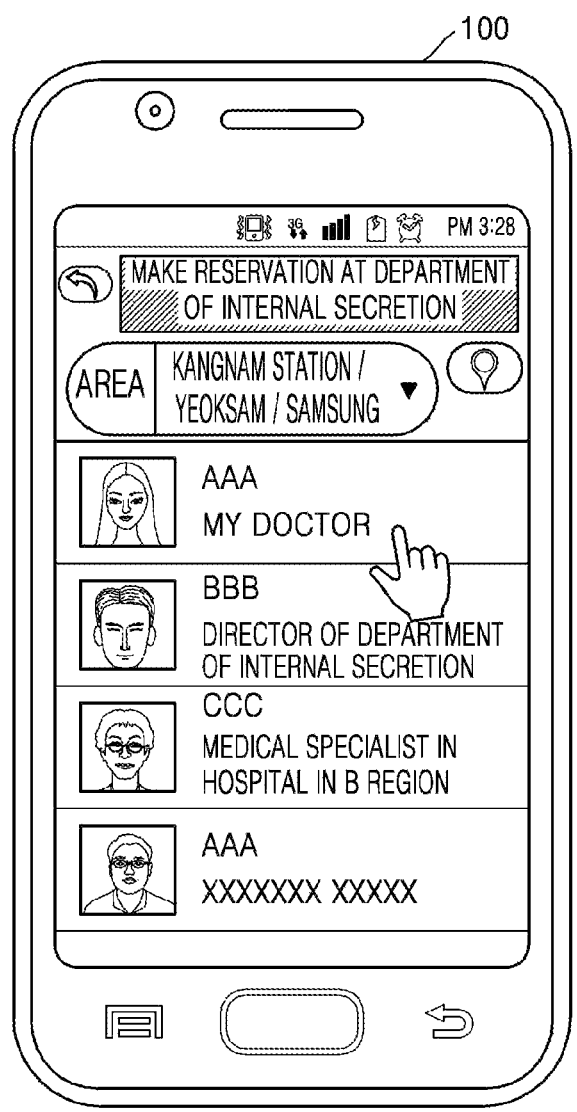

Referring to FIG. 61E, upon receiving a user input of selecting the button 6160 of FIG. 61A for talking with a doctor, the device 100 may provide a list of doctors.

For example, upon receiving the user input of selecting the button 6160, the device 100 may provide a list of doctors related to health status information of a user. Here, the device 100 may transmit the health status information to the service server 1000 or a third party server, receive the list of doctors from the service server 1000 or the third party server, and display the list of doctors.

Upon receiving a user input of selecting a doctor from the list of doctors, the device 100 may transmit ID information of the selected doctor to the service server 1000 or the third party server, and display a chat window for talking with the selected doctor.

FIG. 62 is a database 6200 of health status information 6230 and 6240 extractable from facial condition information 6220 and prescription information 6250 according to the health status information 6230 and 6240, according to an exemplary embodiment.

Referring to FIG. 62, the device 100 or the service server 1000 may store the health status information 6230 and 6240 extractable from the facial condition information 6220 and the prescription information 6250 according to the health status information 6230 and 6240, in a form of the database 6200. Here, the device 100 or the service server 1000 may store the facial condition information 6220, the health status information 6230 and 6240, and the prescription information 6250 according to regions 6210 of a face.

The device 100 or the service server 1000 may extract the health status information 6230 and 6240 from the facial condition information 6220, and obtain the prescription information 6250 from the health status information 6230 and 6240, based on the database 6200.

For example, when facial condition information is an inflamed eye, the device 100 or the service server 1000 may determine problems in a liver and a heart of a user as health status information. Also, the device 100 may determine accompanying symptoms to be dizziness, headache, cold sore in mouth, tinnitus, and dandruff. Also, the device 100 or the service server 1000 may determine no alcohol and regular exercise as prescription information.

Figure 63A:
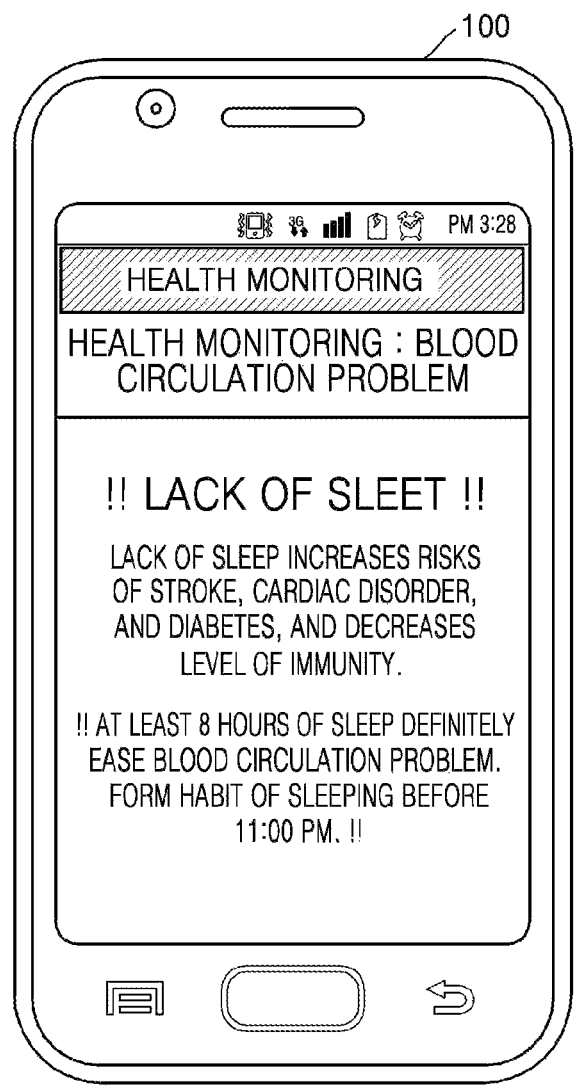
FIGS. 63A through 63C are diagrams for describing a method of providing, by a device, prescription information suitable to a user based on health status information of the user, according to one or more exemplary embodiments.
Figure 63B:
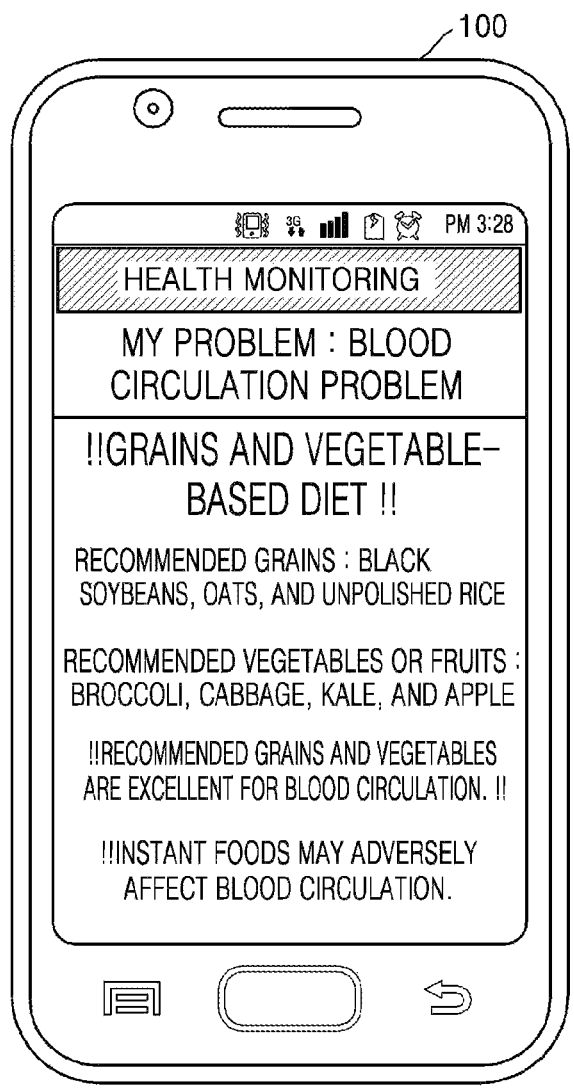
Figure 63C:
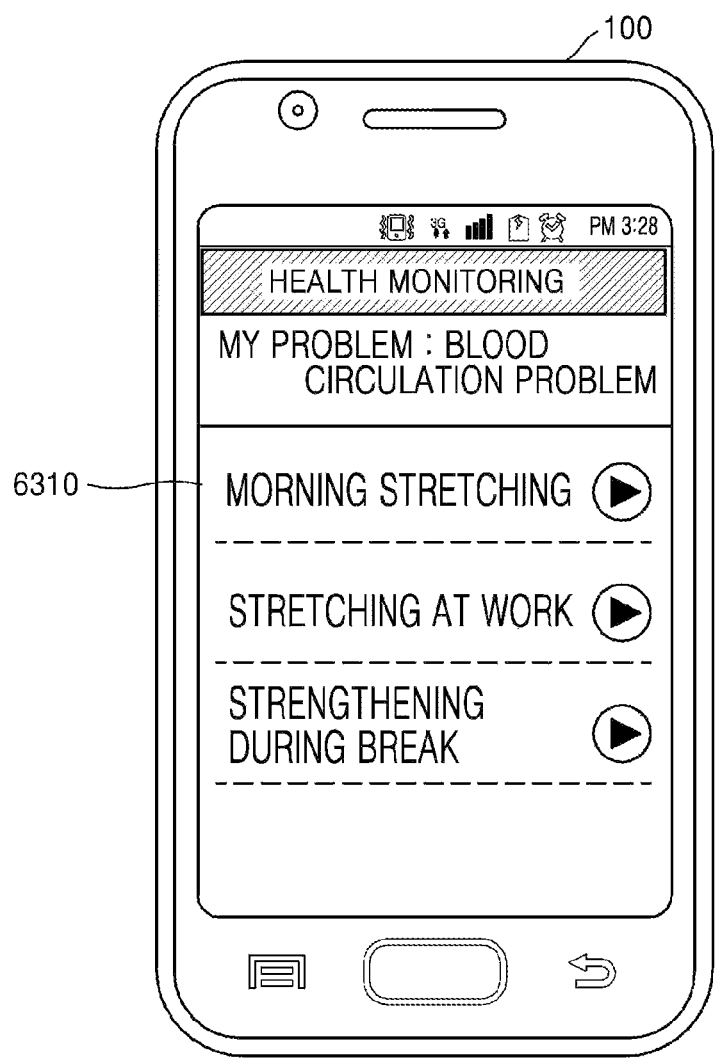

FIGS. 63A through 63C are diagrams for describing a method of providing, by the device 100, prescription information suitable to a user based on health status information of the user, according to exemplary embodiments.

Referring to FIG. 63A, the device 100 may provide the prescription information suitable to the user based on the health status information.

The device 100 may display information for changing life habits of the user based on the health status information.

For example, when the health status information indicates a blood circulation problem, the device 100 may display information for inducing the user to take enough sleep. Also, the device 100 may display symptoms caused by lack of sleep or an advice for changing a sleeping habit.

Referring to FIG. 63B, the device 100 may display information for changing eating habits of the user based on the health status information.

For example, when the health status information indicates a blood circulation problem, the device 100 may advise the user to mainly eat grains and vegetables. The device 100 may recommend grains or vegetables suitable to the user to improve a health status.

Referring to FIG. 63C, the device 100 may display exercise information helpful to the user based on the health status information.

For example, when the health status information indicates a blood circulation problem, the device 100 may display a page 6310 providing information about exercises under various circumstances. Upon receiving a user input of selecting "stretching at work" from various items in the page 6310, the device 100 may display stretches doable by the user at work.

Figure 64:
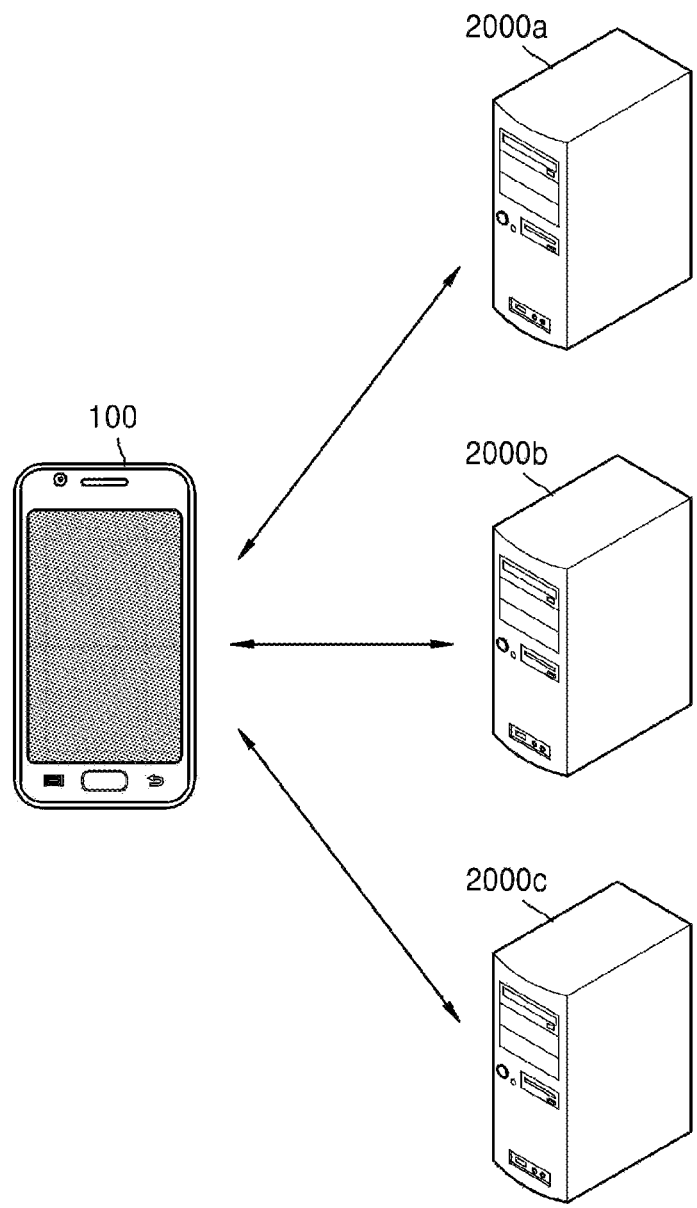
FIG. 64 is a diagram for describing a method of providing, by a device, a service related to health status information of a user to the user by interworking with a plurality of third party servers that provide health related information, according to an exemplary embodiment.

FIG. 64 is a diagram for describing a method of providing, by the device 100, a service related to health status information of a user to the user by interworking with a plurality of third party servers 2000a through 2000b that provide health related information, according to an exemplary embodiment.

Referring to FIG. 64, the third party servers 2000a through 2000c may be servers operated by different service providers.

For example, the third party server 2000a may be a server providing information about life habits suitable to the user. The third party server 2000b may be a server providing a diet therapy suitable to the user. Also, the third party server 2000c may be a server for recommending exercises suitable to the user.

The device 100 may transmit the health status information of the user obtained from a face image of the user to one of the third party servers 2000a through 2000c based on pre-stored address information of the third party servers 2000a through 2000c, and receive prescription information suitable to the user from the one of the third party servers 2000a through 2000c.

The one of the third party servers 2000a through 2000c may determine the prescription information based on the health status information received from the device 100, and provide the prescription information to the device 100. At this time, the prescription information may be provided in a form of text, image, or moving image, or may be provided in a form of a webpage including health information.

Figure 65:
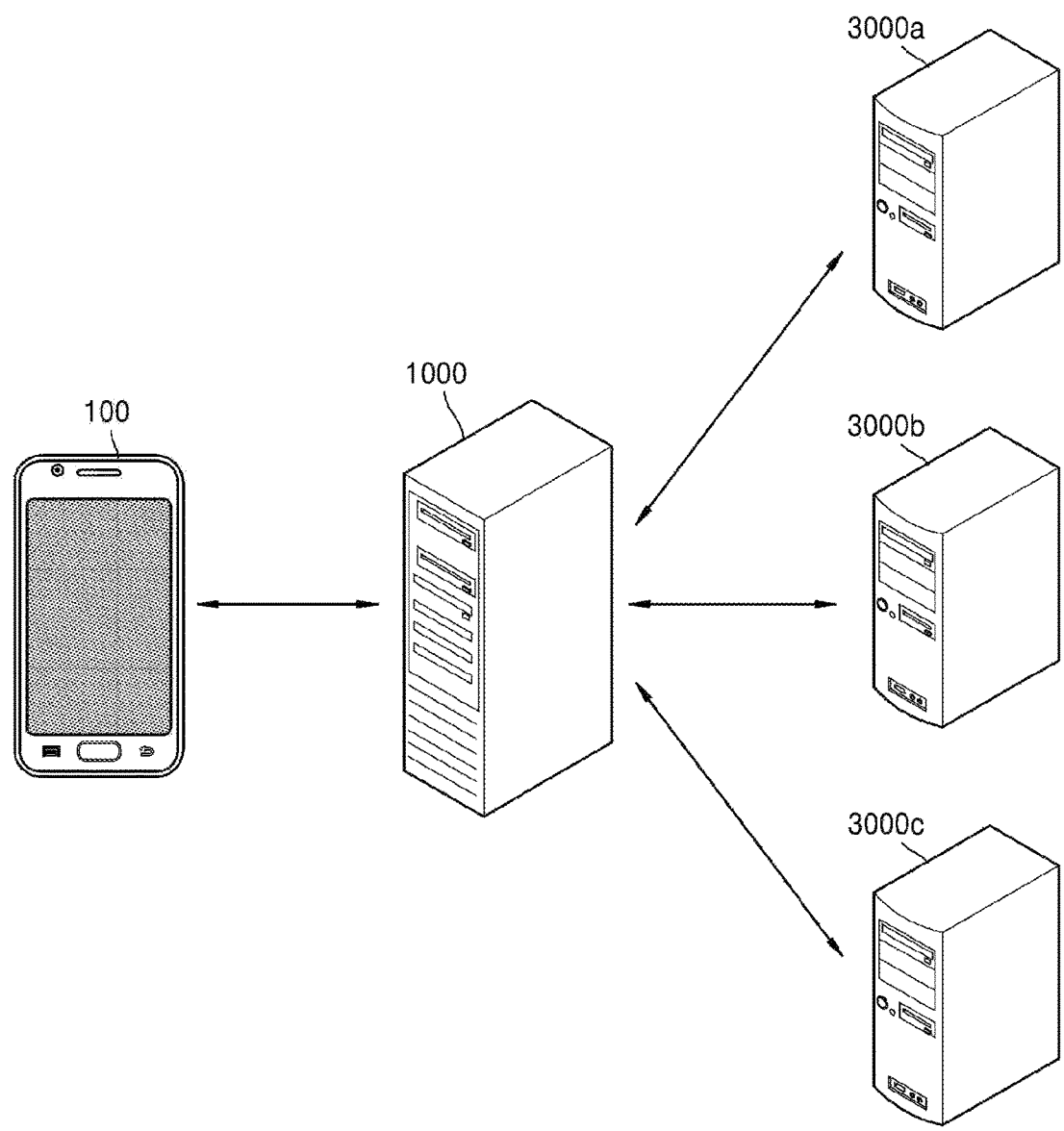
FIG. 65 is a diagram for describing a method of providing, by a device, a service provided by a third party server to a user through a service server, according to an exemplary embodiment.

FIG. 65 is a diagram for describing a method of providing, by the device 100, a service provided by third party servers 3000a through 3000b to a user through the service server 1000, according to an exemplary embodiment.

Referring to FIG. 65, the service server 1000 may be connected to the third party servers 3000a through 3000b that provide health related information.

The third party server 3000a may be a server operated by a hospital to provide a reservation service. The third party server 3000b may be a server operated by a service provider to provide a map service. Also, the third party server 3000c may be a server operated by a service provider to provide a messenger service.

The service server 1000 may store address information of each of the third party servers 3000a through 3000c. Upon receiving a request for a service from the device 100, the service server 1000 may determine a third party server for providing the requested service, and request the third party server for information required to provide the requested service. Upon receiving the requested information from the third party server, the service server 1000 may provide the requested service to the device 100 based on the received information.

For example, upon receiving a reservation service regarding a certain medical department from the device 100, the service server 1000 may request the third party server 3000a for information about an available date and time, and information about doctors regarding the certain medical department, and receive the requested information. Upon receiving the requested information from the third party server 3000a, the service server 1000 may transmit the received information to the device 100.

Upon receiving a reservation request regarding at least one of a date, time, and doctor selected by a user from the device 100, the service server 1000 may request the third party server 3000a to make an appointment with the doctor selected by the user on the date and time selected by the user.

Also, for example, upon receiving a request for a list of hospitals close to the user from the device 100, the service server 1000 may request the third party server 3000b for the list of hospitals. At this time, the service server 1000 may transmit latitude and longitude information of the device 100 to the third party server 3000b. Furthermore, the service server 1000 may transmit ID information of a certain medical department together with the latitude and longitude information to the third party server 3000b.

Upon receiving the list of hospitals from the third party server 3000b, the service server 1000 may transmit the received list to the device 100. Here, the service server 1000 may transmit information about locations of the hospitals, medical departments of the hospitals, or ratings of the hospitals, to the device 100.

Also, upon receiving a request to talk with a doctor at a certain medical department from the device 100, the service server 1000 may determine the doctor corresponding to the certain medical department from among a pre-stored plurality of doctors, based on ID information of the certain medical department. The service server 1000 may request the third party server 3000c for chatting with the determined doctor, based on messenger IDs of the pre-stored plurality of doctors. The service server 1000 may transmit a message received from the device 100 to the third party server 3000c, and transmit a message received from the third party server 3000c to the device 100, thereby providing a messenger service to the device 100.

Figure 66:
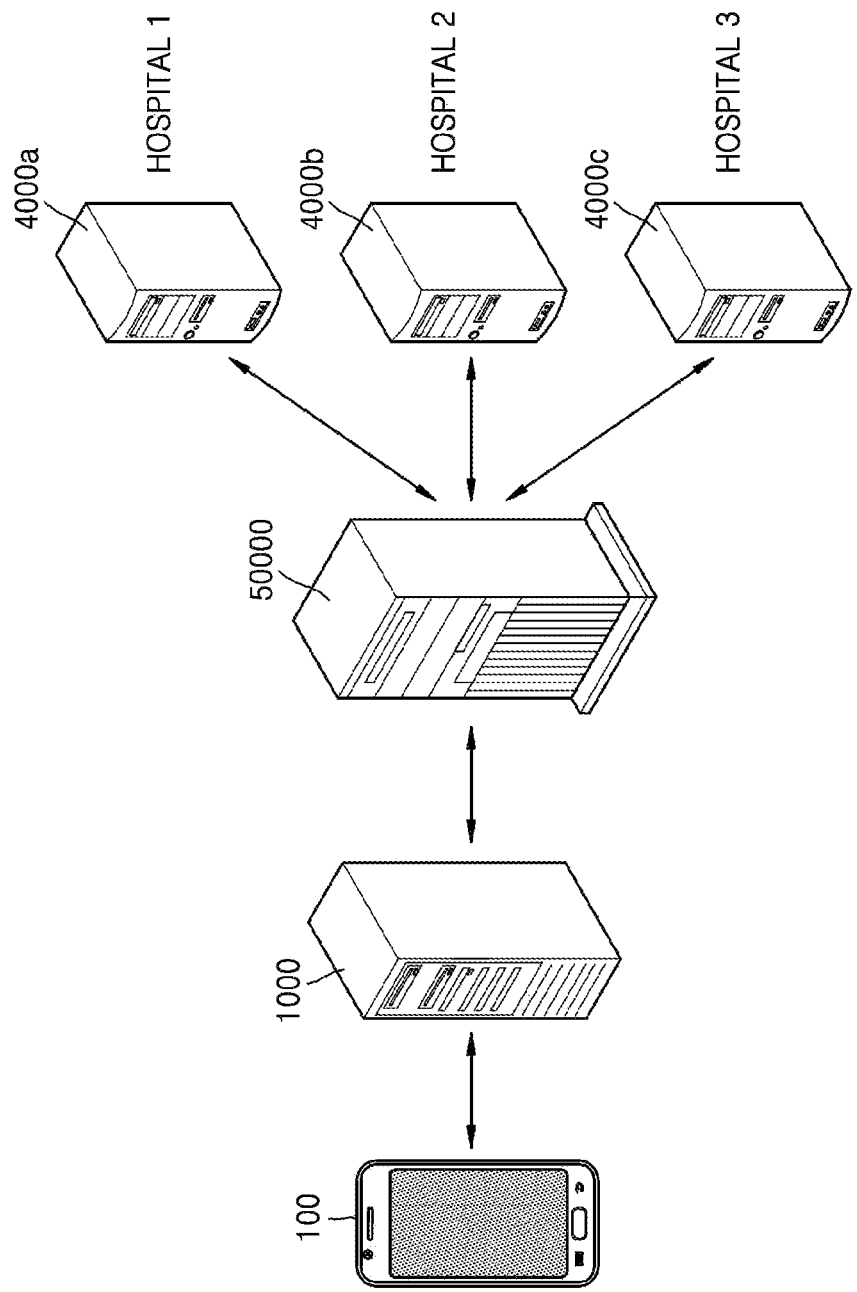
FIG. 66 is a diagram for describing a method of providing, by a device, services provided by third party servers to a user, by using a service server interworking with an integrated server of the third party servers, according to an exemplary embodiment.

FIG. 66 is a diagram for describing a method of providing, by the device 100, services provided by third party servers 4000a through 4000c to a user, by using the service server 1000 interworking with an integrated server 5000 of the third party servers 4000a through 4000c, according to an exemplary embodiment.

Referring to FIG. 66, the service server 1000 may provide the services provided by the third party servers 4000a through 4000c to the device 100 by interworking with the integrated server 5000.

The integrated server 5000 may be a server that transmits and receives information to and from the third party servers 4000a through 4000c. For example, when the third party servers 4000a through 4000c are hospital servers operated by different hospitals, the integrated server 5000 may be a server that transmits and receives information to and from the third party servers 4000a through 4000c. In this case, the integrated server 5000 may store address information of the hospitals operating the third party servers 4000a through 4000c.

Upon receiving a reservation service regarding a certain medical department from the device 100, the service server 1000 may request the integrated server 5000 for information about available dates and times and information about doctors regarding the certain medical department. Upon receiving a reservation request from the service server 1000, the integrated server 5000 may request the third party servers 4000a through 4000c registered in the integrated server 5000 for information required to make a reservation at the certain medical department.

Upon receiving the information about available dates and times and information about doctors from the third party servers 4000a through 4000c, the integrated server 5000 may transmit the received information to the service server 1000. At this time, the integrated server 5000 may transmit the received information together with ID information of the hospitals to the service server 1000.

Upon receiving the information required to make a reservation from the integrated server 5000, the service server 1000 may transmit the received information to the device 100.

Upon receiving user inputs of selecting one of the hospitals, and selecting a date, a time, and a doctor, the device 100 may transmit information about the user inputs to the service server 1000. Upon receiving the information about the user inputs from the device 100, the service server 1000 may request the integrated server 5000 to make a reservation, and the integrated server 5000 may make a reservation based on the received information about the user inputs.

Figure 67:
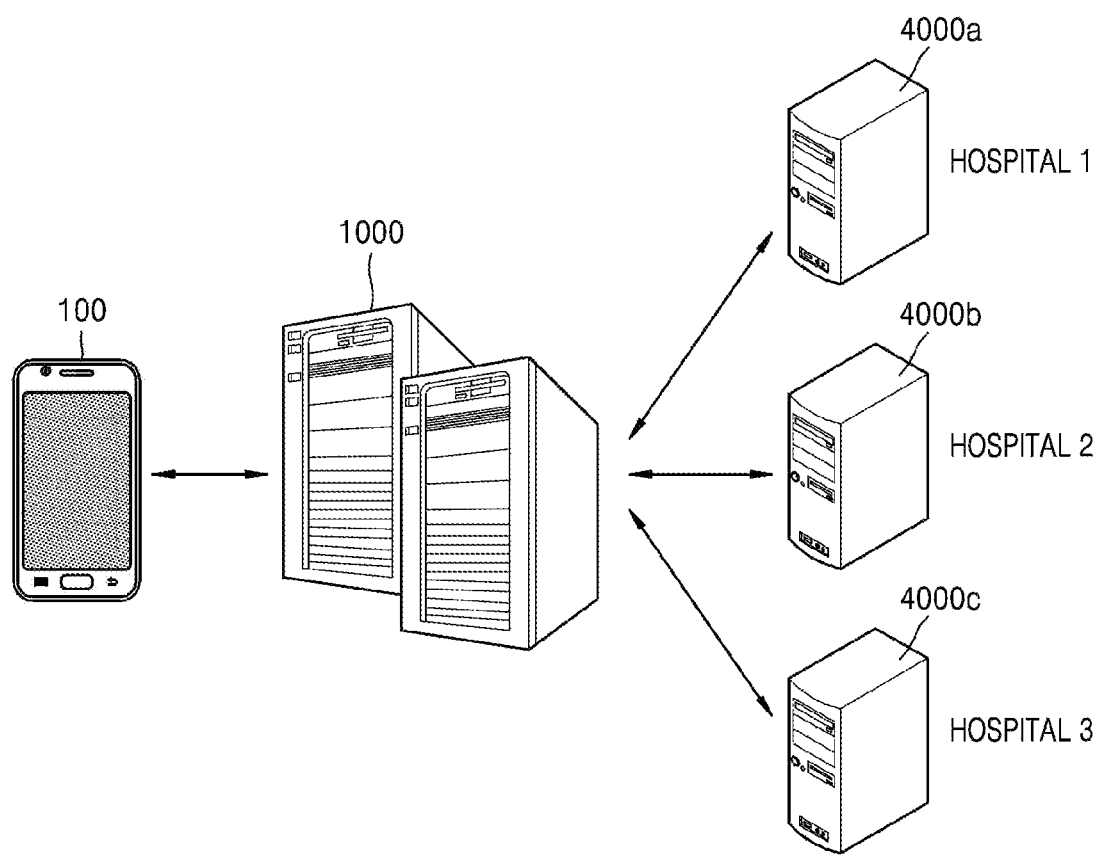
FIG. 67 is a diagram for describing a method of providing, by a device, services provided by third party servers by using a service server, when the service server operates as an integrated server, according to an exemplary embodiment.

FIG. 67 is a diagram for describing a method of providing, by the device 100, services provided by the third party servers 4000a through 4000b by using the service server 1000, when the service server 1000 operates as an integrated server, according to an exemplary embodiment.

Referring to FIG. 67, the service server 1000 may perform functions of the integrated server 5000 of FIG. 65.

For example, a service provider operating the service server 1000 may operate the service server 1000 and the integrated server 5000 together. In this case, the service server 1000 may be one server that performs the functions of the service server 1000 and the integrated server 5000 at the same time. Alternatively, the service server 1000 may be divided into a plurality of servers, e.g., a server that performs the functions of the service server 1000 and a server that performs the functions of the integrated server 5000.

Figure 68:
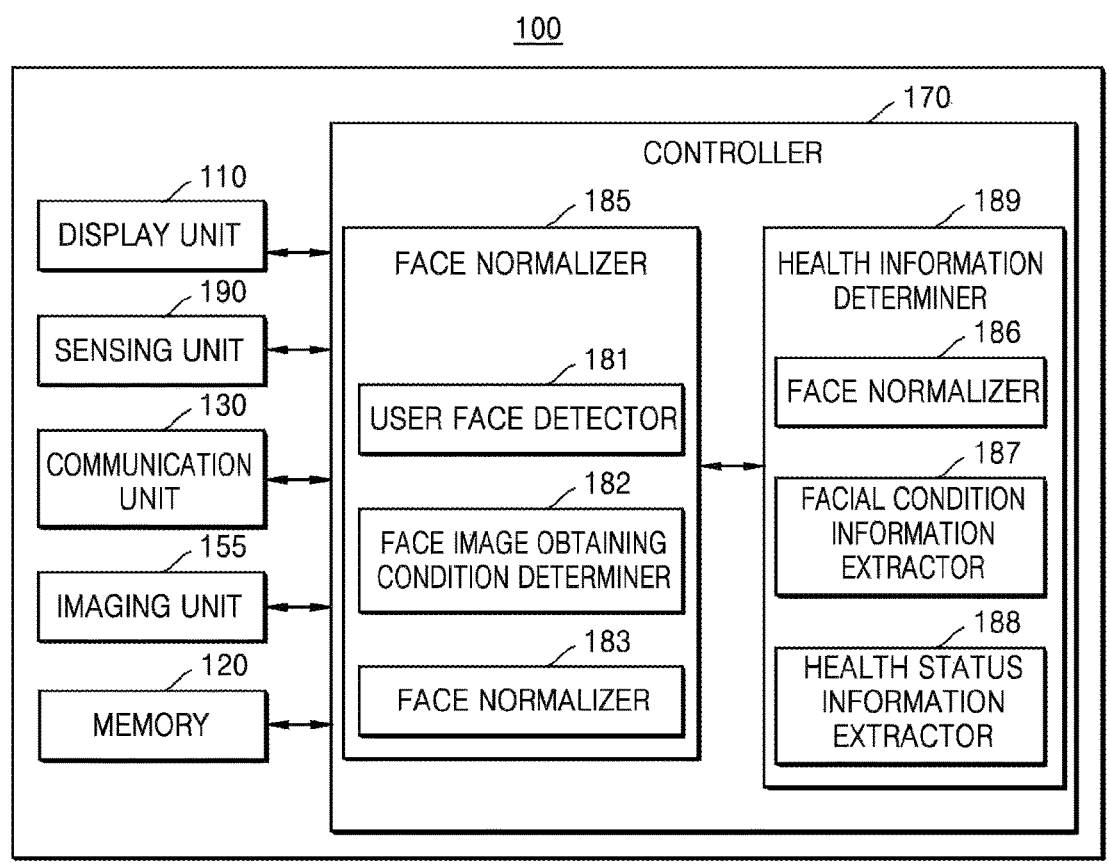
FIG. 68 is a block diagram of a device according to an exemplary embodiment.

FIG. 68 is a block diagram of the device 100 according to an exemplary embodiment.

As shown in FIG. 68, the device 100 according to an exemplary embodiment may include a display unit 110 (e.g., display), a sensing unit 190 (e.g., sensor), a communication unit 130 (e.g., communicator), an imaging unit 155 (e.g., imager), a memory 120, and a controller 170. However, it is understood that in one or more other exemplary embodiments, the device 100 may include more or less components than those shown in FIG. 68. For example, according to another exemplary embodiment, the device 100 may not include the display unit 110 and/or may include an outputter (e.g., output device) configured to output information and/or images for display (e.g., output information and/or images to an external display).

The device 100 may obtain an input image showing a face of a user. For example, the device 100 may obtain an input image by capturing a template of the face of the user according to a pre-set face image obtaining condition. At this time, the display unit 110 may display guide information for capturing the face according to the pre-set face image obtaining condition, on a screen. When the face of the user approaches the imaging unit 155, the device 100 may receive the input image through the imaging unit 155. According to another exemplary embodiment, the device 100 may obtain one or more images and/or input images from a storage (e.g., an internal storage or an external storage).

The imaging unit 155 generates an electric imaging signal by performing photoelectric conversion on an incident light. The imaging unit 155 may include at least one of a lens, an iris, and an image pickup device. Also, the imaging unit 155 may be a mechanical shutter type or an electronic shutter type.

According to the current exemplary embodiment, the input image may be captured by using the imaging unit 155. The input image may include, for example, at least one of a captured image, a preview image, and a moving image captured by the imaging unit 155.

According to an exemplary embodiment, when the user captures an image by using the imaging unit 155 and the captured image satisfies the pre-set face image obtaining condition, the controller 170 may use the captured image as a face image. According to another exemplary embodiment, when the captured image satisfies the pre-set face image obtaining condition, a message inquiring the user whether to use the captured image as a face image for a health examination may be output, and the captured image may be used as the face image based on user's selection. According to an exemplary embodiment, a face image for a health examination may be collected without having to perform special manipulation even when the face image is captured in a normal mode.

According to another exemplary embodiment, a face image may be captured in a certain mode provided by the device 100. The certain mode may be, for example, at least one of a face authentication mode for unlocking the device 100 via face authentication, a selfie mode, or a person photographing mode.

A pre-set photographing parameter may be set in the imaging unit 155. The pre-set photographing parameter may include, for example, at least one of an iris value, whether to use a flash, or a white balance condition.

The controller 170 may automatically capture an image when a preview image in a health examination mode satisfies the pre-set face image obtaining condition, and use the captured image as a face image.

When an image is captured according to an input of a shutter release signal in a health examination mode, the controller 170 may determine whether the captured image satisfies the pre-set face image obtaining condition, and the display unit 110 may provide information about whether the pre-set face image obtaining condition is satisfied. Alternatively, when the captured image satisfies the face image obtaining condition, the controller 170 may use the captured image as a face image.

Alternatively, the device 100 may receive an input image from an external network connected to the device 100, through the communication unit 130.

Upon receiving the input image, the controller 170 may store the input image in the memory 120. Alternatively, the controller 170 may obtain a face image from the input image.

The controller 170 may obtain the face image from the input image by using an image processor 185. The image processor 185 may include a user face detector 181, a face image obtaining condition determiner 182, and a face normalize 183.

The user face detector 181 may detect a face region of a person from the input image, and extract a location of the face region. Upon extracting the location of the face region, the user face detector 181 may extract features of the face from the face region. A method of extracting the features of the face from the face region may be a Gabor filter method or a LBP method.

The user face detector 181 may determine the face region extracted from the input image to be a face region of the user when similarity between the extracted features and pre-registered features of the faces of the user is within a pre-set range.

Upon determining the face region of the user, the face image obtaining condition determiner 182 may determine whether the input image satisfies a pre-set face image obtaining condition. For example, the device 100 may determine illumination of the input image is within a base range. Alternatively, the device 100 may determine whether a camera is shaken while capturing the input image.

Also, the face image obtaining condition determiner 182 may determine whether a face in the face region extracted from the input image satisfies the pre-set face image obtaining condition.

For example, the face image obtaining condition determiner 182 may determine whether an angle of the face is within a base angle range from a front face. Alternatively, the face image obtaining condition determiner 182 may determine whether eyes of the face in the input image are opened. Alternatively, the face image obtaining condition determiner 182 may determine a facial expression in the input image. Alternatively, the face image obtaining condition determiner 182 may determine whether ears are seen in the input image. Alternatively, the face image obtaining condition determiner 182 may determine whether a size of the face in the input image is equal to or larger than a base size.

When the input image satisfies the pre-set face image obtaining condition, the controller 170 may obtain an image of the face region from the input image as a face image.

Upon obtaining the image of the face region from the input image as a face image, the face normalizer 183 may normalize the face image to a pre-set standard.

For example, the face normalizer 183 may change a size of the face image to a pre-set size. Alternatively, the face normalizer 183 may adjust an effect of a color temperature of illumination on the face image. Alternatively, the face normalizer 183 may change brightness of the face image to pre-set brightness.

After normalizing the face image, the controller 170 may determine health status information based on the face image by using a health information determiner 189. The health information determiner 189 may include a diagnosis region extractor 186, a facial condition information extractor 187, and a health status information extractor 188.

The diagnosis region extractor 186 may determine a diagnosis region from which pre-set facial condition information is to be extracted, from the face image.

For example, the diagnosis region extractor 186 may determine locations of facial components from the face image. The facial components may be at least one of eyes, a nose, and a mouth. The diagnosis region extractor 186 may binarize the face image and determine dark regions in the binarized face image as eyes, eyebrows, and a mouth based on facts that brightness of eyes, eyebrows, and a mouth is darker than a skin color. Alternatively the diagnosis region extractor 186 may extract regions that are not in a skin color from the face image by using skin color information, and determine the extracted regions as locations of the eyes, the nose, and the mouth. Since the locations of the eyes, the eyebrows, the nose, and the mouth show a certain pattern, the diagnosis region extractor 186 may determine the locations of the facial components by using an AAM method in which locations of facial components are determined based on a face pattern.

After determining the locations of the facial components, the diagnosis region extractor 186 may determine a location of the diagnosis region based on the locations of the facial components.

After determining the location of the diagnosis region, the facial condition information extractor 187 may extract facial condition information from the diagnosis region.

The facial condition information may denote a status of a face that is referenced to determine health information.

Types of facial condition information extractable according to the diagnosis region and methods of extracting the facial condition information may be pre-stored in the memory 120.

The facial condition information may be extracted by analyzing the face image. For example, the facial condition information extractor 187 may extract the facial condition information by using color information of the face region, a face recognition algorithm, or a facial expression recognition algorithm.

After extracting the facial condition information, the health status information extractor 188 may obtain health status information related to health of the user by using the facial condition information.

The health status information may be about a disease or a lifestyle of the user predicted from the facial condition information. For example, when regions under the eyes are determined to be swollen from the face image, the device 100 may determine that the user has hyperthyroidism or an allergic trouble. Alternatively, when the regions under the eyes are determined to be black from the face image, the device 100 may determine that the user has allergic rhinitis.

The controller 170 may provide the health status information through the display unit 110.

The controller 170 may obtain the face image from an image file stored in the memory 120. Also, the controller 170 may provide a user interface for browsing image files stored in the memory 120 via a function of a photo album or a gallery.

At least one image file may be stored in the memory 120. The image file may be a still image file or a moving image file. The memory 120 may store an image file generated from a captured image and/or an image file received from an external device. The image file may be in a joint photographic coding experts group (JPEG) format, a moving picture expert group (MPEG) format, an MP4 format, an audio visual interleaving (AVI) format, or an advanced streaming format (ASF).

The device 100 according to an exemplary embodiment may include the sensing unit 190. In this case, the device 100 may obtain the facial condition information and the health status information by using bio-parameter detected by the sensing unit 190. Examples of the bio-parameter include at least one of blood pressure, a heart rate, blood sugar, an acidity level, concentration of hemoglobin in blood, and oxygen saturation. For example, the sensing unit 190 may be a sensor for detecting at least one of a heart rate, a blood pressure measuring sensor, or an acidity level measuring sensor.

According to an exemplary embodiment, the controller 170 may receive the facial condition information and the health status information from the user through a user input unit (e.g., user inputter or user input device such as a physical button, a joystick, a touch pad, a track pad, a mouse device, a peripheral device, a rotatable dial, an audio input device such as a microphone, a visual input device such as a camera or a gesture detector, etc.), and obtain new facial condition information and new health status information by using the received facial condition information and the received health status information together with the face image. The facial condition information received from the user may include a height, a weight, an age, or blood pressure of the user. The health status information received from the user may include a chronic disease, a past medical history, a family history, and current condition information.

The facial condition information and the health status information received from the user may be stored and managed as separate files, managed by an application, or managed by a service server. Alternatively, the facial condition information and the health status information received from the user may be managed according to users.

The communication unit 130 may communicate with an external device. The communication unit 130 may communicate with the external device via wire or wirelessly (e.g., a transceiver, a network adapter, a wireless interface, a universal serial bus interface, a wired interface, etc.). According to an exemplary embodiment, the communication unit 130 may communicate with a cloud server, an SNS server, or a service server that provides a health examination service. Alternatively, the communication unit 130 may communicate with another electronic device, such as a smart phone, a camera, a tablet personal computer (PC), a smart device, a wearable device, a personal digital assistant (PDA), a laptop, a mobile phone, etc.

The device 100 may be in a form of a smart phone, a tablet PC, a mobile phone, a camera, a laptop, a PDA, a smart device, a wearable device, etc.

Figure 69:
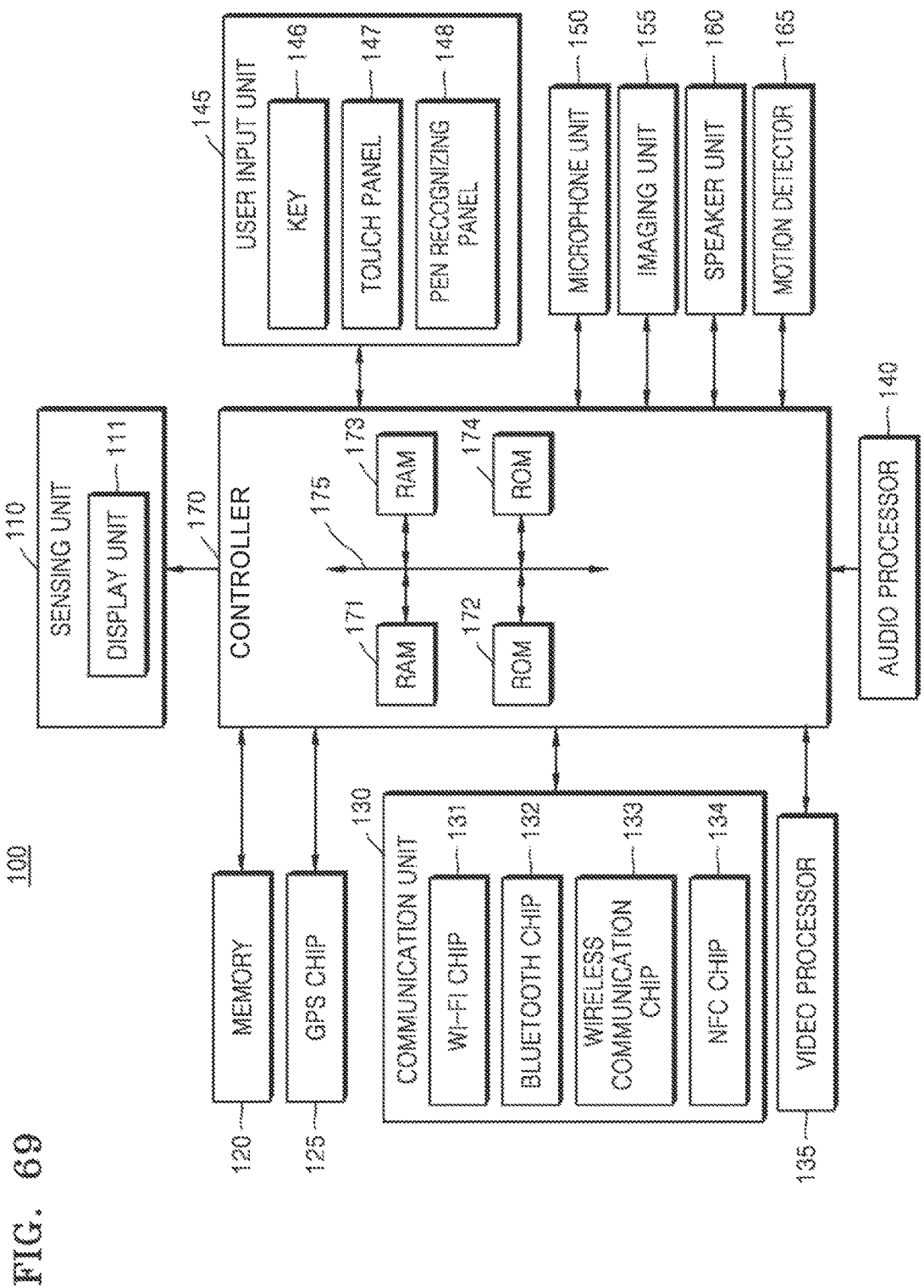
FIG. 69 is a block diagram of a device according to another exemplary embodiment.

FIG. 69 is a block diagram of the device 100 according to another exemplary embodiment.

As shown in FIG. 69, the device 100 may be applied to any of various devices, such as a camera, a mobile phone, a tablet PC, a PDA, an MP3 player, a kiosk, an electronic frame, a navigation device, a digital TV, a wrist watch, a head-mounted display (HMD), etc.

Referring to FIG. 69, the device 100 may include at least one of the display unit 110, the controller 170, the memory 120, a global positioning system (GPS) chip 125, the communication unit 130, a video processor 135, an audio processor 140, a user input unit 145, a microphone unit 150 (e.g., microphone), the imaging unit 155, a speaker unit 160, and a motion detector 165.

Also, the display unit 110 may include a display panel 111 and a controller that controls the display panel 111. The display panel 111 may be realized in a display of any type, such as a liquid crystal display (LCD), an organic light-emitting diode (OLED) display, an active-matrix OLED (AM-OLED), a plasma display panel (PDP), etc. The display panel 111 may be at least one of flexible, transparent, or wearable. The display unit 110 may be provided as a touch screen by being combined with a touch panel 147 of the user input unit 145. For example, the touch screen may include an integrated module in which the display panel 111 and the touch panel 147 are combined in a stacked structure.

The memory 120 may include at least one of an internal memory and an external memory.

Examples of the internal memory include volatile memories (for example, a dynamic random access memory (DRAM), a static RAM (SRAM), and a synchronous DRAM (SDRAM)), nonvolatile memories (for example, a one-time programmable read-only memory (OTPROM), a programmable ROM (PROM), an erasable and programmable ROM (EPROM), an electrically erasable and programmable ROM (EEPROM), a mask ROM, and a flash ROM), a hard disk drive (HDD), a solid state drive (SSD), etc. According to an exemplary embodiment, the controller 170 may load, on a volatile memory, a command or data received from at least one of nonvolatile memories or other components, and process the command or data. Also, the controller 170 may store data received from or generated by other components in a nonvolatile memory.

Examples of the external memory include a compact flash (CF) memory, a secure digital (SD) memory, a micro SD memory, a mini-SD memory, an extreme digital (XD) memory, a memory stick, etc.

The memory 120 may store various programs and data used to operate the device 100. For example, the memory 120 may temporarily or semi-permanently store at least a part of content to be displayed on a lock screen.

The controller 170 may control the display unit 110 such that a part of content stored in the memory 120 is displayed on the display unit 110. In other words, the controller 170 may display the part of the content stored in the memory 120 on the display unit 110. Alternatively, the controller 170 may perform a control operation corresponding to a user gesture when the user gesture is performed on one region of the display unit 110.

The controller 170 may include at least one of a RAM 171, a ROM 172, a central processing unit (CPU) 173, a graphic processing unit (GPU) 174, a bus 175, etc. The RAM 171, the ROM 172, the CPU 173, and the GPU 174 may be connected to each other via the bus 175.

The CPU 173 accesses the memory 120 and performs booting by using an operating system (OS) stored in the memory 120. Also, the CPU 173 performs various operations by using various programs, contents, and data stored in the memory 120.

Command sets for system booting are stored in the ROM 172. For example, when power is supplied to the device 100 as a turn-on command is input, the CPU 173 may copy an operating system (OS) stored in the memory 120 to the RAM 171 according to a command stored in the ROM 172, and execute the OS for the system booting. When the system booting is completed, the CPU 173 copies various programs stored in the memory 120 to the RAM 171, and executes the programs copied in the RAM 171 to perform various operations. When the system booting is completed, the GPU 174 displays a user interface screen in a region of the display unit 110. In detail, the GPU 174 may generate a screen displaying an electronic document including various objects, such as content, an icon, and a menu. The GPU 174 calculates attribute values, such as coordinate values, shapes, sizes, and colors, of the various objects according to a layout of the screen. Then, the GPU 174 may generate the screen having any one of various layouts based on the calculated attribute values. The screen generated by the GPU 174 may be provided to the display unit 110 and displayed on each region of the display unit 110.

The GPS chip 125 may receive a GPS signal from a GPS satellite, and calculate a current location of the device 100. The controller 170 may calculate the location of the device 100 by using the GPS chip 125 when a navigation program is used or when a current location of the user is required.

The communication unit 130 may communicate with an external device by using any one of various communication methods. The communication unit 130 may include at least one of a Wi-Fi chip 131, a Bluetooth chip 132, a wireless communication chip 133, and a near-field communication (NFC) chip 134. The controller 170 may communicate with any one of various external devices by using the communication unit 130.

The Wi-Fi chip 131 and the Bluetooth chip 132 may perform communication by respectively using a Wi-Fi method and a Bluetooth method. When the Wi-Fi chip 131 or the Bluetooth chip 132 is used, various types of connection information, such as subsystem identification (SSID) or a session key, are first transferred, and then various types of information may be transferred by using the connection information. The wireless communication chip 133 is a chip that performs communication according to any one of various communication standards, such as IEEE, Zigbee, third generation (3G), third generation partnership project (3GPP), and LTE. The NFC chip 134 is a chip that operates by using an NFC method using a frequency band of 13.56 MHz from among radio frequency identification (RFID) frequency bands, such as 135 kHz, 13.56 MHz, 433 MHz, 860 through 960 MHz, and 2.45 GHz.

The video processor 135 may process video data included content received through the communication unit 130 or included in content stored in the memory 120. The video processor 135 may perform various image processes, such as decoding, scaling, noise-filtering, frame rate changing, and resolution changing, on video data.

The audio processor 140 may process audio data included in content received through the communication unit 130 or included in content stored in the memory 120. The audio processor 140 may perform various processes, such as at least one of decoding, amplifying, and noise-filtering, on audio data.

When a reproduction program regarding multimedia content is executed, the controller 170 may reproduce the multimedia content by driving the video processor 135 and the audio processor 140. The speaker unit 160 (e.g., speaker) may output audio data generated by the audio processor 140.

The user input unit 145 may receive various commands from the user. The user input unit 145 may include at least one of a key 146, the touch panel 147, and a pen recognizing panel 148.

The key 146 may include various types of keys, such as a mechanical button and a wheel, which are formed on various regions, such as a front region, a side region, and a rear region, of an external body of the device 100.

The touch panel 147 may detect a touch input of the user, and output a touch event value corresponding to the touch input. When the touch panel 147 forms a touch screen by combining with the display panel 111, the touch screen may include as a touch sensor in any type, such as an electrostatic type, a pressure type, or a piezoelectric type. The electrostatic type touch sensor calculates a touch coordinate by detecting micro-electricity induced by a body of the user when the body of the user touches a surface of the touch screen, by using a dielectric substance coated on the surface of the touch screen. The pressure type touch sensor calculates a touch coordinate by detecting a current generated as upper and lower electrode plates included in the touch screen contact each other when the user touches the touch screen. A touch event generated on the touch screen may be mainly generated by a finger of the user, but may alternatively be generated by an object formed of a conductive material that may generate a change in electrostatic capacitance.

The pen recognizing panel 148 may detect a proximity input or a touch input of a touch pen, such as a stylus pen or a digitizer pen, and output a pen proximity event or a pen touch event. The pen recognizing panel 148 may use an electromagnetic radiation (EMR) method, and detect the proximity input or the touch input based on a change of intensity of an electromagnetic field, which is caused by approach or touch of the touch pen. In detail, the pen recognizing panel 148 may include an electron inducing coil sensor having a grid structure, and an electronic signal processor that provides an alternating signal having a certain frequency sequentially to loop coils of the electron inducing coil sensor. When a pen including a resonance circuit is near the loop coil of the pen recognizing panel 148, a magnetic field transmitted from the loop coil generates a current based on mutual electron induction, in the resonance circuit. Then, based on the current, an induction magnetic field is generated from a coil forming the resonance circuit, and the pen recognizing panel 148 detects the induction magnetic field from a loop coil in a signal reception state, thereby detecting a proximity or touch location of the pen. The pen recognizing panel 148 may have an area for covering a certain area below the display panel 111, for example, a display region of the display panel 111.

The microphone unit 150 may change or process user's voice or other sound to audio data. The controller 170 may use the user's voice for a call operation, or store the audio data in the memory 120.

The imaging unit 155 may capture a still image or a moving image based on control of the user. The imaging unit 155 may include a plurality of cameras, such as a front camera and a rear camera.

When the imaging unit 155 and the microphone unit 150 are provided, the controller 170 may perform a control operation according user's voice input through the microphone unit 150 or user motion recognized by the imaging unit 155. For example, the device 100 may operate in a motion control mode or a voice control mode. When the device 100 is in a motion control mode, the controller 170 may activate the imaging unit 155 to photograph the user, and perform a control operation by tracking a motion change of the user. When the device 100 is in a voice control mode, the controller 170 may analyze user's voice input through the microphone unit 150, and perform a control operation based on the analyzed user's voice.

The motion detector 165 may detect movement of the body of the device 100. The device 100 may rotate or tilt in any one of various directions. At this time, the motion detector 165 may detect a movement characteristic, such as a rotation direction, a rotation angle, or a tilted angle, by using at least one of various sensors, such as a terrestrial magnetic sensor, a gyro sensor, and an acceleration sensor.

Furthermore, according to one or more exemplary embodiments, the device 100 may further include a universal serial bus (USB) port to which a USB connector is connected, various external input ports to which various external terminals, such as a headset, a mouse, and a LAN cable, are connected, a digital multimedia broadcasting (DMB) chip that receives and processes a DMB signal, and various sensors.

Figure 70:
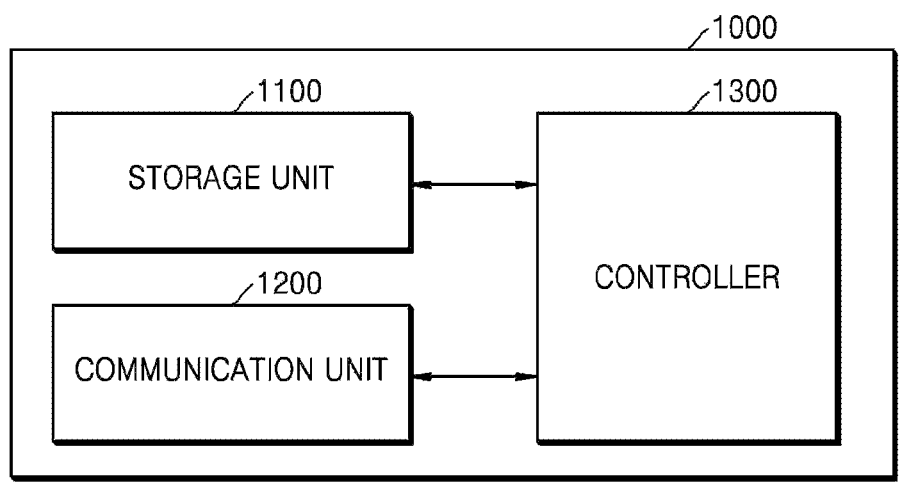
FIG. 70 is a block diagram of a service server according to an exemplary embodiment.

FIG. 70 is a block diagram of the service server 1000 according to an exemplary embodiment.

Referring to FIG. 70, the service server 1000 may include a storage unit 1100 (e.g., storage), a communication unit 1200 (e.g., communicator), and a controller 1300. However, it is understood that in one or more other exemplary embodiments, the service server 1000 may include more or less components than those shown in FIG. 70.

The storage unit 1100 may store information used to extract the health status information of the user from the face image of the user.

The storage unit 1100 may store the account information of the user. Also, the storage unit 1100 may store the face image of the user correspondingly to the account information of the user. Furthermore, the storage unit 1100 may store the feature information of the face of the user and the reference image correspondingly to the account information of the user. Also, the storage unit 1100 may store the facial condition information and the health status information correspondingly to the account information of the user.

The communication unit 1200 may transmit and receive data to and from an external device or an external server through a network connected to the service server 1000.

The communication unit 1200 may receive the account information and the face image of the user from the device 100. Also, the communication unit 1200 may transmit, to the device 100, the health status information obtained from the face image.

Also, the communication unit 1200 may receive a request for the prescription information suitable to the health status of the user from the device 100. Furthermore, the communication unit 1200 may receive a request for the hospital related service from the device 100.

Also, the communication unit 1200 may request a third party server for the prescription information suitable for the user. Also, the communication unit 1200 may request for hospital related information requested by the device 100 to the third party server. At this time, the communication unit 1200 may transmit the health status information of the user to the third party server.

Upon receiving the prescription information and the hospital related information based on the health status information from the third party server, the communication unit 1200 may transmit the prescription information and the hospital related information to the device 100.

The controller 1300 may control overall operations of the service server 1000 including the storage unit 1100 and the communication unit 1200.

The controller 1300 may authenticate the user based on the account information received from the device 100. Upon authenticating the user, the controller 1300 may obtain the facial condition information by analyzing the face image received from the device 100. At this time, the controller 1300 may obtain the facial condition information by comparing the face image with the reference image stored in the service server 1000. Also, the controller 1300 may obtain the health status information based on the facial condition information.

It is understood that names of the components of the device 100 described above may be changed or may vary. Also, the device 100 may include at least one of the components described above, may not include some of the components, or may further include other components.

One or more exemplary embodiments may also be embodied as computer-readable codes on a computer-readable recording medium. The computer-readable recording medium is any data storage device that can store data which can be thereafter read by a computer system.

The computer-readable codes are configured to perform operations realizing a method of controlling an electronic apparatus according to one or more exemplary embodiments when read from the computer-readable recording medium and executed by a processor. The computer-readable codes may be in various programming languages. Also, functional programs, codes, and code segments for accomplishing one or more exemplary embodiments may be easily construed by programmers skilled in the art to which the one or more exemplary embodiments pertains.

Examples of the computer-readable recording medium include read-only memory (ROM), random-access memory (RAM), CD-ROMs, magnetic tapes, floppy disks, optical data storage devices, etc. The computer-readable recording medium may also be distributed over network coupled computer systems so that the computer-readable code is stored and executed in a distributed fashion.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. While one or more exemplary embodiments have been described with reference to the figures above, it will be understood by those of ordinary skill in the art that various changes in form and details may be made therein without departing from the spirit and scope as defined by the following claims.

What is claimed is:

1. A device comprising:
a computer readable storage storing instructions; and
at least one processor configured to execute the stored instructions to:
extract a plurality of pieces of first health status information from a plurality of first image files of a user, each image file including a face of the user and previously stored in the storage;
store the plurality of pieces of first health status information in the storage;
capture a second image including the face of the user and second image data;
store the second image as a second image file;
extract second health status information from the captured second image;
store the second health status information in the storage;
automatically determine one first image file, from among the plurality of the first image files, as having first image data having a value of a characteristic corresponding most closely to a value of the characteristic of the second image data of the captured second image, wherein the characteristic corresponds to a photographing circumstance at a time of capture of the second image comprising at least one of lighting, a brightness of lighting, a direction of lighting, a color temperature of lighting, a place, a background, and a time zone;
select the one first image file as a reference image file for determining the health status information of the user; and
determine the health status information of the user by outputting the second image and a difference between a piece of first health status information extracted from the reference image file and the second health status information on a display of the device.

2. The device of claim 1, wherein, the processor is configured to execute the stored instructions to:
capture the second image when a first application is executed from among a plurality of applications in the device; and
output the second image and the difference between the piece of the first health status information and the second health status information when a second application that is different from the first application is executed.

3. The device of claim 1,
wherein the processor is configured to execute the stored instructions to capture the second image and to extract the second health status information from the captured second image based on receiving a user input for unlocking the device which is in a locked state.

4. The device of claim 1,
wherein the processor is configured to execute the stored instructions to capture the second image and extract the second health status information from the captured second image based on receiving a user input for executing a video call application in the device.

5. The device of claim 1, wherein the plurality of the first images are photographs that are received from a server in which the user is registered.

6. The device of claim 1, wherein the processor is configured to execute the stored instructions to:
normalize a resolution of the face of the user in the captured second image by expanding or reducing a size of the second image to a pre-set size; and
extract the second health status information from the normalized second image.

7. The device of claim 1, wherein the processor is configured to execute the stored instructions to:
obtain a color temperature of illumination on the face of the user at a point of time when the second image is captured;
normalize a hue value of the face of the user by adjusting a hue value of the second image based on the obtained color temperature; and
extract the second health status information from the normalized second image.

8. The device of claim 1, wherein the processor is further configured to execute the stored instructions to output an indicator indicating which region in the second image is related to the difference between the piece of the first health status information and the second health status information.

9. The device of claim 1, wherein to output, in chronological order, a plurality of second images that are captured during a predetermined time period and health status information extracted from the plurality of second images.

10. The device of claim 1, wherein the processor is configured to execute the stored instructions to output photographing guide information for guiding capturing of the face of the user based on a pre-set face image obtaining condition, and the processor is configured to execute the stored instructions.

11. The device of claim 1, wherein the processor is configured to execute the stored instructions to:
- obtain bio-information of the user at a point of time when the second image is captured;
- determine a biological condition of the user at the point of time based on the obtained bio-information; and
- extract the second health status information based on the determined biological condition.

12. A method of providing health status information, by a device, comprising a computer readable storage storing instructions, and a processor configured to perform the method, the method comprising:
- extracting a plurality of pieces of first health status information from a plurality of first image files of a user, each image file including a face of the user and previously stored in the storage;
- storing the plurality of pieces of first health status information in the storage;
- capturing a second image including the face of the user and second image data;
- storing the second image as a second image file;
- extracting second health status information from the captured second image;
- storing the second health status information in the storage;
- automatically determining one first image file, from among the plurality of the first image files, as having first image data having a value of a characteristic corresponding most closely to a value of the characteristic of the second image data of the captured second image, wherein the characteristic corresponds to a photographing circumstance at a time of capture of the second image comprising at least one of lighting, a brightness of lighting, a direction of lighting, a color temperature of lighting, a place, a background, and a time zone;
- selecting the one first image file as a reference image file for determining the health status information of the user; and
- determining the health status information of the user by outputting the second image and a difference between a piece of first health status information extracted from the reference image file and the second health status information on a display of the device.

13. The method of claim 12, wherein:
the capturing the second image comprises, capture the second image when a first application is executed from among a plurality of applications in the device; and
the outputting the second image and the difference comprises, controlling to output the second image and the difference between the piece of the first health status information and the second health status information when a second application that is different from the first application is executed.

14. The method of claim 12,
wherein the capturing the second image comprises controlling to capture the second image based on receiving a user input for unlocking the device which is in a locked state.

15. The method of claim 12,
wherein the capturing the second image comprises, controlling to capture the second image based on receiving a user input for executing a video call application in the device.

16. The method of claim 12, wherein the plurality of first images are photographs that are received from a server in which the user is registered.

17. The method of claim 12, wherein the controlling to extract the second health status information comprises:
- normalizing a resolution of the face of the user in the second image by expanding or reducing a size of the second image to a pre-set size; and
- extracting the second health status information from the normalized second image.

18. The method of claim 12, wherein the controlling to extract the second health status information comprises:
- obtaining a color temperature of illumination on the face of the user at a point of time when the second image is captured;
- normalizing a hue value of the face of the user by adjusting a hue value of the second image based on the obtained color temperature; and
- extracting the second health status information from the normalized second image.

19. The method of claim 12, further comprising outputting an indicator indicating which region in the second image is related to the difference between the piece of the first health status information and the second health status information.

20. The method of claim 12, wherein the controlling to output the second image and the difference comprises outputting, in chronological order, a plurality of the second images that are captured during a predetermined time period and health status information extracted from the plurality of second images.

21. The method of claim 12, wherein the controlling to capture the second image comprises outputting photographing guide information for guiding capturing of the face of the user based on a pre-set face image obtaining condition, and the second image is an image satisfying the pre-set face image obtaining condition.

22. The method of claim 12,
wherein the extracting the second health status information comprises:
- obtaining bio-information of the user at a point of time when the second image is captured;
- determining a biological condition of the user at the point of time based on the detected bio-information; and
- extracting the second health status information based on the determined biological condition.

23. A non-transitory computer-readable recording medium having recorded thereon a program executable by a computer for performing the method of claim 12.

* * * * *